US008652787B2

(12) United States Patent
Samuels et al.

(10) Patent No.: US 8,652,787 B2
(45) Date of Patent: Feb. 18, 2014

(54) USE OF ERBB4 AS A PROGNOSTIC AND THERAPEUTIC MARKER FOR MELANOMA

(75) Inventors: Yardena R. Samuels, Potomac, MD (US); Todd D. Prickett, Sterling, VA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 170 days.

(21) Appl. No.: 13/128,125

(22) PCT Filed: Aug. 6, 2009

(86) PCT No.: PCT/US2009/053005
§ 371 (c)(1),
(2), (4) Date: Jul. 18, 2011

(87) PCT Pub. No.: WO2010/056406
PCT Pub. Date: May 20, 2010

(65) Prior Publication Data
US 2011/0262437 A1      Oct. 27, 2011

Related U.S. Application Data

(60) Provisional application No. 61/199,156, filed on Nov. 12, 2008.

(51) Int. Cl.
*C12Q 1/68*      (2006.01)

(52) U.S. Cl.
USPC ........................................ 435/6.14; 435/6.12

(58) Field of Classification Search
None
See application file for complete search history.

(56) References Cited

U.S. PATENT DOCUMENTS

| 5,804,396 A | 9/1998 | Plowman |
| 5,811,098 A | 9/1998 | Plowman et al. |
| 2002/0156083 A1 | 10/2002 | Tang et al. |
| 2004/0116330 A1 | 6/2004 | Naito et al. |
| 2005/0101618 A1 | 5/2005 | Connell et al. |
| 2006/0148824 A1 | 7/2006 | Burns et al. |
| 2006/0233808 A1 | 10/2006 | Deperthes et al. |
| 2007/0128636 A1 | 6/2007 | Baker et al. |
| 2008/0031893 A1 | 2/2008 | Tripp et al. |

FOREIGN PATENT DOCUMENTS

| WO | WO 96/12019 | 4/1996 |
| WO | WO 03/012072 | 2/2003 |
| WO | WO 03/070912 | 8/2003 |
| WO | WO 2006/074430 | 7/2006 |
| WO | WO 2008/005983 | 1/2008 |
| WO | WO 2008/064884 | 6/2008 |

OTHER PUBLICATIONS

Soung et al., Int J Cancer, 2006, 118:1426-1429, IDS.*
Bardelli et al., "Mutational Analysis of the Tyrosine Kinome in Colorectal Cancers," *Science*, vol. 300:949, 2003.
Burris III et al., "Phase I Safety, Pharmacokinetics, and Clinical Activity Study of Lapatinib (GW572016), a Reversible Dual Inhibitor of Epidermal Growth Factor Receptor Tyrosine Kinases, in Heavily Pretreated Patients with Metastatic Carcinomas," *J. Clin. Oncol.*, vol. 23(23):5305-5313, 2005.
Greenman et al., "Patterns of Somatic Mutation in Human Cancer Genomes," *Nature*, vol. 446: 153-158, 2007.
Heymach et al., "Epidermal Growth Factor Receptor Inhibitors in Development for the Treatment of Non-Small Cell Lung Cancer," *Clin. Cancer Res.*, vol. 12:4441S-4445S, 2006.
Junttila et al., "Cleavable ErbB4 Isoform in Estrogen Receptor-Regulated Growth of Breast Cancer Cells," *Cancer Res.*, vol. 65(4):1384-1393, 2005.
Parsons et al., "Mutations in a Signalling Pathway," *Nature*, vol. 436:792, 2005.
Prickett et al., "Analysis of the Tyrosine Kinome in Melanoma Reveals Recurrent Mutations in *ERBB4*," *Nature Gen.*, vol. 41(10):1127-1134, 2009.
Rokavec et al., "A Novel Polymorphism in the Promoter Region of *ERBB4* is Associated with Breast and Colorectal Cancer Risk," *Clin. Cancer Res.*, vol. 13(24):7506-7514, 2007.
Samuels et al., "High Frequency of Mutations of the *PIK3CA* Gene in Human Cancers," *Science*, vol. 304:554, 2004.
Samuels et al., "Mutant PIK3CA Promotes Cell Growth and Invasion of Human Cancer Cells," *Cancer Cell*, vol. 7:561-573, 2005.
Sharma et al., "Epidermal Growth Factor Receptor Mutations in Lung Cancer," *Nature Rev. Cancer*, vol. 7:169-181, 2007.
Starr et al., "ErbB4 Increases the Proliferation Potential of Human Lung Cancer Cells and its Blockage Can Be Used as a Target for Anti-Cancer Therapy," *Int. J. Cancer*, vol. 199:269-274, 2006.
Soung et al., "Somatic Mutations of the ERBB4 Kinase Domain in Human Cancers," *Int. J. Cancer*, vol. 118:1426-1429, 2006.
Willmore-Payne et al., "BRAF and C-Kit Gene Copy Number in Mutation-Positive Malignant Melanoma," *Hum. Pathol.*, vol. 37:520-527, 2006.

* cited by examiner

*Primary Examiner* — Laura B Goddard
(74) *Attorney, Agent, or Firm* — Klarquist Sparkman, LLP

(57) ABSTRACT

It is disclosed herein that members of the protein tyrosine kinase (PTK) family are highly mutated in patients with melanoma. Described herein are novel somatic mutations in the ERBB4 gene that result in increased kinase activity, transformation ability and anchorage-independent growth. These ERBB4 mutations contribute to the tumorogenicity of melanoma. Thus, provided herein is a method of predicting the prognosis of a patient with melanoma by detecting the presence or absence of a mutation in the ERBB4 gene. In some examples, the ERBB4 mutation is selected from G949A, G1354A, G1624A, C1630T, G1687A, G2506A and G2614A (numbering based on SEQ ID NO: 1). Also provided are methods of selecting a patient as a candidate for treatment with an ERBB4 and/or PI3K/AKT pathway inhibitor, and a method of identifying a therapeutic agent for the treatment of a subject diagnosed with melanoma. Oligonucleotides that specifically hybridize with an ERBB4 nucleic acid molecule comprising a novel mutation, and arrays comprising such oligonucleotides, are also provided.

5 Claims, 26 Drawing Sheets

ERBB4 IP

ERBB4 IP

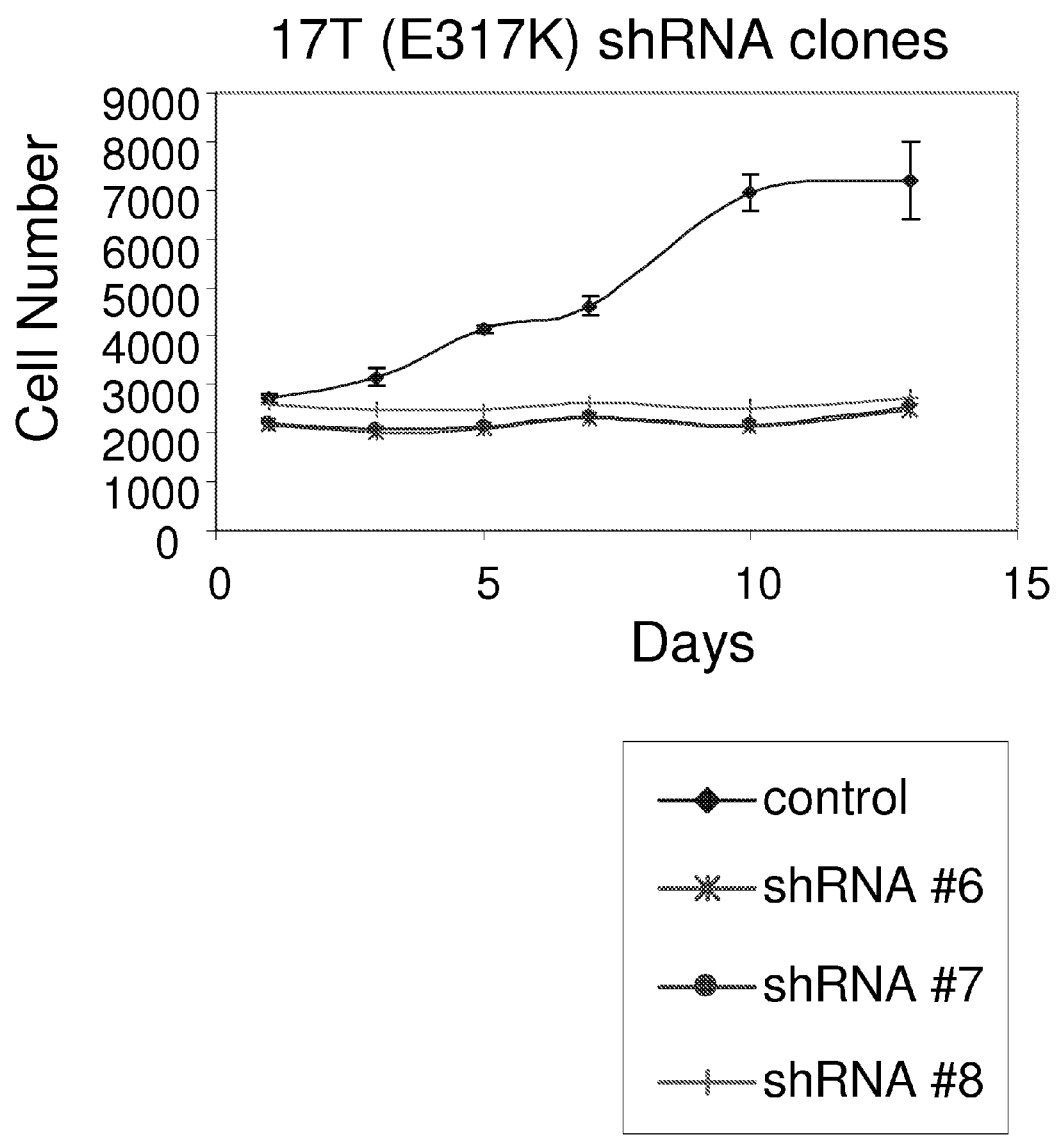

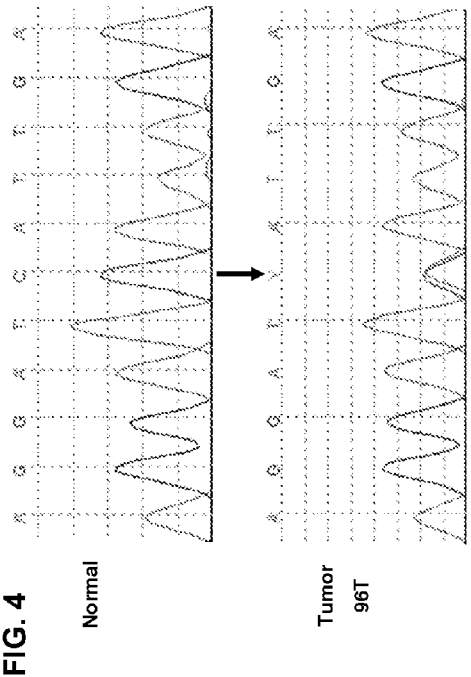
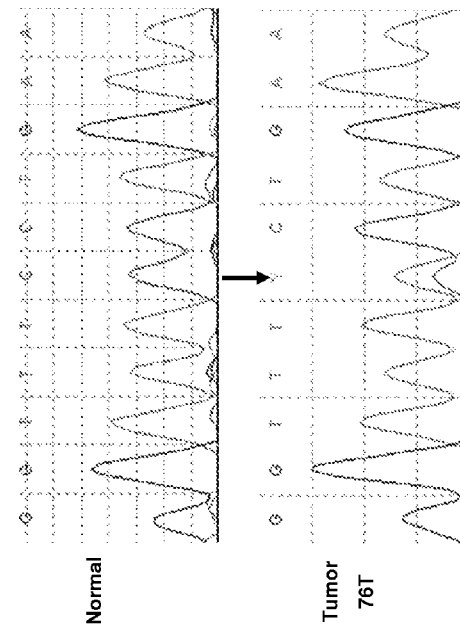
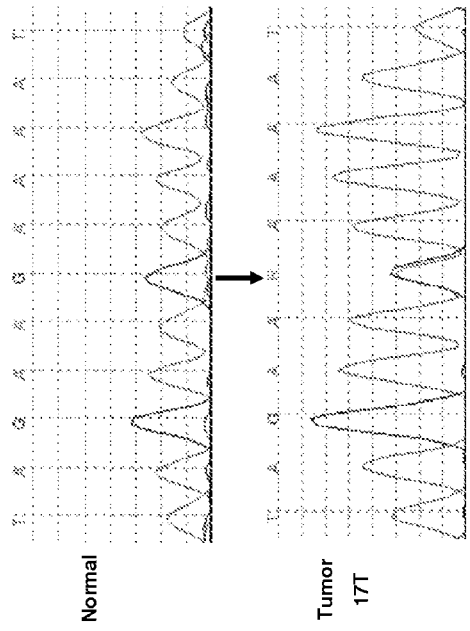
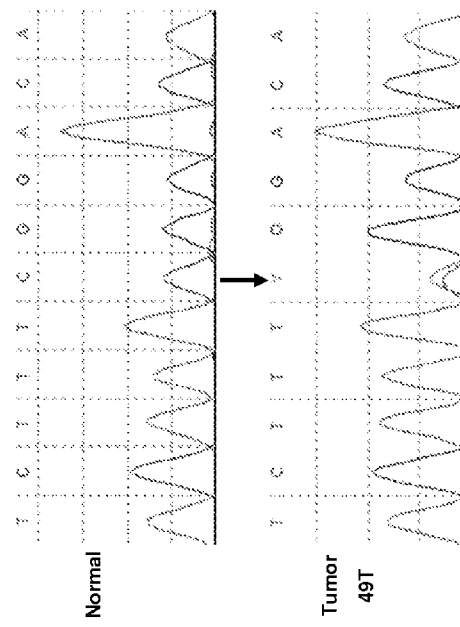
FIG. 4

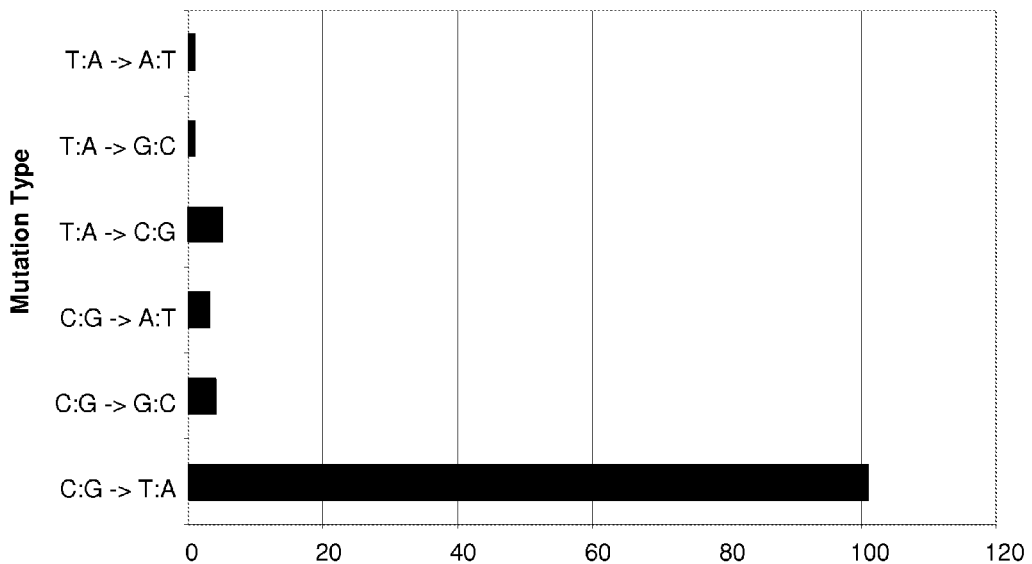
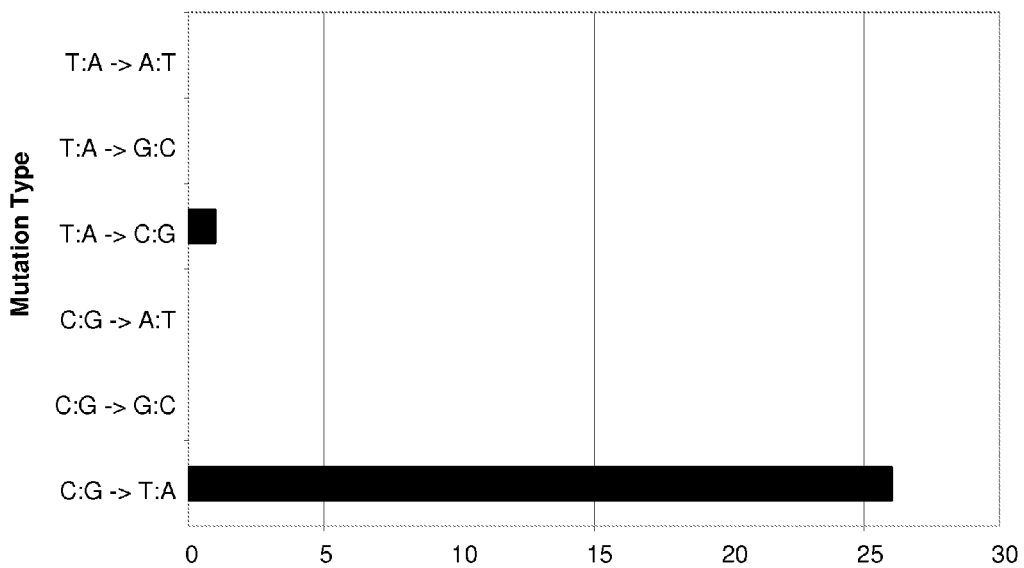

FIG. 7
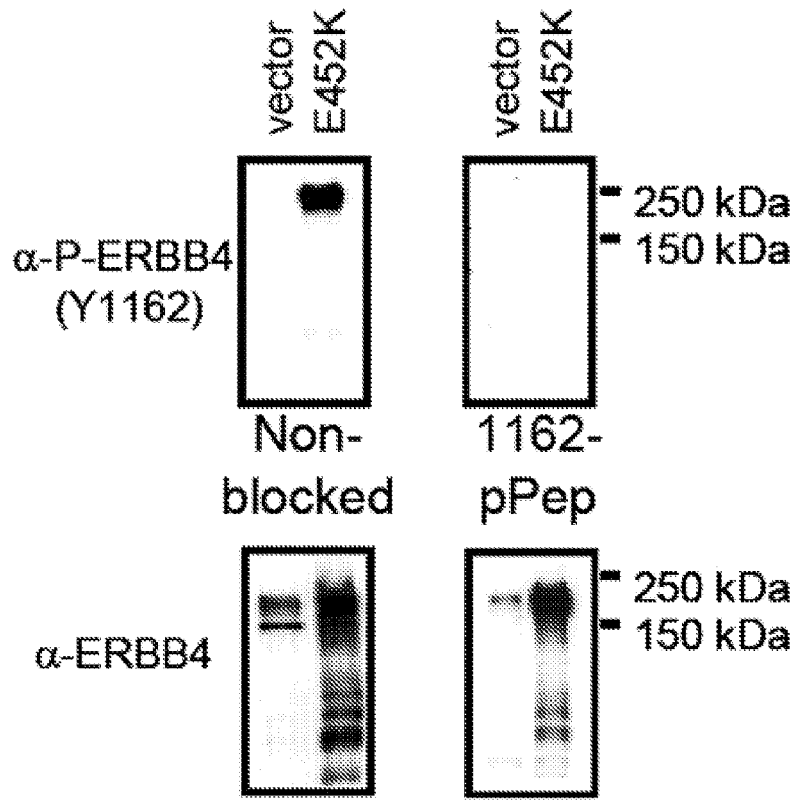
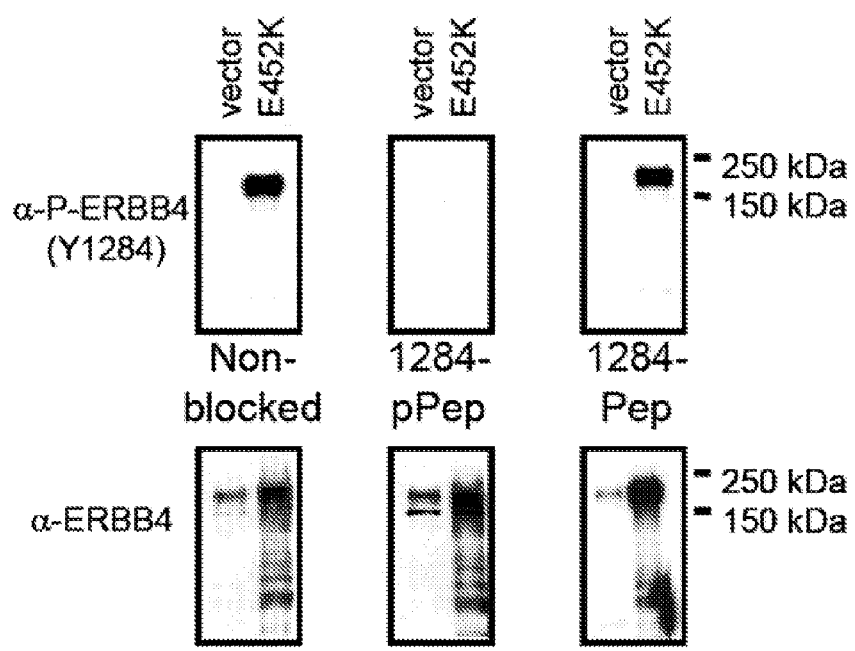

| Cell line (mutation) | IC50 (nM) | Std Error (+/- nM) |
|---|---|---|
| 68T (splice site) | 131.8 | 1.97 |
| 49T (R393W) | 259.6 | 3.27 |
| 12T (E563K) | 324.6 | 4.87 |
| 17T (E317K) | 513.8 | 6.36 |
| 7T (E452K) | 1365 | 19.3 |
| 71T (L39F, S1246N) | 1446 | 19.5 |
| 63T (M313I, E542K, E872K, R1174Q) | 3213 | 40.5 |
| 31T (WT) | 11370 | 157 |
| 93T (WT) | 31860 | 523 |
| 2T (WT) | 32980 | 861 |
| 39T (WT) | 34050 | 661 |

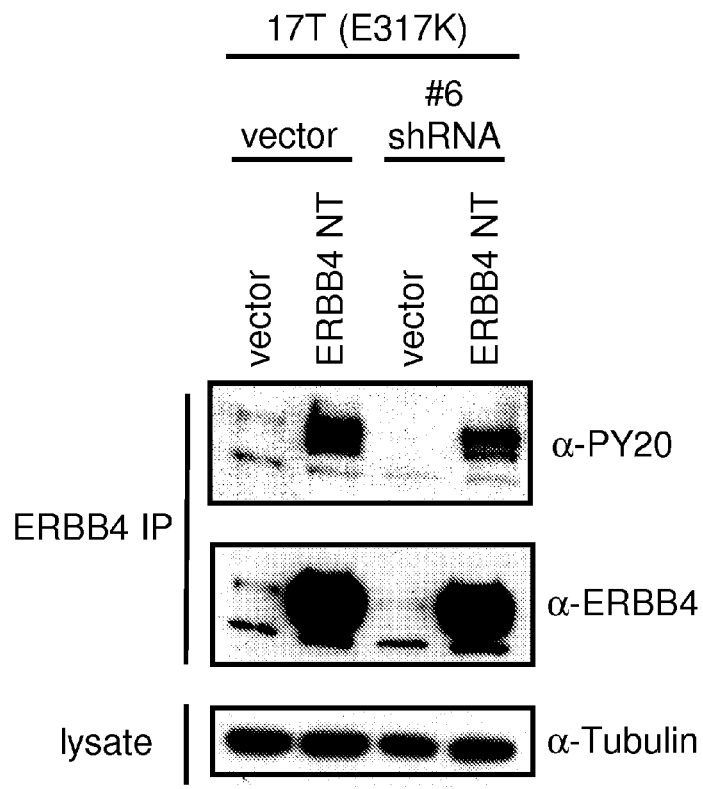
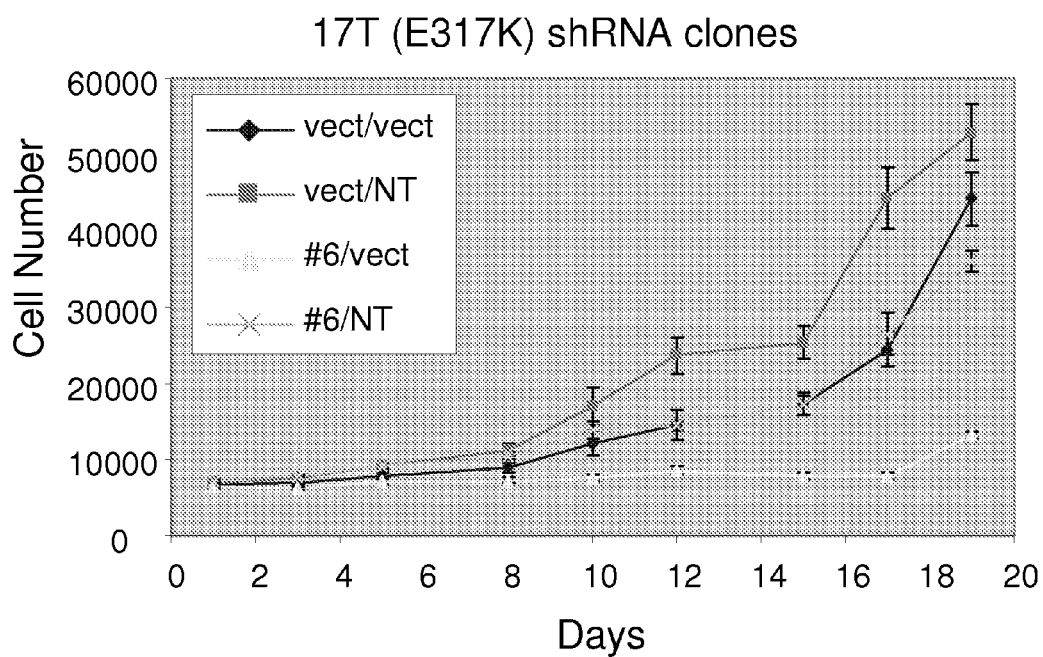

USE OF ERBB4 AS A PROGNOSTIC AND THERAPEUTIC MARKER FOR MELANOMA

CROSS REFERENCE TO RELATED APPLICATIONS

This application is the U.S. National Stage of International Application No. PCT/US2009/053005, filed Aug. 6, 2009, published in English under PCT Article 21(2), which claims the benefit of U.S. Provisional Application No. 61/199,156, filed Nov. 12, 2008, which is herein incorporated by reference in its entirety.

FIELD

This disclosure concerns the identification of novel mutations in members of the protein tyrosine (PTK) family, including ERBB4, and methods of use.

BACKGROUND

The protein tyrosine kinases (PTKs) are a family of proteins that catalyze phosphorylation of tyrosine residues in target proteins; PTKs play important roles in cellular signaling. Within this large family of proteins is the ERBB PTK family, which consists of four receptor kinases, ERBB1 (EGFR1, HER1), ERBB2 (c-Neu, HER2), ERBB3 (HER3) and ERBB4 (HER4). The ERBB kinases regulate a wide range of cellular responses, including cell proliferation, survival, migration and differentiation. ERBB signaling pathways are known to be altered in a wide variety of cancers, which has led to the development of drugs to specifically inhibit activity of members of this family (Junttila et al., *Cancer Res.* 65(4):1384-1393, 2005).

ERBB4 is a protein of approximately 180 kD and is expressed as four alternatively spliced isoforms. Previous studies of the role of ERBB4 in cancer development and prognosis have produced differing and sometimes contradictory results. For example, clinical studies of breast cancer have linked ERBB4 expression to either a favorable or adverse clinical outcome, and in vitro studies have suggested that in breast cancer cells, ERBB4 mediates either differentiation or tumorigenic growth (Junttila et al., *Cancer Res.* 65(4):1384-1393, 2005).

Cutaneous malignant melanoma is the most common fatal skin cancer (Jermal et al., *CA Cancer J. Clin.* 156(2):106-130, 2006; Tsao et al., *N. Engl. J. of Med.* 351:998-1012, 2004), and the incidence of this disease increases each year. Patients diagnosed with malignant melanoma have an average survival time of less than 10 months. PTKs are frequently mutated in cancer, and since they are amenable to pharmacologic inhibition (Futreal et al., *Nat. Rev. Cancer* 4:177-183, 2004; Sawyers, *Nature* 432:294-297, 2004), further analysis of the PTK gene family is needed to provide insight into melanoma pathogenesis and to identify new therapeutic strategies. Given the known role of PTKs in human cancer, and the disparate findings of studies of ERBB4 in cancer development, it is desirable to further evaluate ERBB4 in patients with malignant melanoma.

SUMMARY

It is disclosed herein that members of the protein tyrosine kinase family, including ERBB4, are highly mutated in melanoma tumors. Analysis of several ERBB4 mutants revealed that the mutations result in increased kinase activity of ERBB4 protein, increased transformation ability and increased anchorage-independent growth.

Thus, provided herein is a method of predicting the prognosis of a subject diagnosed with melanoma, comprising detecting the presence or absence of a mutation in the ERBB4 gene, wherein the presence of the mutation in the ERBB4 gene predicts a poor prognosis. In some embodiments, the ERBB4 mutation is selected from one or more of G949A, G1354A, G1624A, C1630T, G1687A, G2506A and G2614A (numbering based on SEQ ID NO: 1).

Also provided is a method of selecting a subject diagnosed with melanoma as a candidate for treatment with an ERBB4 inhibitor, a PI3K/AKT pathway inhibitor, or both, comprising detecting the presence or absence of a mutation in the ERBB4 gene of the subject, wherein the presence of a mutation in the ERBB4 gene indicates that the subject is a candidate for treatment with an ERBB4 inhibitor, a PI3K/AKT pathway inhibitor, or both. In some embodiments, the method further includes administering to the subject an ERBB4 inhibitor, a PI3K/AKT pathway inhibitor, or both. Further provided is a method of identifying a therapeutic agent for the treatment of a subject diagnosed with melanoma, comprising screening candidate agents to select an agent that decreases activity of ERBB4, or decreases activity of the PI3K/AKT pathway, thereby identifying a therapeutic agent for the treatment of a subject with melanoma. In some embodiments of the methods, the ERBB4 mutation is selected from G949A, G1354A, G1624A, C1630T, G1687A, G2506A and G2614A (numbering based on SEQ ID NO: 1).

Further provided are oligonucleotides that specifically hybridize with an ERBB4 nucleic acid molecule, wherein the ERBB4 nucleic acid molecule comprises at least one mutation selected from G949A, G1354A, G1624A, C1630T, G1687A, G2506A and G2614A (numbering based on SEQ ID NO: 1). Also provided are arrays comprising one or more of such ERBB4 mutant-specific oligonucleotides.

The foregoing and other features and advantages will become more apparent from the following detailed description of several embodiments, which proceeds with reference to the accompanying figures.

BRIEF DESCRIPTION OF THE FIGURES

FIG. 6: Mutation spectra of single base pair substitutions. (A) Shown is a Kinome mutation spectrum. The number of each of the six classes of base substitutions resulting in nonsynonymous changes in the kinome screen is shown. (B) Shown is a mutation spectrum of single base pair substitutions in ERBB4. The number of each of the six classes of base substitutions resulting in nonsynonymous changes in ERBB4 is shown.

FIG. 7: Specificity of phosphorylation site-specific antibodies. Shown is a series of immunoblots to detect phosphorylation status of ERBB4 mutants. HEK 293T cells were transiently transfected with either vector or ERBB4 E452K missense mutant. Cells were serum starved and then lysed. Shown are immunoblots of immunoprecipitated ERBB4 probed with several anti-phosphoERBB4 (Y1162; Y1284), or total ERBB4 antibodies in the presence or absence of phosphorylated (pPep) or unphosphorylated (Pep) competitive peptide.

FIG. 13: Rescue of oncogene dependence by exogenous non-targetable ERBB4. (A) Melanoma cells harboring mutant ERBB4 stably expressing control or ERBB4 shRNA #6 transduced with either vector or non-targetable (NT) ERBB4 were analyzed by immunoblotting with the indicated antibodies. As a loading control, lysates were immunoblotted with α-tubulin. (B) Melanoma cells expressing vector or the ERBB4 shRNA #6 transduced with a vector or NT ERBB4 were evaluated for cell proliferation by measuring the average cell number at each time point by determining DNA content using SYBR Green I.

SEQUENCE LISTING

Figure 1A:
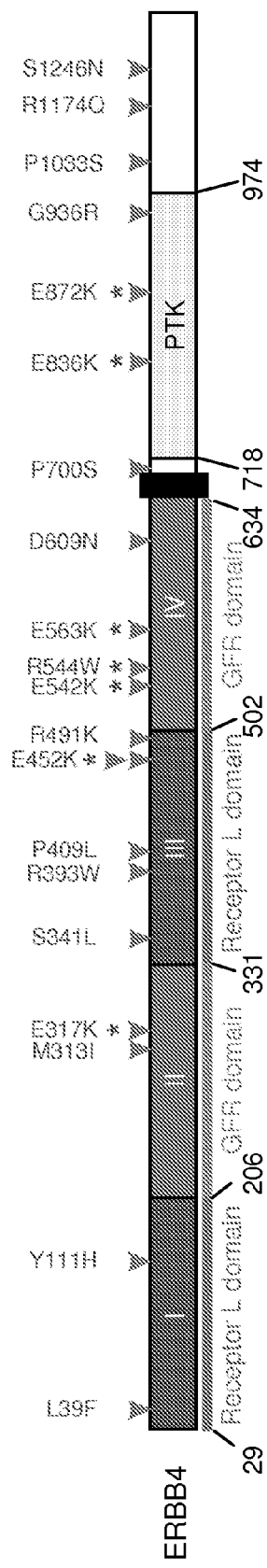
FIG. 1: Distribution of mutations in ERBB4 and increased basal activation of ERBB4 mutants. (A) Arrows indicate the location of ERBB4 somatic mutations found in this screen. Numbering of the ERBB4 amino acid residues is based on SEQ ID NO: 2. Stars indicate ERBB4 mutants evaluated for increased tyrosine kinase activity. Boxes represent functional domains (I, extracellular domain subregion I; II, extracellular domain subregion II; III, extracellular domain subregion III; IV, extracellular domain subregion IV; PTK, tyrosine kinase domain). (B) ERBB4 mutants have increased tyrosine phosphorylation. HEK 293T cells were transiently transfected with the indicated constructs. Twenty-four hours after transfection, cells were serum starved and lysed. Shown are immunoblots of immunoprecipitated ERBB4 probed with the indicated antibodies. Lysates were immunoprobed with an anti α-tubulin antibody. (C and D) ERBB4 mutants exhibit increased in vitro kinase activity. (C) HEK 293T cells were transiently transfected as in (B). Twenty-four hours after transfection, cells were either grown in 10% serum or serum starved and then lysed. Protein lysates were immunoprecipitated and used in a kinase assay. (D) The same samples that were used in the kinase assay were immunoblotted with ERBB4 antibody and lysates were blotted with α-tubulin (ns=non specific; KD=kinase dead). (E) ERBB4 mutants exhibit increased in vitro kinase activity. HEK 293T cells were transiently transfected as in (B). Equivalent amounts of protein from cell lysates were immunoprecipitated and used in a kinase assay to measure receptor autophosphorylation. The same samples that were used in the kinase assay were immunoblotted with ERBB4 antibody and lysates were blotted with α-tubulin. KD=kinase dead. (F) Increased basal activation of endogenous mutant ERBB4. Melanoma lines that harbor either WT or mutant ERBB4 were serum starved and then lysed, immunoprecipitated for ERBB4, then immunoblotted with α-PY20 or α-ERBB4. (G) Mutant ERBB4 has increased basal activity. Melanoma lines harboring either WT or mutant ERBB4 were serum deprived, lysed, immunoprecipitated for ERBB4, and analyzed by immunoblotting with α-P-ERBB4 (P-Y1162) or α-ERBB4.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on May 3, 2011, 46.4 KB, which is incorporated by reference herein. In the accompanying sequence listing:

SEQ ID NOs: 1 and 2 are the nucleotide and amino acid sequences, respectively, of human ERBB4 (GenBank Accession No. NM_005235.2, deposited Jul. 28, 2006). Seven mutations identified in melanoma tumors are indicated (G949A, G1354A, G1624A, C1630T, G1687A, G2506A and G2614A in the nucleotide sequence; E317K, E452K, E542K, R544W, E563K, E836K and E872K in the amino acid sequence).

SEQ ID NOs: 3-31 are the nucleotide sequences of forward primers used to PCR amplify the coding region of human ERBB4.

SEQ ID NOs: 32-60 are the nucleotide sequences of reverse primers used to PCR amplify the coding region of human ERBB4.

SEQ ID NO: 61 is the nucleotide sequences of the primer used to sequence the coding region of human ERBB4.

SEQ ID NOs: 62 and 63 are the nucleotide sequences of primers used to clone human ERBB4.

SEQ ID NOs: 64-70 are the nucleotide sequences of forward primers used to PCR amplify the kinase domain of human ERBB4.

SEQ ID NOs: 71-77 are the nucleotide sequences of reverse primers used to PCR amplify the kinase domain of human ERBB4.

SEQ ID NO: 78 is the nucleotide sequences of the forward primer used to sequence the kinase domain of human ERBB4.

SEQ ID NO: 79 is the nucleotide sequences of the reverse primer used to sequence the kinase domain of human ERBB4.

DETAILED DESCRIPTION

I. Introduction

PTK signaling pathways can be deregulated by a variety of mechanisms in human tumors. Described herein is a comprehensive mutational analysis of the PTK family, which revealed numerous novel somatic mutations. Surprisingly, the analysis identified two PTK genes that had mutations in over 10% of MM cases (FLT1 and PTK2B) and one gene that had mutations in over 18% of MM cases (ERBB4, a member of the EGFR family). The high frequency of mutations identified in ERBB4, their co-localization, and the identification of two identical missense mutations in multiple MM cases, suggest that these mutations play a role in tumorigenesis.

To evaluate the effect of mutations in ERBB4, seven mutations that affect residues that are conserved in EGFR, and are located at residues near EGFR mutations that have been described in other tumor types, were cloned and their kinase activity was examined. The results of this analysis showed that mutant ERBB4 has increased autophosphorylation activity compared to wild type (WT) ERBB4. Expression of mutant ERBB4 in NIH 3T3 cells and human melanoma cells increased their growth on soft agar and colony formation ability. Furthermore, immunoblots of melanoma cells harboring ERBB4 mutations exhibited increased activity of the PI3K/AKT pathway, as evidenced by an increase in phosphorylated AKT. These functional assays indicated that the ERBB4 mutations identified herein promote cellular phenotypes typical of neoplastic cells, such as increased transformation ability and anchorage-independent growth.

The combination of genetic, biochemical and cellular data disclosed herein indicates that ERBB4 functions as an oncogene in MM. This finding is consistent with previously reported alterations of members of the EGFR family, which have been shown to be mutated as well as amplified (Sharma et al., Nat. Rev. Cancer 7:169-181, 2007). In addition, ERBB4 has previously been shown to be involved in enhanced proliferation of breast cancer cells (Junttila et al., Cancer Res. 65(4):1384-1393, 2005) and non-small cell lung cancer cells (Starr et al., Int. J. Cancer 119:269-274, 2006). Importantly, cells containing mutations in ERBB4 were associated with enhanced and selective sensitivity to an FDA-approved ERBB4 inhibitor compared to WT cells. These results suggest that patients with melanoma containing one or more ERBB4 mutations may benefit from therapy directed at mutant ERBB4.

II. Abbreviations

| | |
|---|---|
| ARAF | v-raf murine sarcoma 3611 viral oncogene homolog |
| BRAF | B-Raf proto-oncogene serine/threonine-protein kinase |
| CRAF | v-raf-1 murine leukemia viral oncogene homolog 1 |
| DMEM | Dulbecco's modified eagle medium |
| DMSO | Dimethyl sulfoxide |
| DNA | Deoxyribonucleic acid |
| EGFR | Epidermal growth factor receptor |
| ELISA | Enzyme-linked immunosorbent assay |
| FBS | Fetal bovine serum |
| GFR | Growth factor receptor |
| HRAS | v-Ha-ras Harvey rat sarcoma viral oncogene homolog |
| $IC_{50}$ | Inhibitory concentration 50 |
| IG | Immunoglobulin |
| KD | Kinase dead |
| KO | Knockout |
| KRAS | v-Ki-ras2 Kirsten rat sarcoma viral oncogene homolog |
| MM | Metastatic melanoma |
| NRAS | Neuroblastoma RAS viral oncogene homolog |
| NT | Non-targetable |
| PAGE | Polyacrylamide-gel electrophoresis |
| PBS | Phosphate buffered saline |
| PCR | Polymerase chain reaction |
| PI3K | Phosphoinositide 3-kinase |
| RNA | Ribonucleic acid |
| RNAi | RNA interference |
| RT | Reverse transcriptase |
| SAM | Sterile alpha motif |
| SDS | Sodium dodecyl sulfate |
| shRNA | Short hairpin RNA |
| siRNA | Small interfering RNA |
| SNP | Single nucleotide polymorphism |
| TKI | Tyrosine kinase inhibitor |
| WT | Wild type |

III. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

AKT: As used herein, the term "AKT" includes AKT1, AKT2 and AKT3. The AKT1 gene encodes a serine-threonine protein kinase that is catalytically inactive in serum-starved primary and immortalized fibroblasts. AKT1 and the related AKT2 are activated by platelet-derived growth factor. The activation, which occurs through phosphatidylinositol 3-kinase, is rapid and specific, and it is abrogated by mutations in the pleckstrin homology domain of AKT1. AKT1 is also known as v-akt murine thymoma viral oncogene homolog 1, PKB; RAC; PRKBA; MGC99656; PKB-ALPHA; and RAC-ALPHA. The AKT2 gene is a putative oncogene encoding a protein belonging to a subfamily of serine/threonine kinases containing SH2-like (Src homology 2-like) domains. The Akt2 protein is a general protein kinase capable of phosphorylating several known proteins. AKT2 is also known as v-akt murine thymoma viral oncogene homolog 2; PKBB; PRKBB; PKBBETA; and RAC-BETA. AKT3 is a member of the AKT (also called PKB) serine/threonine protein kinase family. AKT kinases are known to be regulators of cell signaling in response to insulin and growth factors. They are involved in a wide variety of biological processes including cell proliferation, differentiation, apoptosis, tumorigenesis, as well as glycogen synthesis and glucose uptake. The Akt3 protein kinase has been shown to be stimulated by platelet-derived growth factor (PDGF), insulin, and insulin-like growth factor 1 (IGF1). AKT3 is also known as v-akt murine thymoma viral oncogene homolog 3; protein kinase B, gamma; PKBG; PRKBG; STK-2; PKB-GAMMA; RAC-gamma; RAC-PK-gamma; and DKFZp434N0250. Members of the AKT protein family are also called protein kinases B (PKB) in the literature.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds mesothelin.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Antisense compound: Refers to an oligomeric compound that is at least partially complementary to the region of a target nucleic acid molecule (such as a miR gene product) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression.

Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound. In particular examples herein, the antisense compound is an antisense oligonucleotide, siRNA or ribozyme.

Antisense oligonucleotide: As used herein, an "antisense oligonucleotide" is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target RNA molecule, the duplex is recognized by RNase H (an enzyme that recognizes DNA:RNA duplexes), resulting in cleavage of the RNA.

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least two, at least four, at least six, to at least 9, at least 10, at least 14, at least 15, at least 20, at least 30, at least 50, at least 75, at least 100, at least 150, at least 200, at least 300, at least 500, least 550, at least 600, at least 800, at least 1000, or more. In a particular example, an array includes 2-100 addressable locations, such as 4-20 addressable locations. In particular examples, an array consists essentially of oligonucleotide probes specific for ERBB4 nucleic acid molecules comprising mutations selected from G949A, G1354A, G1624A, C1630T, G1687A, G2506A and G2614A (numbered with reference to SEQ ID NO: 1).

In particular examples, an array includes nucleic acid molecules, such as oligonucleotide sequences that are at least 15 nucleotides in length, such as about 15-40 nucleotides in length.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Candidate: As used herein, a "candidate" for treatment with an ERBB4 inhibitor is a melanoma patient that is likely to respond favorably to treatment with the ERBB4 inhibitor. Candidates for ERBB4 inhibitor therapy are melanoma patients that have a mutation in the ERBB4 gene that results in an increase in ERBB4 expression, or results in expression of an ERBB4 protein with increased kinase activity. In some embodiments, the candidate is a melanoma patient with an ERBB4 gene comprising a mutation selected from G949A, G1354A, G1624A, C1630T, G1687A, G2506A and G2614A (numbered with reference to SEQ ID NO: 1). In some embodiment, the ERBB4 protein comprises a mutation selected from E317K, E452K, E542K, R544W, E563K, E836K and E872K (numbered with reference to SEQ ID NO: 2).

Clinical outcome: Refers to the health status of a patient following treatment for a disease or disorder, or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient. A decrease in survival also can refer to a decrease in the average time to death in a group, such as a group of patients diagnosed with melanoma.

Epidermal growth factor receptor (EGFR) family: A family of protein tyrosine kinases (PTKs), also known as the ERBB family. The ERBB PTK family includes four receptor kinases, ERBB1 (EGFR1, HER1), ERBB2 (c-Neu, HER2), ERBB3 (HER3) and ERBB4 (HER4). The ERBB kinases regulate a wide range of cellular responses, including cell proliferation, survival, migration and differentiation. ERBB signaling pathways are known to be altered in a wide variety of cancers.

ERBB4: A member of the EGFR family that encodes a protein of approximately 180 kD. ERBB4 encodes a single-pass type I membrane protein with multiple cysteine rich domains, a transmembrane domain, a tyrosine kinase domain, a phosphotidylinositol-3 kinase binding site and a PDZ domain binding motif. ERBB4 is expressed as four alternatively spliced isoforms. The protein binds to and is activated by neuregulins and other factors and induces a variety of cellular responses, including mitogenesis and differentiation. Multiple proteolytic events allow for the release of a cytoplasmic fragment and an extracellular fragment. Mutations in ERBB4 have been associated with cancer.

ERBB4 inhibitor: An ERBB4 inhibitor refers to any compound that inhibits expression or activity of ERBB4, such as kinase activity of ERBB4. Inhibitor compounds include, but are not limited to, small molecules, polypeptides and nucleic acid molecules (such as antisense compounds). In some embodiments, an ERBB4 inhibitor is a broad-spectrum inhibitor that inhibits activity of multiple members of the EGFR family. EGFR family inhibitors are known in the art (see, for example, PCT Publication Nos. WO 2008/005983, WO 03/012072 and WO 03/070912; and US Patent Application Publication Nos. 2006/0233808 and 2006/0128636). In some embodiments, the ERBB4 inhibitor selectively inhibits expression or activity of ERBB4, and not other EGFR family members (see, for example, U.S. Pat. No. 5,811,098). In some embodiments, the ERBB4 inhibitor is a kinase inhibitor. Kinase inhibitors are well known in the art (see, for example, US Patent Application Publication Nos. 2008/0031893; 2006/0148824; and 2002/0156083). In particular examples, the ERBB4 inhibitor is lapatinib (Burris et al., *J. Clin. Oncol.* 23(23):5305-5313, 2005).

Genomic DNA: The DNA found within the nucleus and containing an organism's genome, which is passed on to its offspring as information for continued replication and/or propagation and/or survival of the organism. The term can be used to distinguish between other types of DNA, such as DNA found within plasmids or organelles.

Inhibitor: As used herein, the term "inhibitor" includes any type of molecule that inhibits the expression or activity of a target gene or protein. An inhibitor can be any type of compound, such as a small molecule, antibody or antisense compound.

Kinase: An enzyme that catalyzes the transfer of a phosphate, such as from ATP, to a substrate. As used herein, an increase or decrease in "kinase activity" of a protein (e.g. ERBB4) refers to an increase or decrease in the ability of the protein to phosphorylate a substrate, such as a protein.

Label: An agent capable of detection, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

In some embodiments, the label is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ.

Examples of fluorophores that may be used are provided in U.S. Pat. No. 5,866,366 to Nazarenko et al., and include for instance: 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DAB CYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other contemplated fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

LY294002: A selective small molecule inhibitor of PI3K. LY294002 is also known as 2-(4-morpholinyl)-8-phenyl-4H-1-benzopyran-4-one (Vlahos et al., *J Biol Chem* 269:5241-5248, 1994). The molecular formula of LY294002 is $C_{19}H_{17}NO_3$.

Melanoma: A form of cancer that originates in melanocytes (cells that make the pigment melanin). Melanocytes are found primarily in the skin, but are also present in the bowel and eye.

Metastasis: Refers to the spread of cancer cells from the original tumor to other sites in the body.

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," as discussed below, but generally refers to the subset of constitutional alterations that have arisen within the past few generations in a kindred and that are not widely disseminated in a population group.

In some embodiments, a mutation in ERBB4 refers to a nucleotide substitution in the ERBB4 gene or cDNA, or an amino acid substitution in the ERBB4 protein.

Oligonucleotide: A linear polynucleotide sequence of up to about 100 nucleotide bases in length.

Patient or subject: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phosphoinositide-3 kinase (PI3K): A family of related enzymes that are capable of phosphorylating the 3 position hydroxyl group of the inositol ring of phosphatidylinositol. PI3Ks are also known as phosphatidylinositol-3-kinases. Class I PI3K are heterodimeric molecules composed of a regulatory subunit and a catalytic subunit. Class II and Class III PI3K are differentiated from Class I by their structure and function. Class II PI3K are composed of one of three catalytic isoforms (C2α, C2β, and C2γ), but have no regulatory proteins. Class III PI3K exist as a heterodimers of a catalytic subunit (Vps34) and a regulatory (p150) subunit. Genes encoding PIK3 subunits include, for example, PIK3C2A, PIK3C2B, PIK3C2G, PIK3C3, PIK3CA, PIK3CB, PIK3CG, PIK3CD, PIK3R1, PIK3R2, PIK3R3, PIK3R4, PIK3R4, PIK3R5 and PIK3R6.

PI3K/Akt pathway: A signaling pathway involved in a number of cellular processes, such as cell growth, proliferation, differentiation, motility, survival, intracellular trafficking, metabolism and angiogenesis.

PI3K/Akt pathway inhibitor: Any compound that inhibits expression or activity of a member of the PI3K pathway, such as, but not limited to PI3K or AKT. For example, the inhibitor can be a small molecule, antibody, antisense compound or polypeptide. In some examples, the antibody is a chimeric antibody, a humanized antibody or a human antibody. In some examples, the antisense compound is an antisense oligonucleotide, siRNA or ribozyme. Antibodies, antisense compounds and other inhibitors specific for members of the PI3K/Akt pathway are known in the art and are commercially available. Exemplary inhibitors of the PI3K/Akt pathway are described herein, but are not intended to be limiting. In some examples, the small molecule inhibitor of PI3K is LY294002 (also known as 2-(4-morpholinyl)-8-phenyl-4H-1-benzopyran-4-one; molecular formula $C_{19}H_{17}NO_3$) or wortmannin (molecular formula $C_{23}H_{24}O_8$). In some examples, the small molecule inhibitor of Akt is UCN-01 (also known as 7-hydroxystaurosporine and 8,12-epoxy-1H,8H-2,7b,12a-triazadibenzo[a, g]cyclonona[cde]trinden-1-one, 2,3,9,10,11,12-hexahydro-3-hydroxy-9-methoxy-8-methyl-10-(methylamino)). UCN-01 is a synthetic derivative of staurosporine with antineoplastic activity. Antisense compounds specific for members for the PI3K/Akt pathway have been previously described. For example, U.S. Patent Application Publication Nos. 2005/02772682 and 2004/0077580 disclose siRNAs and antisense oligonucleotides specific for PI3K. In addition, U.S. Patent Application Publication Nos. 2008/0161547, 2004/0265999 and 2003/0148974 describe antisense oligonucleotide and siRNA compounds that target AKT. Antibodies specific for members of the PI3K/Akt pathway have been described in the art and are commercially available from a variety of sources. For example, PI3K antibodies are disclosed in U.S. Patent Application Publication No. 2008/0014598.

Polymorphism: Variant in a sequence of a gene, or any genomic sequence, usually carried from one generation to another in a population. Polymorphisms can be those variations (nucleotide sequence differences) that, while having a different nucleotide sequence, produce functionally equivalent gene products, such as those variations generally found between individuals, different ethnic groups, and geographic locations. The term polymorphism also encompasses variations that produce gene products with altered function, i.e., variants in the gene sequence that lead to gene products that are not functionally equivalent. This term also encompasses variations that produce no gene product, an inactive gene product, a truncated gene product, or increased or increased activity gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stem-loop, or an alteration of the binding affinity of the nucleic acid for associated molecules, such as polymerases, RNAses, a change in the availability of a site for cleavage by a restriction endonuclease, either the formation of a new site, or lose of a site, and so forth).

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown in the following table:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease (such as metastatic melanoma) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Probes and primers: A probe comprises an isolated nucleic acid capable of hybridizing to a target nucleic acid. A detectable label or reporter molecule can be attached to a probe or primer. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example in Sambrook et al. (In *Molecular Cloning: A Laboratory Manual*, CSHL, New York, 1989) and Ausubel et al. (In *Current Protocols in Molecular Biology*, John Wiley & Sons, New York, 1998). In some embodiments, an "oligonucleotide" is a probe or primer.

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 15 nucleotides in length, such as at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, or more contiguous nucleotides complementary to the target nucleic acid molecule, such as 15-70 nucleotides, 15-60 nucleotides, 15-50 nucleotides, 15-40 nucleotides, or 15-30 nucleotides.

Primers are short nucleic acid molecules, for instance DNA oligonucleotides 10 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 55, 60, 65, 70 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, or more contiguous nucleotides complementary to the target nucleic acid molecule to be amplified, such as a primer of 15-70 nucleotides, 15-60 nucleotides, 15-50 nucleotides, 15-40 nucleotides or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein. It is also appropriate to generate probes and primers based on fragments or portions of these disclosed nucleic acid molecules, for instance regions that encompass the identified polymorphisms of interest. PCR primer pairs can be derived from a known sequence by using computer programs intended for that purpose such as Primer (Version 0.5., © 1991, Whitehead Institute for Biomedical Research, Cambridge, Mass.) or PRIMER EXPRESS® Software (Applied Biosystems, AB, Foster City, Calif.).

Prognosis: The likelihood of the clinical outcome for a subject afflicted with a specific disease or disorder. With regard to cancer, the prognosis is a representation of the likelihood (probability) that the subject will survive (such as for one, two, three, four or five years) and/or the likelihood (probability) that the tumor will metastasize. A "poor prognosis" indicates a greater than 50% chance that the subject will not survive to a specified time point (such as one, two, three, four or five years), and/or a greater than 50% chance that the tumor will metastasize. In several examples, a poor prognosis indicates that there is a greater than 60%, 70%, 80%, or 90% chance that the subject will not survive and/or a greater than 60%, 70%, 80% or 90% chance that the tumor will metastasize. Conversely, a "good prognosis" indicates a greater than 50% chance that the subject will survive to a specified time point (such as one, two, three, for or five years), and/or a greater than 50% chance that the tumor will not metastasize. In several examples, a good prognosis indicates that there is a greater than 60%, 70%, 80%, or 90% chance that the subject will survive and/or a greater than 60%, 70%, 80% or 90% chance that the tumor will not metastasize.

Protein tyrosine kinase (PTK): A family of proteins that catalyze phosphorylation of tyrosine residues in target proteins. PTKs play important roles in cellular signaling.

Ribozyme: A catalytic RNA molecule. In some cases, ribozymes can bind to specific sites on other RNA molecules and catalyze the hydrolysis of phosphodiester bonds in the RNA molecules.

RNA interference (RNAi): Refers to a cellular process that inhibits expression of genes, including cellular and viral genes. RNAi is a form of antisense-mediated gene silencing involving the introduction of double stranded RNA-like oligonucleotides leading to the sequence-specific reduction of RNA transcripts. Double-stranded RNA molecules that inhibit gene expression through the RNAi pathway include siRNAs, miRNAs, and shRNAs.

Sample: A biological specimen containing genomic DNA, RNA, protein, or combinations thereof, obtained from a subject. Examples include, but are not limited to, peripheral blood, urine, saliva, tissue biopsy (such as skin tissue), surgical specimen, and autopsy material. In one example, a sample includes a biopsy of a melanoma tumor or a sample of normal tissue (from a subject not afflicted with a known disease or disorder, such as a cancer-free subject).

Screening: As used herein, "screening" refers to the process used to evaluate and identify candidate agents that decrease kinase activity of ERBB4 protein. In some cases, screening involves contacting a candidate agent (such as a small molecule, peptide or nucleic acid molecule) with cells expressing ERBB4 and testing the effect of the agent on kinase activity of ERBB4. In some embodiments, the cells express WT ERBB4. In other embodiments, the cells express mutant ERBB4, such as an ERBB4 protein comprising a mutation selected from E317K, E452K, E542K, R544W, E563K, E836K and E872K (numbered with reference to SEQ ID NO: 2).

Short hairpin RNA (shRNA): A sequence of RNA that makes a tight hairpin turn and can be used to silence gene expression via the RNAi pathway. The shRNA hairpin structure is cleaved by the cellular machinery into siRNA.

Small interfering RNA (siRNA): A double-stranded nucleic acid molecule that modulates gene expression through the RNAi pathway. siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs."

Small molecule: A molecule, typically with a molecular weight less than about 1000 Daltons, or in some embodiments, less than about 500 Daltons, wherein the molecule is capable of modulating, to some measurable extent, an activity of a target molecule.

Specific hybridization: Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (In: *Molecular Cloning: A Laboratory Manual*, Cold Spring Harbor, N.Y., 1989 ch. 9 and 11). By way of illustration only, a hybridization experiment may be performed by hybridization of a DNA molecule to a target DNA molecule which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989).

Traditional hybridization with a target nucleic acid molecule labeled with [$^{32}P$]-dCTP is generally carried out in a solution of high ionic strength such as 6×SSC at a temperature that is 20-25° C. below the melting temperature, $T_m$, described below. For Southern hybridization experiments where the target DNA molecule on the Southern blot contains 10 ng of DNA or more, hybridization is typically carried out for 6-8 hours using 1-2 ng/ml radiolabeled probe (of specific activity equal to $10^9$ CPM/µg or greater). Following hybridization, the nitrocellulose filter is washed to remove background hybridization. The washing conditions should be as stringent as possible to remove background hybridization but to retain a specific hybridization signal.

The term $T_m$ represents the temperature (under defined ionic strength, pH and nucleic acid concentration) at which 50% of the probes complementary to the target sequence hybridize to the target sequence at equilibrium. Because the target sequences are generally present in excess, at $T_m$ 50% of the probes are occupied at equilibrium. The $T_m$ of such a hybrid molecule may be estimated from the following equation (Bolton and McCarthy, *Proc. Natl. Acad. Sci. USA* 48:1390, 1962):

$$T_m = 81.5°\ C. - 16.6(\log_{10}[Na^+]) + 0.41(\%\ G+C) - 0.63(\%\ formamide) - (600/l)$$

where l=the length of the hybrid in base pairs.

This equation is valid for concentrations of $Na^+$ in the range of 0.01 M to 0.4 M, and it is less accurate for calculations of Tm in solutions of higher [$Na^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (*Molecular Cloning: A Laboratory Manual*, Cold Spring Harbor, N.Y., 1989).

Thus, by way of example, for a 150 base pair DNA probe derived from a cDNA (with a hypothetical % GC of 45%), a calculation of hybridization conditions required to give particular stringencies may be made as follows: For this example, it is assumed that the filter will be washed in 0.3× SSC solution following hybridization, thereby: [$Na^+$]=0.045 M; % GC=45%; Formamide concentration=0; l=150 base pairs; $T_m=81.5-16.6(\log_{10}[Na^+])+(0.41\times45)-(600/150)$; and so $T_m$=74.4° C.

The $T_m$ of double-stranded DNA decreases by 1-1.5° C. with every 1% decrease in homology (Bonner et al., *J. Mol. Biol.* 81:123, 1973). Therefore, for this given example, washing the filter in 0.3×SSC at 59.4-64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4-68.4° C. will yield a hybridization stringency of 94%; that is, DNA molecules with more than 6% sequence variation relative to the target cDNA molecule will not hybridize. The above example is given entirely by way of theoretical illustration. It will be appreciated that other hybridization techniques may be utilized and that variations in experimental conditions will necessitate alternative calculations for stringency.

Stringent conditions may be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25-30° C. are suitable for allele-specific probe hybridizations.

The following is an exemplary set of hybridization conditions and is not meant to be limiting:

Very High Stringency (Detects Sequences that Share 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share 80% Identity or Greater)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share Greater than 50% Identity)
Hybridization: 6×SSC at RT to 55° C. for 16-20 hours
Wash at least twice: 2×-3×SSC at RT to 55° C. for 20-30 minutes each.

A perfectly matched probe has a sequence perfectly complementary to a particular target sequence. The test probe is typically perfectly complementary to a portion (subsequence) of the target sequence. The term "mismatch probe" refers to probes whose sequence is deliberately selected not to be perfectly complementary to a particular target sequence.

Therapeutic: A generic term that includes both diagnosis and treatment.

Therapeutic agent: A chemical compound, small molecule, or other composition, such as an antisense compound, antibody, peptide, nucleic acid molecule, protease inhibitor, hormone, chemokine or cytokine, capable of inducing a desired therapeutic or prophylactic effect when properly administered to a subject. For example, therapeutic agents for melanoma include agents that prevent or inhibit development or metastasis of melanoma. As used herein, a "candidate agent" is a compound selected for screening to determine if it can function as a therapeutic agent for melanoma. In some embodiments, a "candidate agent" is an agent screened to determine if is capable of increasing kinase activity of ERBB4. "Incubating" includes a sufficient amount of time for an agent to interact with a cell or tissue. "Contacting" includes incubating an agent in solid or in liquid form with a cell or tissue. "Treating," when used to refer to the treatment of a cell or tissue with a therapeutic agent, includes contacting or incubating an agent with the cell or tissue.

Transformation: Refers to the transition of a normal cell to a malignant cell.

Tumor, neoplasia, malignancy or cancer: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

UCN-01 (7-hydroxystaurosporine): A synthetic derivative of staurosporine with antineoplastic activity. UCN-01 inhibits many phosphokinases, including AKT, calcium-dependent protein kinase C, and cyclin-dependent kinases. The chemical structure name of UCN-01 is 8,12-epoxy-1H,8H-2,7b,12a-triazadibenzo[a, g]cyclonona[cde]trinden-1-one, 2,3,9,10,11,12-hexahydro-3-hydroxy-9-methoxy-8-methyl-10-(methylamino).

Wortmannin: A furanosteroid metabolite of the fungi Penicillium funiculosum, Talaromyces (Penicillium) wortmannii, is a specific, covalent inhibitor of PI3K. The molecular formula of wortmannin is $C_{23}H_{24}O_8$.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

IV. Overview of Several Embodiments

It is disclosed herein that melanoma patients exhibit a number of different mutations in PTK family members (see Table 4). In particular, it is demonstrated that ERBB4 is highly mutated in metastatic melanoma. Described herein are novel ERBB4 mutations, which result in expression of ERBB4 protein with increased kinase activity. In addition, cells expressing mutant ERBB4 exhibit transformation capacity. The ERBB4 mutations disclosed herein also activate the PI3K/AKT pathway.

Provided herein is a method of predicting the prognosis of a subject diagnosed with melanoma, comprising detecting the presence or absence of a mutation in the ERBB4 gene, wherein the presence of a mutation in the ERBB4 gene predicts a poor prognosis. A poor prognosis refers to any negative clinical outcome. For example, in some embodiments, a poor prognosis is an increase in the likelihood of death. In some embodiments, a poor prognosis is an increase in the likelihood of metastasis of the melanoma.

Further provided is a method of selecting a subject diagnosed with melanoma as a candidate for treatment with an ERBB4 inhibitor, a PI3K/AKT pathway inhibitor, or both, comprising detecting the presence or absence of a mutation in the ERBB4 gene, wherein the presence of a mutation in the ERBB4 gene indicates that the subject is a candidate for treatment with an ERBB4 inhibitor, a PI3K/AKT pathway inhibitor, or both.

In particular examples, the ERBB4 mutation is selected from G949A, G1354A, G1624A, C1630T, G1687A, G2506A and G2614A (numbered with reference to SEQ ID NO: 1).

In some embodiments, the method further comprises administering to the subject an ERBB4 inhibitor, a PI3K/AKT pathway inhibitor, or both. In some examples, the ERBB4 inhibitor is lapatinib. Agents that decrease expression or activity of ERBB4 or a member of the PI3K/AKT pathway (such as, but not limited to, AKT or PI3K) are known in the art, some of which are described herein.

In some embodiments of the methods, the ERBB4 mutation results in an increase in kinase activity of the ERBB4 protein. In particular examples, the ERBB4 mutation introduces an amino acid change selected from E317K, E452K, E542K, R544W, E563K, E836K and E872K (numbered with reference to SEQ ID NO: 2).

Methods of detecting mutations in a gene are well known in the art. Detection of one or more mutations in the ERBB4 gene can be accomplished using any suitable technique, such as those described in detail in the sections below. For example, ERBB4-specific primers can be used to amplify ERBB4 nucleic acid from a biological sample (such as a tumor tissue sample or blood sample). The amplified molecule can then be sequenced and compared to a reference ERBB4 sequence (such as SEQ ID NO: 1), or compared with ERBB4 from a control sample such as a non-cancerous tissue sample, to detect a mutation in ERBB4. ERBB4 amplification primers and sequencing primers can be designed according to well known methods. Examples of ERBB4 primers are provided in Table 1 and Table 3 (SEQ ID NOs: 3-60 and 64-77). Mutations in ERBB4 can also be detected using oligonucleotides that specifically hybridize with a particular mutation. Hybridization of such oligonucleotides can be detected by labeling the oligonucleotide with a detectable marker, such as a fluorescent marker, enzymatic marker or radioisotope.

For detection of ERBB4 mutations, nucleic acid (such as DNA or RNA) can be isolated from a biological sample according to well known methods. In some embodiments, the biological sample is tissue sample, such as a tumor tissue sample. In other embodiments, the biological sample is a fluid sample, such as blood. For example, nucleic acid can be isolated from cells obtained from a blood sample. In some embodiments, the biological sample is obtained from a patient diagnosed with melanoma. In some embodiments, the biological sample is obtained from a control subject.

Also provided is a method of identifying a therapeutic agent for the treatment of a subject diagnosed with melanoma, comprising screening candidate agents to select an agent that decreases activity (such as kinase activity) of ERBB4, thereby identifying a therapeutic agent for the treatment of a subject with melanoma. In particular examples, the ERBB4 mutation is selected from G949A, G1354A, G1624A, C1630T, G1687A, G2506A and G2614A (numbered with reference to SEQ ID NO: 1).

In some embodiments, the candidate agent is a small molecule, polypeptide (such as an antibody) or nucleic acid molecule (such as an antisense compound, including antisense oligonucleotides, siRNAs or ribozymes). In some examples, screening comprises contacting the candidate agents with cells expressing ERBB4. In some embodiments, the cells express WT ERBB4. In other embodiments, the cells express ERBB4 protein comprising a mutation selected from E317K, E452K, E542K, R544W, E563K, E836K and E872K (numbered with reference to SEQ ID NO: 2). In some embodiments, the therapeutic agent increases kinase activity of ERBB4 at least 2-fold, at least 3-fold, at least 4-fold or at least 5-fold relative to untreated cells.

Further provided is a method of identifying a therapeutic agent for the treatment of a subject diagnosed with melanoma, comprising screening candidate agents to select an agent that decreases expression or activity of a member of the PI3K/AKT pathway, thereby identifying a therapeutic agent for the treatment of a subject with melanoma. In some cases, the agent decreases activity of AKT, such as by reducing phosphorylation of AKT. In some embodiments, the candidate agent is a small molecule, polypeptide (such as an antibody) or nucleic acid molecule (such as an antisense compound, including antisense oligonucleotides, siRNAs or ribozymes).

Further provided herein are oligonucleotides that specifically hybridize with an ERBB4 nucleic acid molecule, wherein the ERBB4 nucleic acid molecule comprises a mutation selected from G949A, G1354A, G1624A, C1630T, G1687A, G2506A and G2614A (numbered with reference to SEQ ID NO: 1). In some embodiments, the oligonucleotide is about 15 to about 40 nucleotides in length. In some embodiments, the oligonucleotide comprises a label, such as, but not limited to a fluorescent label, an enzymatic label or a radioisotope.

Also provided are arrays comprising one or more oligonucleotides that specifically hybridize with an ERBB4 nucleic acid molecule, wherein the ERBB4 nucleic acid molecule comprises a mutation selected from G949A, G1354A, G1624A, C1630T, G1687A, G2506A and G2614A (numbered with reference to SEQ ID NO: 1). In some embodiments, the array is a microarray.

V. Methods of Detecting ERBB4 Mutations

Disclosed herein is the identification of novel mutations in ERBB4, which result in expression of ERBB4 protein with enhanced kinase activity. Seven mutations in human ERBB4 were identified, including G949A, G1354A, G1624A, C1630T, G1687A, G2506A and G2614A (numbered with reference to SEQ ID NO: 1).

Detecting mutations in ERBB4 can be accomplished using any technique known in the art. For example, the presence or absence of an ERBB4 mutation can be determined by conventional methods such as gene or RNA detection methods (for example, DNA sequencing, oligonucleotide hybridization, polymerase chain reaction (PCR) amplification with primers specific to the mutation), or protein detection methods (for example, immunoassays or biochemical assays to identify a mutated ERBB4 protein, such as an ERBB4 with decreased kinase activity or increased cell migration capacity). Generally, the nucleic acid sequence of the ERBB4 gene or RNA in a sample can be detected by any suitable method or technique of detecting gene sequence. Such methods include, but are not limited to, PCR, reverse transcriptase-PCR(RT-PCR), in situ PCR, in situ hybridization, Southern blot, Northern blot, sequence analysis, microarray analysis, or other DNA/RNA hybridization platforms.

Detection of point mutations in target nucleic acids can be accomplished by molecular cloning of the target nucleic acid molecules and sequencing the nucleic acid molecules using techniques well known in the art. Alternatively, amplification techniques such as PCR can be used to amplify target nucleic acid sequences directly from a genomic DNA preparation from a tumor tissue or cell sample. The nucleic acid sequence of the amplified molecules can then be determined to identify mutations. Representative primer pairs that can be used to amplify ERBB4 nucleic acid from a biological sample are provided in Tables 1 and 3 (SEQ ID NOs: 3-60 and 64-77). However, design and selection of appropriate primers is well within the abilities of one of ordinary skill in the art.

The ligase chain reaction (Wu et al., *Genomics* 4:560-569, 1989) and allele-specific PCR (Ruano and Kidd, *Nucleic Acids Res.* 17:8392, 1989) can also be used to amplify target nucleic acid sequences. Amplification by allele-specific PCR uses primers that hybridize at their 3' ends to a particular target nucleic acid mutation. If the particular mutation is not present, an amplification product is not observed. Amplification Refractory Mutation System can also be used to detect mutations in nucleic acid sequences (U.S. Pat. No. 5,595,890; Newton et al., *Nucleic Acids Res.* 17:2503-2516, 1989). Insertions and deletions of genes can also be detected by cloning, sequencing and amplification. In addition, restriction fragment length polymorphism probes for the gene or surrounding marker genes can be used to score alteration of an allele or an insertion in a polymorphic fragment. Single stranded conformation polymorphism analysis can also be used to detect base change variants of an allele (Orita et al., *Proc. Natl. Acad. Sci. USA* 86:2766-2770, 1989). Other known techniques for detecting insertions and deletions can also be used with the claimed methods.

Mismatch detection can be used to detect point mutations in a target nucleic acid molecule, such as ERBB4. Mismatches are hybridized nucleic acid duplexes which are not 100% complementary. The lack of total complementarity can be due to deletions, insertions, inversions, substitutions or frameshift mutations. An example of a mismatch cleavage technique is the RNase protection method, which is described in detail in Winter et al. (*Proc. Natl. Acad. Sci. USA* 82:7575-7579, 1985) and Myers et al. (*Science* 230:1242-1246, 1985). For example, detection of mutations in ERBB4 can involve the use of a labeled riboprobe that is complementary to wild-type ERBB4. The riboprobe and nucleic acid molecule to be tested (for example, obtained from a tumor sample) are annealed (hybridized) together and subsequently digested with the enzyme RNase A, which is able to detect mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the target nucleic acid mRNA or gene, but can a portion of the target nucleic acid, provided it encompasses the position suspected of being mutated. If the riboprobe comprises only a segment of the target nucleic acid mRNA or gene, it may be desirable to use a number of these probes to screen the whole target nucleic acid sequence for mismatches if desired.

In a similar manner, DNA probes can be used to detect mismatches, for example through enzymatic or chemical cleavage (Cotton et al., *Proc. Natl. Acad. Sci. USA* 85: 4397-4401, 1988; Shenk et al., *Proc. Natl. Acad. Sci. USA* 72:989-993, 1975). Alternatively, mismatches can be detected by shifts in the electrophoretic mobility of mismatched duplexes relative to matched duplexes (Cariello, *Am. J. Hum. Genet.* 42:726-734, 1988). With either riboprobes or DNA probes, the target nucleic acid mRNA or DNA which may contain a mutation can be amplified before hybridization. Changes in target nucleic acid DNA can also be detected using Southern hybridization, especially if the changes are gross rearrangements, such as deletions and insertions.

Amplified nucleic acid sequences can also be screened using allele-specific probes. These probes are nucleic acid oligomers, each of which contains a region of the target nucleic acid gene harboring a known mutation. For example, one oligomer may be about 30 nucleotides in length, corresponding to a portion of the target gene sequence. By use of a battery of such allele-specific probes, target nucleic acid amplification products can be screened to identify the presence of a previously identified mutation in the target gene. Hybridization of allele-specific probes with amplified target nucleic acid sequences can be performed, for example, on a nylon filter. Hybridization to a particular probe under stringent hybridization conditions indicates the presence of the same mutation in the tumor tissue as in the allele-specific probe.

The ERBB4 primer pairs disclosed herein are useful for determination of the nucleotide sequence of a target nucleic acid using nucleic acid amplification techniques such as the polymerase chain reaction. The pairs of single stranded DNA primers can be annealed to sequences within or surrounding the target nucleic acid sequence in order to prime amplification of the target sequence. Allele-specific primers can also be used. Such primers anneal only to particular mutant target sequence, and thus will only amplify a product in the presence of the mutant target sequence as a template. In order to facilitate subsequent cloning of amplified sequences, primers may have restriction enzyme site sequences appended to their ends. Such enzymes and sites are well known in the art. The primers themselves can be synthesized using techniques which are well known in the art. Generally, the primers can be made using oligonucleotide synthesizing machines which are commercially available. Design of particular primers is well within the skill of the art.

Nucleic acid probes that hybridize with an ERBB4 nucleic acid molecule, such as a wild-type ERBB4 nucleic acid molecule or a mutant ERBB4 nucleic acid molecule described herein, are useful for a number of purposes. They can be used in Southern hybridization to genomic DNA and in RNase protection assays for detecting point mutations. The probes can also be used to detect target nucleic acid amplification products. ERBB4 probes can also be used to detect mismatches with the wild type gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids (Novack et al., *Proc. Natl. Acad. Sci. USA* 83:586, 1986).

Mutations in nucleic acid molecules can also be detected by screening for alteration of the corresponding protein. For example, monoclonal antibodies immunoreactive with a target gene product can be used to screen a tissue, for example an antibody that is known to bind to a particular mutated position of the gene product (protein). For example, a suitable antibody may be one that binds to a deleted exon or that binds to a conformational epitope comprising a deleted portion of the target protein. Lack of cognate antigen would indicate a mutation. Such immunological assays can be accomplished using any convenient format known in the art, such as Western blot, immunohistochemical assay and enzyme-linked immunosorbent assay (ELISA). In some embodiments, the ERBB4 amino acid mutation is selected from E317K, E452K, E542K, R544W, E563K, E836K and E872K (numbered with reference to SEQ ID NO: 2).

VI. Arrays

In particular embodiments provided herein, arrays can be used to evaluate the presence or absence of mutations in ERBB4. In some examples, the array comprises an oligonucleotide that specifically hybridizes with an ERBB4 nucleic acid molecule comprising a mutation selection from G949A, G1354A, G1624A, C1630T, G1687A, G2506A and G2614A (numbered with reference to SEQ ID NO: 1). Oligonucleotides that specifically hybridize with an ERBB4 nucleic acid comprising a mutation do not hybridize to WT ERBB4, or hybridization of the oligonucleotide to WT ERBB4 is significantly weaker than hybridization to the mutant ERBB4. In some embodiments the array comprises two or more oligonucleotides that specifically hybridize with an ERBB4 nucleic acid comprising a mutation selected from G949A, G1354A, G1624A, C1630T, G1687A, G2506A and G2614A (numbered with reference to SEQ ID NO: 1). In other embodiments, the array comprises oligonucleotides that specifically hybridize with ERBB4 nucleic acid molecules comprising each mutation of G949A, G1354A, G1624A, C1630T, G1687A, G2506A and G2614A (numbered with reference to SEQ ID NO: 1). In some examples, the array further comprises other oligonucleotides, such as control oligonucleotides or oligonucleotides that specifically hybridize with WT ERBB4 or other mutant ERBB4 nucleic acid molecules. Exemplary control oligonucleotide probes include GAPDH, actin, and YWHAZ.

The oligonucleotide probes can further include one or more detectable labels, to permit detection of hybridization signals between the probe and target sequence (such as one of the mutant ERBB4 nucleic acid molecules).

Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides are not amenable to non-specific binding, or when non-specific binding occurs, such materials can be readily removed from the surface without removing the oligonucleotides.

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit low background fluorescence.

The array formats of the present disclosure can be included in a variety of different types of formats. A "format" includes any format to which the solid support can be affixed, such as microtiter plates (e.g. multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides to a solid support and for directly synthesizing the oligonucleotides onto the support are known to those working in the field; a summary of suitable methods can be found in Matson et al. (*Anal. Biochem.* 217:306-10, 1994). In one example, the oligonucleotides are synthesized onto the support using conventional chemical techniques for preparing oligonucleotides on solid supports (such as see International application publications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second)(2° set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

VII. Use of ERBB4 for Prognosis and Therapy

It is disclosed herein that ERBB4 is highly mutated in melanoma tumors. The disclosed ERBB4 somatic mutations result in increased ERBB4 kinase activity, transformation capacity and anchorage-independent growth. The high frequency of mutations identified in ERBB4, their co-localization, and the identification of two identical missense mutations (E452K and E872K) in multiple MM samples indicates these mutations play a role in tumorigenesis. In addition, the ERBB4 mutations disclosed herein exhibit ligand-independent basal phosphorylation, providing evidence that these mutations are oncogenic. Accordingly, the identified mutations in ERBB4 predict a poor prognosis for patients with melanoma. In some embodiments, a poor prognosis is an increase in the likelihood of death. In some embodiments, a poor prognosis is an increase in metastasis.

The detection of one or more ERBB4 mutations selected from G949A, G1354A, G1624A, C1630T, G1687A, G2506A and G2614A (numbered with reference to SEQ ID NO: 1) can be used as a clinical tool to determine the prognosis of a patient with melanoma. Since these mutations are oncogenic and play a role in tumorigenesis of MM, a poor prognosis is indicated when one or more of the mutations is detected in a sample from a subject diagnosed with melanoma. Detection of one or more of these mutations can also be used as a tool for determining an appropriate therapy for a subject with melanoma. The presence of one or more of these mutations indicates the subject is a candidate for treatment with a kinase inhibitor, such an EGFR family inhibitor, or more particularly, an ERBB4-specific inhibitor. In some examples, the ERBB4 mutation introduces an amino acid change selected from E317K, E452K, E542K, R544W, E563K, E836K and E872K (numbered with reference to SEQ ID NO: 2).

It is also disclosed herein that mutations in ERBB4 activate the PI3K/AKT pathway, as indicated by increased phosphorylation of AKT in melanoma cells harboring the disclosed ERBB4 mutations. Thus, the presence of one or more ERBB4 mutations indicates the subject is a candidate for treatment with an inhibitor of the PI3K/AKT pathway, such as an inhibitor of PI3K or AKT. In some embodiments, the method of selecting a patient as a candidate for treatment with an ERBB4 and/or PI3K/AKT pathway inhibitor further includes treating the subject with an ERBB4 inhibitor, a PI3K/AKT pathway inhibitor, or both.

The finding that the presence of prognosis-associated ERBB4 mutations selected from G949A, G1354A, G1624A, C1630T, G1687A, G2506A and G2614A (numbered with reference to SEQ ID NO: 1) result in an increase in kinase activity, transformation capacity and/or anchorage-independent growth indicates that compounds that inhibit (such as decrease kinase activity of) ERBB4 will be useful as therapeutic agents for the treatment of melanoma. Thus, provided herein is a method of identifying therapeutic agents for the treatment of melanoma, comprising screening candidate agents to select an agent that inhibits activity (such as kinase activity) or expression of ERBB4.

In some embodiments, screening comprises contacting the candidate agents with cells that express ERBB4 and detecting any change in activity or expression of ERBB4. The ERBB4 expressing cells can be primary cells obtained from a subject diagnosed with melanoma, immortalized or transformed cells obtained from a melanoma patient, or the cells can be commercially available immortalized cell lines. In some embodiments, the cells express wild-type ERBB4. In other embodiments, the cells express mutant ERBB4, such as ERBB4 with a mutation selection from G949A, G1354A, G1624A, C1630T, G1687A, G2506A and G2614A (numbered with reference to SEQ ID NO: 1). In some examples, a cell line is transfected with an expression vector encoding wild-type or mutant ERBB4. In other examples, primary tumor cells expressing mutant ERBB4 are evaluated. In either case, the cells are either untreated or treated with a candidate agent and ERBB4 kinase activity is measured, for example by incorporation of radiolabeled ATP. A decrease in ERBB4 activity in the treated cells, compared to the untreated cells, indicates the candidate agent is a therapeutic agent for melanoma.

In some embodiments, a decrease in kinase activity of ERBB4 following treatment with the candidate agent identifies the agent as a therapeutic agent for the treatment of melanoma. In some embodiments, the therapeutic agent decreases kinase activity of ERBB4 at least 2-fold, at least 3-fold, at least 4-fold or at least 5-fold relative to untreated cells. Methods of screening candidate agents to identify therapeutic agents for the treatment of disease are well known in the art. In one embodiment, screening comprises a high-throughput screen. In another embodiment, candidate agents are screened individually.

Given the finding that mutations in ERBB4 result in activation of the PI3K/AKT pathway, provided herein is a method of identifying therapeutic agents for the treatment of melanoma, comprising screening candidate agents to select an agent that inhibits activity or expression of a member of the PI3K/AKT pathway, such as PI3K or AKT. In some embodiments, screening comprises contacting the candidate agents with cells that express mutant ERBB4 and detecting any change in activity or expression of a member of the PI3K/AKT pathway. The mutant ERBB4 expressing cells can be primary cells obtained from a subject diagnosed with melanoma, immortalized or transformed cells obtained from a melanoma patient, or the cells can be commercially available immortalized cell lines. In some embodiments, the cells express ERBB4 with a mutation selection from G949A, G1354A, G1624A, C1630T, G1687A, G2506A and G2614A (numbered with reference to SEQ ID NO: 1). In some examples, a cell line is transfected with an expression vector encoding mutant ERBB4. In other examples, primary tumor cells expressing mutant ERBB4 are evaluated. In either case, the cells are either untreated or treated with a candidate agent and PI3K/AKT activity is measured. In some examples, PI3K/AKT activity is measured by detecting the level of AKT phosphorylation. A decrease in PI3K/AKT activity in the treated cells, compared to the untreated cells, indicates the candidate agent is a therapeutic agent for melanoma.

The candidate agents can be any type of molecule, such as, but not limited to nucleic acid molecules, proteins, polypeptides, antibodies, lipids, small molecules, chemicals, cytokines, chemokines, hormones, or any other type of molecule that may alter ERBB4 or PI3K/AKT activity either directly or indirectly. In some embodiments, the candidate agents are small molecules, polypeptides (such as antibodies) or nucleic acid molecules (such as antisense compounds, including antisense oligonucleotides, siRNAs or ribozymes).

The following examples are provided to illustrate certain particular features and/or embodiments. These examples should not be construed to limit the disclosure to the particular features or embodiments described.

EXAMPLES

Example 1

Experimental Procedures

This example describes the materials and methods used for the experiments described in Examples 2-6.

Amplification, Sequencing and Mutational Analysis of ERBB4

Metastatic melanoma samples and their matched normal samples were obtained according to standard procedures. Genomic DNA was isolated using DNeasy™ Blood & Tissue kit (Qiagen, Valencia, Calif.). For all samples, matching between germline and tumor DNA was verified by direct sequencing of 26 single nucleotide polymorphisms (SNPs) at 24 loci. The tissue and melanoma cell lines used in the Examples below are also described in Palavalli et al. (*Nat. Genet.* 41:518-520, 2009).

PCR and sequencing primers were designed using Primer 3 (available online at frodo.wi.mit.edu/cgi-bin/primer3/primer3_www.cgi) and synthesized by Invitrogen (Carlsbad, Calif.). The primers used for PCR amplification of the whole coding region of ERBB4 are shown in Table 1 (CCDS accession CCDS2394.1; GenBank Accession No. NM_005235; SEQ ID NO: 1). The coding region of ERBB4 was sequenced using a primer with the following sequence: GTAAAAC-GACGGCCAGT (SEQ ID NO: 61). PCR amplification, sequencing and analysis were performed as previously described (Samuels et al., *Science* 304:554, 2004). Briefly, PCR products were purified using exonuclease (Epicentre Biotechnologies, Madison, Wis.) and shrimp alkaline phosphatase (USB Corporation, Cleveland, Ohio). Products were purified with rehydrated Sephadex™ 4 G-50 powder (GE Healthcare, Piscataway, N.J.) and cycle sequencing was carried out using BigDye Terminator™ v3.1 Cycle Sequencing kit (Applied Biosystems, Foster City, Calif.). Sequence data was collected on an ABI3730xl (Applied Biosystems, Foster City, Calif.).

The kinase domain mutation screen was analyzed using Consed (Gordon et al., *Genome Res.* 8(3):195-202, 1998). Variants were called using Polyphred 6.11 (Bhangale et al., *Nat. Genet.* 38(12):1457-1462, 2006) and DIPDetector, an indel detector for improved sensitivity in finding insertions and deletions.

Sequence traces of the secondary screen were analyzed using the Mutation Surveyor software package (SoftGenetics, State College, Pa.).

TABLE 1

Primers used for PCR amplification of the ERBB4 coding region

| ERBB4 Exon | Forward Primer | SEQ ID NO: | Reverse Primer | SEQ ID NO: |
|---|---|---|---|---|
| Exon 1 | GGAAATAGCTGCACAGTCCG | 3 | GTAAAACGACGGCCAGTATGGGTGAAGAGGGCAGG | 32 |
| Exon 2 | AGAACTGGGATAGGCTTGTGG | 4 | GTAAAACGACGGCCAGTTTCCAGGTATCAGCACACAGG | 33 |
| Exon 3 | GTAAAACGACGGCCAGTAAGCCAATTCTTTAGAATATGATATGG | 5 | TGCCTTAGAGTGTTCCTCAATG | 34 |
| Exon 4 | TCTTGGCTATTAGCAACATGACTC | 6 | GTAAAACGACGGCCAGTCAATGAATGCAATCAAAGTTCAA | 35 |
| Exon 5 | GTAAAACGACGGCCAGTAAATCCTCATAAAGGAGCAGGAG | 7 | CCAAAGCAAATCAACCACAAG | 36 |
| Exon 6 | GTAAAACGACGGCCAGTTGAATTGAGTCAAAGACAGGGTG | 8 | GGAATGACTTTGAGGAGGGC | 37 |
| Exon 7 | TTTGGAAACACACATGACTCTTAAA | 9 | GTAAAACGACGGCCAGTTTTGCTATGAAACTTTACACAAATCA | 38 |
| Exon 8 | GTGGAGCAGTAACCAAGCAAG | 10 | GTAAAACGACGGCCAGTGTGTGGGTAGGTTTGGTTGTG | 39 |
| Exon 9 | AAAGCAGAACCAGTAGTGAATGTTG | 11 | GTAAAACGACGGCCAGTGGTGAAACTCTTCAGCTTCCAG | 40 |
| Exon 10 | GTAAAACGACGGCCAGTCCTCCTCCACATCTAGCACAG | 12 | TCTCCTGACCTCATGATCCAC | 41 |
| Exon 11 | GTAAAACGACGGCCAGTCCTTTCTCACTTCCCAACTTTC | 13 | TACCTCACACCATCATCGGAG | 42 |

TABLE 1-continued

Primers used for PCR amplification of the ERBB4 coding region

| ERBB4 Exon | Forward Primer | SEQ ID NO: | Reverse Primer | SEQ ID NO: |
|---|---|---|---|---|
| Exon 12 | GTAAAACGACGGCCAGTTTGATTCAGTTTCCATTTATACACCA | 14 | GAGCAACAATTCTGACCGGAT | 43 |
| Exon 13 | GTAAAACGACGGCCAGTTAGGCCACCAAAGTCATTTGC | 15 | GAATGGCGTGAACCCAGG | 44 |
| Exon 14 | GTAAAACGACGGCCAGTTGATGCTCCTGGCACATAGAG | 16 | CCCATGGCATCCTGTAAGTAG | 45 |
| Exon 15 | TCTTAGAGGAAGATTTGCCACC | 17 | GTAAAACGACGGCCAGTCATTTCAGAGATGGTACCAGGG | 46 |
| Exon 16 | GCTTCCCATGTTCTTCCTCC | 18 | GTAAAACGACGGCCAGTAAGTAAGAAAGTTGGCTTGAGAAGG | 47 |
| Exon 17 | TGTGGATAATGTCTTGTACAACTGC | 19 | GTAAAACGACGGCCAGTTTCACAAGCTTTGTTTAACGGAC | 48 |
| Exon 18 | GGTTGTCAAGGCAAACCAAG | 20 | GTAAAACGACGGCCAGTAGACTGTATCCGTCCCAGCTC | 49 |
| Exon 19 | AAGCAGACAACAAAGTTGCAGAG | 21 | GTAAAACGACGGCCAGTTCTAGGCAGACAGTTGTGAAGC | 50 |
| Exon 20 | GTAAAACGACGGCCAGTTCAGCACCATTAGTACAATCCAA | 22 | TTTGGCACCTAGTCAATTCAA | 51 |
| Exon 21 | GTAAAACGACGGCCAGTGCACTTCCAACTGAAGGCTAAG | 23 | AGGCAAATGGTAGAACCAAGG | 52 |
| Exon 22 | GTAAAACGACGGCCAGTAGGCCAGCCCAAAGACTC | 24 | TAACTGCTTTAGGAAATTAGGCTTATC | 53 |
| Exon 23 | TGATTGGTGTTTGGATTGACC | 25 | GTAAAACGACGGCCAGTCAAAGAGGCGTTCATATGTTCC | 54 |
| Exon 24 | GTAAAACGACGGCCAGTGAGTCGTTTCTTTCACTAGCTTGC | 26 | TGTTTGTGGTCCTTTCCACAG | 55 |
| Exon 25 | TAGGTTTCTTAATGGCCGGTG | 27 | GTAAAACGACGGCCAGTGGCATCACATTGATTTGAGCTA | 56 |
| Exon 26 | TGCTTAGGAAGCTTCACTGTTG | 28 | GTAAAACGACGGCCAGTTAACTCACTGTTGGCAAAGGC | 57 |
| Exon 27 | TGGCTTTGATATCCTTGTGGC | 29 | GTAAAACGACGGCCAGTCAGCTATCTGGCAATTTCTATTCTG | 58 |
| Exon 28 | CCATATGCAGAAGAGACAAATGC | 30 | GTAAAACGACGGCCAGTAGGTAGTCTGGGTGCTGAAGG | 59 |
| Exon 28 | TGAATCCAGTGGAGGAGAACC | 31 | GTAAAACGACGGCCAGTGACCACCAGAGAAAGAGAGGG | 60 |

Construction of Wild-Type and Mutant ERBB4 Expression Vectors

Human ERBB4 (GenBank Accession No. NM_005235; SEQ ID NO: 1) was cloned by PCR using PHUSION™ Hot Start High-Fidelity DNA Polymerase (New England Biolabs, Inc., Ipswich, Mass.) using a clone purchased from Open Biosystems (clone ID #8327667) and cloned with the following primers:

```
CGGCTCTAGAGCCACCATGAAGCCGGCGAC     (SEQ ID NO: 62)

ATCGGCGGCCGCTTACACCACAGTATTCCGG    (SEQ ID NO: 63)
```

The PCR product was cloned into the mammalian expression vector pCDF-MCS2-EF1-Puro™ (Systems Biosciences, Inc., Mountain View, Calif.) via the XbaI and NotI restriction sites. The E317K, E452K, E542K, R544W, E563K, K751M, E836K, and E872K point mutants were made using Fusion PCR for site-directed mutagenesis.

Cell Culture and Transient Expression

Metastatic melanoma tumor lines were maintained according to standard methods (see Chappell et al., Cancer Res. 59:59-62, 1999). HEK 293T cells and NIH 3T3 cells were purchased from the American Type Culture Collection (ATCC) (Manassas, Va.) and maintained in complete Dulbecco's Modified Eagles Medium (DMEM) supplemented with 10% Fetal Bovine Serum (FBS), 1× nonessential amino acids, 2 mM L-glutamine, and 0.75% sodium bicarbonate. HEK 293T cells were transfected with Lipofectamine™ 2000 reagent (Invitrogen, Carlsbad, Calif.) at a 6:1 ratio with DNA (µl:µg) using 3-5 µg of plasmid DNA.

Immunoprecipitation and Western Blotting

Transfected cells were washed 3× in PBS and lysed using 0.5 ml 1% NP-40 lysis buffer (1% NP-40, 50 mM Tris-HCl pH 7.5, 150 mM NaCl, complete protease inhibitor tablet, EDTA-free (Roche, Indianapolis, Ind.), 1 µM sodium orthovanadate, 1 mM sodium fluoride, and 0.1% β-mercaptoethanol) per T-75 flask for 20 minutes on ice. Lysed cells were scraped and transferred into a 1.5 mL microcentrifuge tube. Extracts were centrifuged for 10 minutes at 14,000 rpm at 4° C. Supernatant (450 µl) was immunoprecipitated overnight using 20 µl of anti-ERBB4 agarose-conjugated beads (Santa Cruz Biotechnology, Inc., Santa Cruz, Calif.). The immunoprecipitates were washed and subjected to SDS-PAGE and western blotting according to standard methods (see Samuels et al., Science 304:554, 2004). The primary antibodies used in these experiments were anti-ERBB4 (Santa Cruz Biotechnology, Santa Cruz, Calif.), anti-P-ERBB4 (Y1162) (Abgent, San Diego, Calif.), anti-P-ERBB4 (Y1284) (Cell Signaling, Danvers, Mass.), anti-PY20 (Zymed-Invitrogen), anti-P-ERK1/2 (T202/Y204), anti-ERK1/2, anti-P-AKT (S473), anti-AKT (Cell Signaling), anti-P-STAT5A/B (Y694/Y699) (Upstate Biotech-Millipore), anti-STAT5 (Cell Signaling) and anti-α-tubulin (Calbiochem-EMD Biosciences, Gibbstown, N.J.).

ERBB4-Phosphosite-Specific Antibody Analysis

ERBB4 was immunoprecipitated as described above and subjected to SDS-PAGE. Primary phospho-antibodies were pre-incubated overnight with the relevant competitive phospho-peptides (pPep Y1162-Abgent #BP3122a, pPep Y1284-Cell Signaling #1022). Following blocking/competition, the antibody/peptide mixture was diluted into blocking buffer and western blotting was performed as described above.

Pooled Stable Expression

To make lentivirus, ERBB4 constructs were co-transfected into HEK 293T cells seeded at $1.5 \times 10^6$ per T75 flask with pVSV-G and pFIV-34N helper plasmids (System Biosciences, Mountain View, Calif.) using Lipofectamine™ 2000. Virus-containing conditioned media was harvested 48-60 hours after transfection, filtered, aliquoted and stored at −80° C. ERBB4 lentivirus was used to make SK-Mel-2 and NIH 3T3 stable clones.

SK-Mel-2 cells (National Cancer Institute, Division of Cancer Treatment, Developmental Therapeutics Program, Frederick, Md.) were grown in RPMI-1640 (Lonza, Walkersville, Md.) supplemented with 10% fetal bovine serum (HyClone, Logan, Utah). NIH 3T3 cells were grown in DMEM supplemented with 10% FBS, 2 mM L-glutamine, 1× non-essential amino acids, and 0.75% sodium bicarbonate. Sk-Mel-2 and NIH 3T3 cells were seeded at $1.5 \times 10^6$ cells per T75 flask 24 hours prior to infection. Lentivirus for ERBB4 (WT, E317K, E452K, E542K, R544W, E563K, K751M, E836K, and E872K point mutants) and empty vector control were diluted with equal volume of normal complete medium in the presence of 8 µg/ml polybrene. Cells were incubated for 24 hours in the presence of virus followed by changing of the medium to normal complete medium for an additional 24 hours. Lentivirus-infected cells were then selected for by addition of complete medium containing 3 g/ml puromycin for SK-Mel-2 cells or 2 g/ml puromycin for NIH 3T3 cells and allowed to incubate for 3 days. Stable expression of ERBB4 proteins (WT and mutants) was determined by SDS-PAGE analysis followed by immunoblotting with anti-ERBB4 and anti-tubulin to show equivalent expression among pools.

Lentiviral shRNA

Constructs for stable depletion of ERBB4 were obtained from Open Biosystems (Huntsville, Ala.). Negative control constructs in the same vector system (pLK0.1 vector alone and scrambled shRNA) were obtained from Addgene (Cambridge, Mass.). To prepare transient virus stocks, $1.5 \times 10^6$ HEK 293T cells were plated in T75 flasks. The next day, the cells were co-transfected with shRNA constructs (3 µg), together with pHR'8.2AR and pCMV-VSV-G helper constructs (3 µg and 0.3 µg, respectively), using Lipofectamine™ 2000 (Invitrogen). The media were changed the next day, and the following day, and virus-containing media were harvested. The viral stocks were centrifuged and filtered to remove any non-adherent HEK 293T cells.

Next, MM lines (2T, 7T, 17T, 31T and 63T) were infected with shRNA lentiviruses for each condition (vector and scrambled controls and three independent ERBB4-specific shRNAs). To do this, cells were plated at sub-confluent densities. The next day, cells were infected with a cocktail of 1 ml virus-containing medium, 1 ml regular medium and 8 µg/ml polybrene. The medium was changed one day post-infection, and selective medium was added two days post-infection (2 µg/ml puromycin for all cells). After three days of puromycin selection, the mock-infected cells had all died. Stably infected pooled clones were tested in functional assays.

To rescue shRNA-mediated knock-down of ERBB4 in melanoma cell lines, the non-targetable ERBB4 lentivirus was made as described above and used to infect the melanoma cell line 17T. After infection, cells were given 48 to 72 hours to recover from infection prior to testing in functional assays.

Proliferation and Growth Inhibition Assays

To examine growth potential, melanoma cell lines (2T, 7T, 17T, 31T and 63T) stably infected with either vector or scrambled controls or ERBB4-specific shRNAs were seeded into 96-well plates at 2,500 cells per well and incubated for 13-17 days. Samples were analyzed every 48 hours by lysing cells in 50 µl 0.2% SDS/well and incubating for 2 hours at 37°

C. prior to addition of 150 μl/well of SYBR Green I solution (1:750 SYBR Green I (Invitrogen-Molecular Probes) diluted in dH$_2$O).

The effects of tyrosine kinase inhibitors (TKIs) on the proliferation of melanoma cell lines were tested by seeding 96-well plates at 5,000 cells/well in the presence or absence of serum-containing media and incubated for 24 hours prior to addition of TKIs. Increasing concentrations of lapatinib (Tykerb-GlaxoSmithKline) were added to each well in four replicates with DMSO as negative control. Plates were analyzed 72 hours post-addition of TKIs using the SYBR Green I proliferation assay described above.

To further test TKIs on melanoma cell lines, 96-well plates were seeded at 5,000 cells per well and incubated 24 hours prior to addition of TKIs (e.g. lapatinib) at concentrations from 10 nM to 30 μM. Once inhibitors were added, cells were incubated for 72 hours at 37° C. Cells were then analyzed according to previously described methods (Rusnak et al., *Mol. Cancer Ther.* 1:85-94, 2001). Plates were read at 650 nm on a Molecular Devices (Spectra Max) Plate Reader and analyzed using SoftMax v5 and GraphPad Prism v5.

Soft Agar Assay

SK-Mel-2 pooled ERBB4 clones were plates in duplicate at 1000 cells/well and NIH 3T3 pooled ERBB4 clones were plated in duplicate at 5000 cells/well in top plugs consisting of sterile 0.33% Bacto-Agar (BD, Sparks, Mo.) and 10% FBS (HyClone, Logan, Utah) in a 24-well plate. The lower plug contained sterile 0.5% Bacto-Agar and 10% FBS. After two weeks, the colonies were photographed and counted.

NIH 3T3 Transformation Assay

Each plasmid (150 ng) was transfected into NIH 3T3 cells cultured in 12-well plates by the calcium phosphate precipitation method. Twenty-four hours after transfection, 5% of transfected cells were transferred into T25 flasks and cultured for 10 days in normal growth medium. The cells were stained with Hema3 (Sigma St. Louis, Mo.) and analyzed for the presence of foci.

Analysis of ERBB4 Kinase Activity

HEK 293T cells were transiently transfected with ERBB4 (WT, E317K, E452K, E542K, R544W, E563K, E836K, E872K and kinase-dead K751M) or empty vector and incubated for 18-24 hours at 37° C. in the presence (10%) or absence (0.5%) of serum-containing medium prior to immunoprecipitation. Cells were harvested and approximately 3 mg of lysate was immunoprecipitated as described above and subjected to a kinase assay Immune complexes were washed three times in lysis buffer followed by two washes in kinase buffer (20 mM HEPES pH 7.4, 50 mM NaCl, 3 mM MnCl$_2$, 20 mM MgCl$_2$, 1 mM sodium orthovanadate, 1 mM sodium fluoride, and 1× complete protease inhibitor tablet) Immune complexes were resuspended in 50 μl kinase buffer and 10 μl was incubated in the presence of [γ-$^{32}$P]ATP (3 μCi per reaction) for 15 minutes at 37° C. Kinase reactions were stopped by the addition of 2×SDS sample buffer and phosphorylated samples were resolved on 8% tris-glycine gels. Gels were fixed in a 50% methanol/7% acetic acid solution, washed three times in dH$_2$O then stained for 1 hour in GelCode™ Blue stain (Pierce) followed by destaining for an additional hour. Gels were dried prior to autoradiography.

Immunoblot Quantitation Analysis

Scanned films from western blot analysis of SDS-PAGE were analyzed using ImageJ (NIH software). Individual bands were quantitated and plots were generated to determine the intensities in each band. The data was then exported to Microsoft Excel and analyzed further for phospho:total ratios of protein.

Flow Cytometry Analysis

Melanoma cells were seeded into T-25 flasks at densities of 3×10$^5$ cells per flask in normal complete T2 medium and incubated at 37° C. for 24 hours prior to addition of lapatinib. Lapatinib or vehicle was added for 72 hours at a concentration of 5 μM. Cells were then harvested for FACS analysis by first removing the medium into a new conical tube followed by trypsinization of attached cells in T-25 flasks. Trypsinized cells and those from the medium were combined and washed in ice-cold PBS. Cells were collected by centrifugation at 1,000 rpm at 4° C. Ice-cold 70% ethanol was added to cell pellets and allowed to fix overnight at 4° C. followed by washing in ice-cold PBS. DNase-free RNase (Roche) was added to cells resuspended in 0.5-1 ml PBS and incubated at 37° C. for 30 minutes before adding 50-100 μl of propidium iodide (PI-0.5 mg/ml) (Roche). Cellular DNA content was analyzed on Becton Dickinson FACSCalibur™ using CellQuest™ software.

X-Ray Crystal Structure Assembly

The X-ray crystal structures of the ERBB4 extracellular and kinase domains were used as templates in the program SWISS-MODEL (Guex and Peitsch, *Electrophoresis* 18:2714-2723, 1997). Location of EGFR and ERBB2 mutations in the crystal were found by aligning the protein sequences for EGFR, ERBB2, ERBB3, and ERBB4 using ClustalW (Guex and Peitsch, *Electrophoresis* 18:2714-2723, 1997). Previously identified mutations in EGFR and ERBB2 were matched to the sequence of ERBB4 using the ClustalW alignment.

Statistical Analysis

To determine whether the ratio of nonsynonymous to synonymous mutations observed was statistically significant, the exact binomial test was used, with an expected ratio of 2.5:1. All the statistical calculations were performed in the R statistical environment (available online on the World Wide Web at r-project.org) (Sjoblom et al., *Science* 314:268-274, 2006). Further statistical analyses were performed using Microsoft Excel to generate p-values to determine significance (two-tailed t-test) Inhibition curves (IC$_{50}$) were analyzed and plotted using GraphPad Prism v5.

Example 2

High-Throughput DNA Sequence Analysis of the PTK Family in MM

This example describes the identification of somatic mutations in members of the PTK family, including ERBB4, in patients with melanoma. Kinase mutations have been previously identified by sequencing genes encoding these domains (Bardelli et al., *Science* 300:949, 2003; Davies et al., *Nature* 417(6892):949-954, 2002; Greenman et al., *Nature* 446:153-158, 2007; Samuels et al., *Science* 304:554, 2004). Thus, PTKs were evaluated herein to determine if they are genetically altered in MM. Initially, the kinase domain coding exons of this gene superfamily were analyzed in 29 mM samples (Table 2). A total of 593 exons were extracted from genomic databases. These exons were amplified by polymerase chain reaction (PCR) from cancer genomic DNA samples using the primers listed in Table 1 and directly sequenced with dye terminator chemistry.

TABLE 2

Tyrosine Kinase genes analyzed

| CCDS accession and amplimer number | Ref Seq accession and amplimer number | Gene Name | Gene Description |
|---|---|---|---|
| CCDS35165.1 | NM_007313.2 | ABL1/ABL | v-abl Abelson murine leukemia viral oncogene homolog 1 |
| CCDS30947.1 | NM_007314.2 | ABL2/ARG | v-abl Abelson murine leukemia viral oncogene homolog 2 (arg, Abelson-related gene) |
| CCDS33928.1 | NM_005781.4 | ACK1/TNK2 | tyrosine kinase, non-receptor, 2 |
| CCDS33172.1 | NM_004304.3 | ALK | anaplastic lymphoma kinase (Ki-1) |
| CCDS12575.1 | NM_021913.3 | AXL | AXL receptor tyrosine kinase |
| CCDS5982.1 | NM_001715.2 | BLK | B lymphoid tyrosine kinase |
| CCDS14168.1 | NM_203281.2 | BMX | BMX non-receptor tyrosine kinase |
| CCDS13524.1 | NM_005975.2 | BRK/PTK6 | PTK6 protein tyrosine kinase 6 |
| CCDS14482.1 | NM_000061.1 | BTK | Bruton agammaglobulinemia tyrosine kinase |
| CCDS4302.1 | NM_005211.2 | CSF1R | colony stimulating factor 1 receptor, formerly McDonough feline sarcoma viral (v-fms) oncogene homolog |
| CCDS10269.1 | NM_004383.1 | CSK | c-src tyrosine kinase |
| CCDS4690.1 | NM_001954.4 | DDR1 | discoidin domain receptor family, member 1 |
| CCDS1241.1 | NM_006182.2 | DDR2 | discoidin domain receptor family, member 2 |
| CCDS5514.1 | NM_005228.3 | EGFR | epidermal growth factor receptor (erythroblastic leukemia viral (v-erb-b) oncogene homolog, avian) |
| CCDS5884.1 | NM_005232.3 | EPHA1 | ephrin receptor EphA1 |
| CCDS169.1 | NM_004431.2 | EPHA2 | ephrin receptor EphA2 |
| CCDS2922.1 | NM_005233.5 | EPHA3 | ephrin receptor EphA3 isoform a precursor |
| CCDS2447.1 | NM_004438.3 | EPHA4 | ephrin receptor EphA4 |
| CCDS3514.1 | NM_182472.1 | EPHA5 | ephrin receptor EphA5 isoform b |
| N/A | NM_001080448.2 | EPHA6 | EPH receptor A6 isoform a |
| CCDS5031.1 | NM_004440.2 | EPHA7 | ephrin receptor EphA7 |
| CCDS30626.1 | NM_001006943.1 | EPHA8 | EPH receptor A8 isoform 2 precursor |
| CCDS425.1 | NM_173641.2 | EPHA10 | EPH receptor A10 isoform 2 |
| N/A | NM_004441.3 | EPHB1 | ephrin receptor EphB1 precursor |
| CCDS230.1 | NM_004442.6 | EPHB2 | ephrin receptor EphB2 isoform 2 precursor |
| CCDS3268.1 | NM_004443.3 | EPHB3 | ephrin receptor EphB3 precursor |
| CCDS5706.1 | NM_004444.4 | EPHB4 | ephrin receptor EphB4 precursor |
| CCDS5873.1 | NM_004445.2 | EPHB6 | ephrin receptor EphB6 precursor |
| CCDS32642.1 | NM_004448.2 | ERBB2 | v-erb-b2 erythroblastic leukemia viral oncogene homolog 2, neuro/glioblastoma derived oncogene homolog (avian) |
| CCDS31833.1 | NM_001982.2 | ERBB3 | v-erb-b2 erythroblastic leukemia viral oncogene homolog 3 (avian) |
| CCDS2394.1 | NM_005235.2 | ERBB4 | v-erb-a erythroblastic leukemia viral oncogene homolog 4 (avian) |
| CCDS6381.1 | NM_153831.2 | FAK/PTK2 | PTK2 protein tyrosine kinase 2 |
| CCDS4098.1 | NM_005246.2 | FER | fer (fps/fes related) tyrosine kinase (phosphoprotein NCP94) |
| CCDS10365.1 | NM_002005.2 | FES | V-FES feline sarcoma viral/V-FPS fujinami avian |
| CCDS6107.1 | NM_023110.2 | FGFR1 | fibroblast growth factor receptor 1 (fms-related tyrosine kinase 2, Pfeiffer syndrome) |
| CCDS31298.1 | NM_000141.3 | FGFR2 | fibroblast growth factor receptor 2 (bacteria-expressed kinase, keratinocyte growth factor receptor) |
| CCDS3353.1 | NM_000142.2 | FGFR3 | fibroblast growth factor receptor 3 (achondroplasia, thanatophoric dwarfism)William Allan Nix |
| CCDS4410.1 | NM_002011.3 | FGFR4 | fibroblast growth factor receptor 4 isoform 1 |
| CCDS305.1 | NM_005248.2 | FGR | Gardner-Rasheed feline sarcoma viral (v-fgr) oncogene homolog |
| CCDS9330.1 | NM_002019.3 | FLT1/VEGFR1 | fms-related tyrosine kinase 1 (vascular endothelial growth factor/vascular permeability factor receptor) |
| CCDS31953.1 | NM_004119.2 | FLT3 | fms-related tyrosine kinase 3 |
| CCDS4457.1 | NM_182925.3 | FLT4/VEGFR3 | fms-related tyrosine kinase 4 |
| CCDS5103.1 | NM_002031.2 | FRK | fyn-related kinase |
| CCDS5094.1 | NM_002037.3 | FYN | FYN oncogene related to SRC, FGR, YES |
| CCDS33460.1 | NM_002110.2 | HCK | hemopoietic cell kinase |
| CCDS10378.1 | NM_000875.3 | IGF1R | insulin-like growth factor 1 receptor |
| CCDS12176.1 | NM_000208.2 | INSR | insulin receptor |

TABLE 2-continued

Tyrosine Kinase genes analyzed

| CCDS accession and amplimer number | Ref Seq accession and amplimer number | Gene Name | Gene Description |
|---|---|---|---|
| CCDS1160.1 | NM_014215.1 | INSRR | insulin receptor-related receptor |
| CCDS4336.1 | NM_005546.3 | ITK | IL2-inducible T-cell kinase |
| N/A | NM_002227.2 | JAK1 | Janus kinase 1 |
| CCDS6457.1 | NM_004972.2 | JAK2 | Janus kinase 2 |
| CCDS12366.1 | NM_000215.2 | JAK3 | Janus kinase 3 |
| CCDS3497.1 | NM_002253.1 | KDR/VEGFR2 | kinase insert domain receptor (a type III receptor tyrosine kinase) |
| CCDS3496.1 | NM_000222.2 | KIT | v-kit Hardy-Zuckerman 4 feline sarcoma viral oncogene homolog |
| CCDS359.1 | NM_005356.3 | LCK | lymphocyte-specific protein tyrosine kinase |
| CCDS10078.1 | NM_206961.1 | LTK | leukocyte tyrosine kinase |
| CCDS6162.1 | NM_002350.2 | LYN | v-yes-1 Yamaguchi sarcoma viral related oncogene homolog |
| CCDS12113.1 | NM_002378.3 | MATK | megakaryocyte-associated tyrosine kinase |
| CCDS2094.1 | NM_006343.2 | MERTK/MER | c-mer proto-oncogene tyrosine kinase |
| N/A | NM_000245.2 | MET | met proto-oncogene (hepatocyte growth factor receptor) |
| CCDS2807.1 | NM_002447.2 | MST1R/RON | macrophage stimulating 1 receptor (c-met-related tyrosine kinase) |
| N/A | NM_005592.1 | MUSK | muscle, skeletal, receptor tyrosine kinase |
| CCDS1161.1 | NM_002529.3 | NTRK1 | neurotrophic tyrosine kinase, receptor, type 1 |
| CCDS35053.1 | NM_001007097.1 | NTRK2 | neurotrophic tyrosine kinase receptor type 2 |
| CCDS32322.1 | NM_001012338.1 | NTRK3 | neurotrophic tyrosine kinase receptor type 3 |
| CCDS3495.1 | NM_006206.3 | PDGFRA | platelet-derived growth factor receptor alpha |
| CCDS4303.1 | NM_002609.3 | PDGFRB | platelet-derived growth factor receptor beta |
| CCDS4884.1 | NM_002821.3 | PTK7 | PTK7 protein tyrosine kinase 7 |
| CCDS6057.1 | NM_004103.3 | PYK2/PTK2B | PTK2B protein tyrosine kinase 2 beta |
| CCDS7200.1 | NM_020975.4 | RET | ret proto-oncogene |
| CCDS626.1 | NM_005012.2 | ROR1 | receptor tyrosine kinase-like orphan receptor 1 |
| CCDS6691.1 | NM_004560.2 | ROR2 | receptor tyrosine kinase-like orphan receptor 2 |
| CCDS5116.1 | NM_002944.2 | ROS1 | v-ros UR2 sarcoma virus oncogene homolog 1 (avian) |
| N/A | NM_001005861.2 | RYK | RYK receptor-like tyrosine kinase |
| CCDS13294.1 | NM_005417.3 | SRC | v-src sarcoma (Schmidt-Ruppin A-2) viral oncogene homolog (avian) |
| CCDS13525.1 | NM_080823.2 | SRMS | src-related kinase lacking C-terminal regulatory tyrosine and N-terminal myristylation sites |
| CCDS6688.1 | NM_003177.3 | SYK | spleen tyrosine kinase |
| CCDS3481.1 | NM_003215.2 | TEC | tec protein tyrosine kinase |
| CCDS6519.1 | NM_000459.2 | TEK | TEK tyrosine kinase, endothelial (venous malformations, multiple cutaneous and mucosal) |
| CCDS482.1 | NM_005424.2 | TIE | tyrosine kinase with immunoglobulin-like and EGF-like domains 1 |
| N/A | NM_003985.3 | TNK1 | tyrosine kinase, non-receptor, 1 |
| CCDS3480.1 | NM_003328.2 | TXK | TXK tyrosine kinase |
| CCDS12236.1 | NM_003331.3 | TYK2 | tyrosine kinase 2 |
| CCDS10080.1 | NM_006293.2 | TYRO3 | TYRO3 protein tyrosine kinase |
| CCDS11824.1 | NM_005433.3 | YES1 | v-yes-1 Yamaguchi sarcoma viral oncogene homolog 1 |
| CCDS33254.1 | NM_001079.3 | ZAP70 | zeta-chain (TCR) associated protein kinase 70 kDa |

Next, it was determined whether a mutation was somatic (i.e., tumor specific) by examining the sequence of the gene in genomic DNA from normal tissue of the relevant patient. From the approximately 12 Mb of sequence information obtained, 19 genes containing a total of 30 somatic mutations within their kinase domains were identified. All coding exons of these 19 genes were then analyzed for mutations in a total of 79 mM samples. The primers used for PCR amplification of ERBB4 (CCDS accession CCDS2394.1; GenBank Accession No. NM_005235.2; SEQ ID NO: 1) are listed in Table 3. ERBB4 was sequenced using the following primers:

```
Forward-TGTAAAACGACGGCCAGT      (SEQ ID NO: 78)

Reverse-CAGGAAACAGCTATGACC      (SEQ ID NO: 79)
```

TABLE 3

Primers used for PCR amplification of the ERBB4 kinase domain

| ERBB4 Exon | Forward Primer | SEQ ID NO: | Reverse Primer | SEQ ID NO: |
|---|---|---|---|---|
| Exon 18 | TCATTTGTGCAGCAACTTCTC | 64 | CTGTCCTAGGGTTTTGGCATT | 71 |
| Exon 19 | GCAGACAGTTGTGAAGCAAAAG | 65 | TGCTATCCTATTTCCATGCTGT | 72 |
| Exon 22 | CAAGCTTTAATTCGCAAAGAAGA | 66 | TCCCCACTTAATTATTTTTACCTTT | 73 |
| Exon 22 | TGCTTTAGGAAATTAGGCTTATC | 67 | GGCTACTCAGAGGCTAAGGTG | 74 |
| Exon 23 | TTTTTCCTTCATGTTTAGATCATTT | 68 | TTTTTAATTGATTGGTGTTTGG | 75 |
| Exon 23 | ACCTTGTCCTGCTAATTTGCTC | 69 | TGACCTGTAAGGAGTATTCTTTTACTAC | 76 |
| Exon 24 | CAGTAGCAGAGCCACTTGAA | 70 | TGTCCACCAGGACAAATGTA | 77 |

Figure 4:
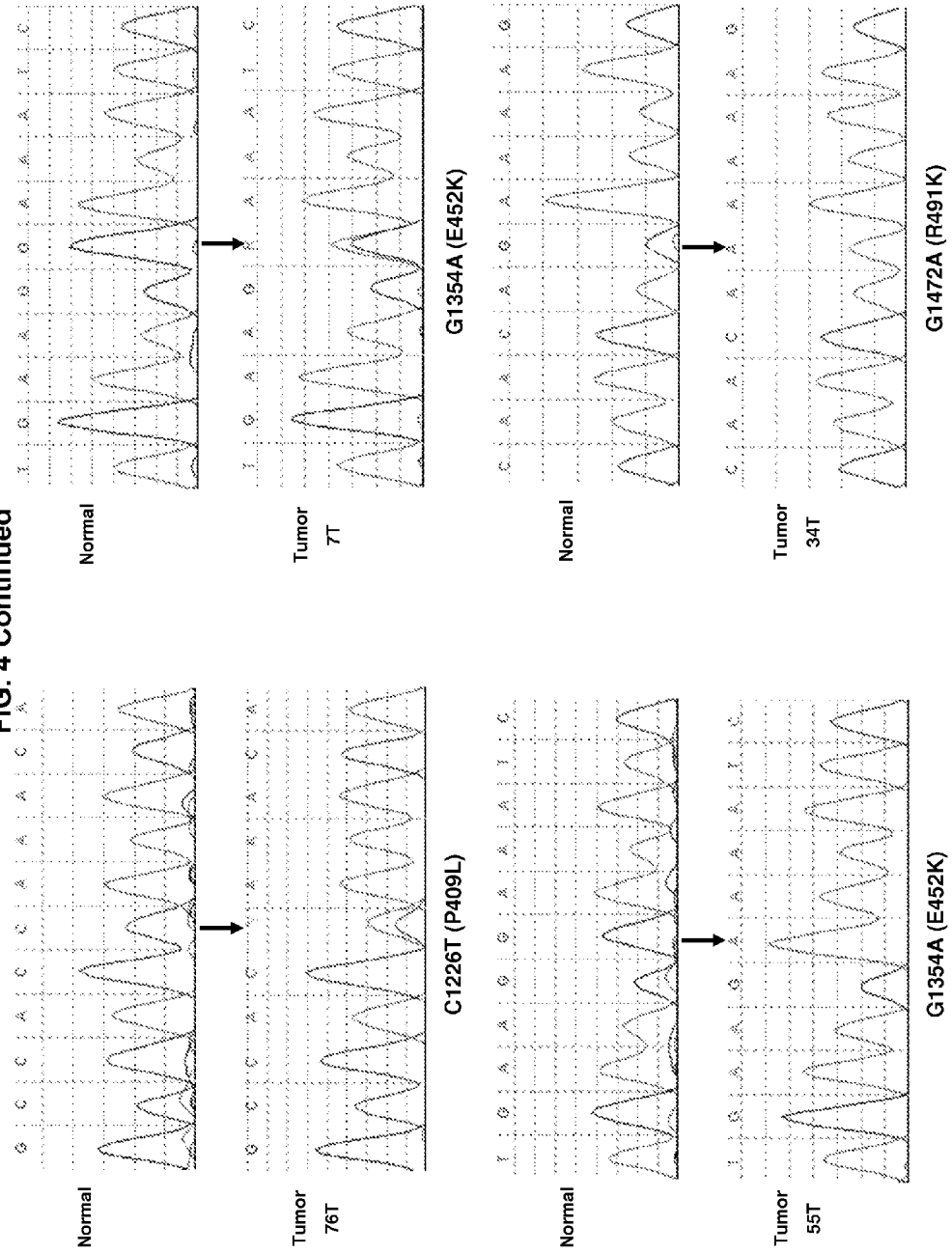
FIG. 4: Detection of mutations in ERBB4. Shown are eight matched sets of two chromatograms each, illustrating somatic mutations in the ERBB4 gene. In each case, the top sequence chromatogram was obtained from normal tissue and the lower sequence chromatogram from the indicated tumors. Arrows indicate the location of missense mutations. The nucleotide and amino acid alterations are indicated below the tumor chromatograms; numbering of the mutation locations is based on SEQ ID NO: 1 (nucleotide) and SEQ ID NO: 2 (amino acid).
Figure 5:
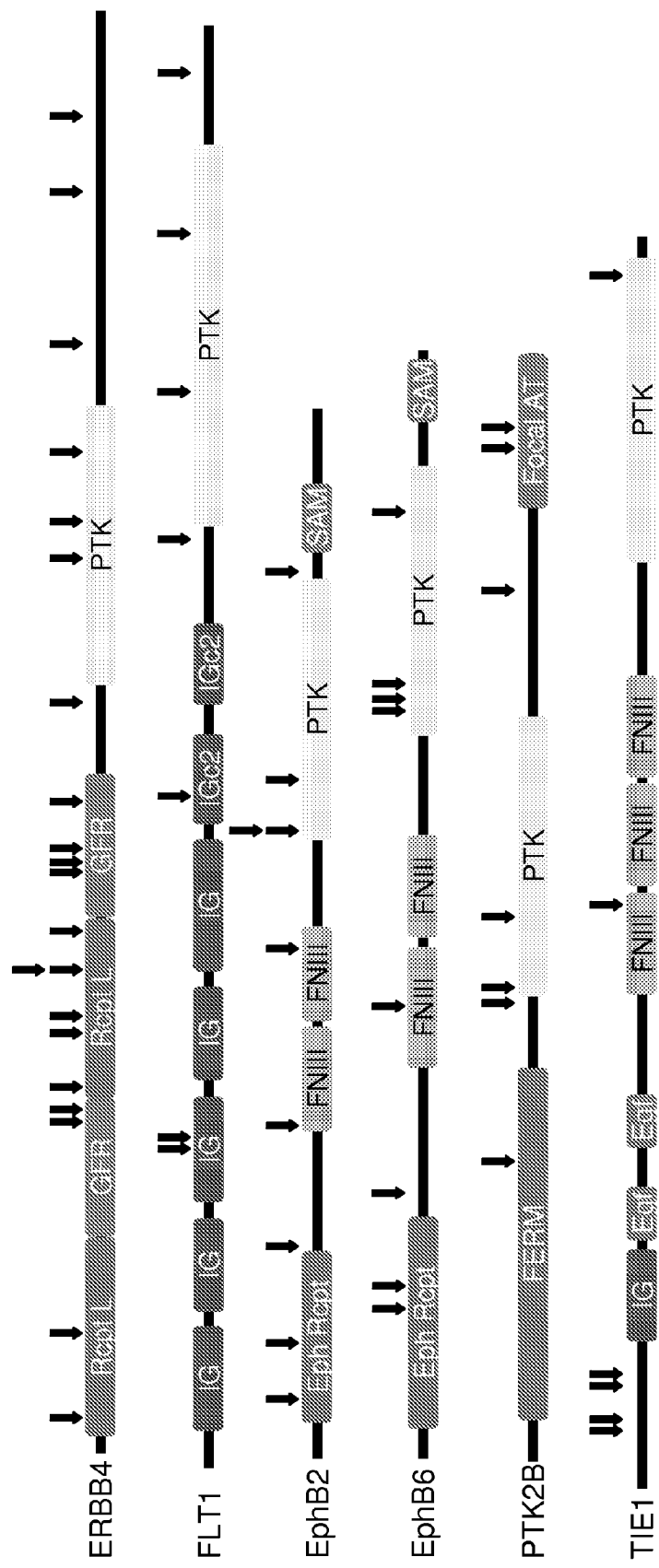
FIG. 5: Distribution of mutations in ERBB4, FL T1, EphB2, EphB6, PTK2B, and TIE1. Shown is a schematic of the domain structure of select PTKs. Arrows indicate positions of nonsynonymous mutations and boxes represent functional domains (Rcpt L, receptor L; GFR, growth factor receptor; PTK, protein tyrosine kinase; IG, immunoglobin; IGc2, immunoglobin C-2 Type; Eph Rcpt, ephrin receptor; FNIII, fibronectin type III; SAM, sterile alpha motif; FERM, protein 4.1, ezrin, radixin, moesin domain; Focal AT, focal adhesion targeting region).

Through this approach, 99 non-synonymous mutations were identified in 19 genes (Table 4, FIG. 4 and FIG. 5). All of these mutations were shown to be somatic by sequencing of DNA from matched normal tissue. Only three genes (EPHA6, PDGFRA and PTK2) out of the 19 had previously been reported to be mutated in MM (see Cancer Gene Census, available online at www.sanger.ac.uk/genetics/CGP/Census/). The majority of tumors with PTK gene mutations also contained mutations in NRAS or BRAF (Table 4).

TABLE 4

Somatic mutations identified in PTKs

| Gene | Other names | CCDS accession* | Ref Seq accession* | No. of mutations# | % of cases affected# | Exon | Nucleotide† | Amino Acid† | Functional Domain | Tumor | NRAS/BRAF mutation** |
|---|---|---|---|---|---|---|---|---|---|---|---|
| DDR1 | CAK, CD167 EDDR1, NEP, NTRK4 PTK3A, RTK6 | CCDS4690.1 | NM_001954.3 | 2 | 2.6 | 8 | C1115T | S372F | None | 6T | BRAF |
| | | | | | | 11 | G1709A | R570Q | Protein Tyrosine Kinase | 43T | BRAF |
| FER | TYK3 | CCDS4098.1 | NM_005246.1 | 2 | 2.6 | 11 | T1594C | Y532H | SH2 Motif | 58T | BRAF |
| | | | | | | 13 | G1739A | G580D | Protein Tyrosine Kinase | 30T | BRAF |
| FLT1 | FLT VEGFR1 | CCDS9330.1 | NM_002019.3 | 8 | 10.3 | 7 | G842A | R281Q | IG | 37T | BRAF |
| | | | | | | 7 | C860T | S287F | IG | 7T | NRAS |
| | | | | | | 12 | −9 Intronic C > A | Splice Site | N/A | 20T | BRAF |
| | | | | | | 13 | G1767A | W589X | IGc2 | 13T | None |
| | | | | | | 17 | C2440T | P814S | None | 39T | None |
| | | | | | | 21 | G2827A | E943K | Protein Tyrosine Kinase | 44T | NRAS |
| | | | | | | 24 | G3241A | D1081N | Protein Tyrosine Kinase | 78T | BRAF |
| | | | | | | 28 | G3667A | E1223K/LOH | None | 85T | BRAF |
| EPHA6 | FLJ35246 | | NM_001080448.2 | 5 | 6.4 | 1 | C1202G | T307S | None | 30T | BRAF |
| | | | | | | 4 | G1763T | R494M | Protein Tyrosine Kinase | 36T | BRAF |
| | | | | | | 4 | G1891A | E537K | Protein Tyrosine Kinase | 32T | BRAF |
| | | | | | | 8 | A2246T | K655I | Protein Tyrosine Kinase | 29T | BRAF |
| | | | | | | 8 | G2320A | E680K | None | 21T | BRAF |
| EPHA10 | FLJ16103 FLJ33655 | CCDS41305.1 | NM_001099439.1 | 7 | 6.4 | 3 | G235A | V79M | Ephrin Receptor | 52T | BRAF |
| | | | | | | 3 | T236C | V79A | Ephrin Receptor | 52T | BRAF |
| | | | | | | 3 | G370A | E124K | Ephrin Receptor | 55T | None |
| | | | | | | 3 | G649A | G217S | None | 71T | BRAF |
| | | | | | | 3 | G650A | G217D | None | 71T | BRAF |
| | | | | | | 13 | G2369A | G790E | Protein Tyrosine Kinase | 63T | NRAS |

TABLE 4-continued

Somatic mutations identified in PTKs

| Gene | Other names | CCDS accession* | Ref Seq accession* | No. of muta-tions# | % of cases af-fected# | Exon | Nucleotide† | Amino Acid† | Functional Domain | Tu-mor | NRAS/ BRAF muta-tion** |
|---|---|---|---|---|---|---|---|---|---|---|---|
| | | | | | | 14 | G2528C | G843A | Protein Tyrosine Kinase | 37T | BRAF |
| EPHB1 | EPHT2 | | NM_004441 | 4 | 5.1 | 3 | C235T | R79W | Ephrin Receptor | 39T | None |
| | Hek6 | | | | | 12 | G2311A | D771N | Protein Tyrosine Kinase | 60T | NRAS |
| | | | | | | 13 | G2432A | G811E | Protein Tyrosine Kinase | 44T | NRAS |
| | | | | | | 15 | G2757A | W919X | Sterile Alpha Motif | 63T | NRAS |
| EPHB2 | DRT | CCDS229.2 | NM_017449.1 | 7 | 9.0 | 3 | G325A | E109K | Ephrin Receptor | 4T | BRAF |
| | EPHT3 | | | | | 3 | C614T | A205V | None | 72T | None |
| | ERK | | | | | 4 | G952A | D318N | Fibronectin Type 3 Domain | 71T | BRAF |
| | Hek5 | | | | | 7 | C1535T | T512I | Fibronectin Type 3 Domain | 83T | Both |
| | Tyro5 | | | | | 10 | G1846A | E615K | Protein Tyrosine Kinase | 29T | BRAF |
| | | | | | | 10 | G1846A | E615K | Protein Tyrosine Kinase | 68T | BRAF |
| | | | | | | 14 | C2663T | P887L | None | 77T | None |
| EPHB6 | HEP | CCDS5873.1 | NM_004445.1 | 7 | 9.0 | 3 | C392T | S131F | Ephrin Receptor | 60T | NRAS |
| | | | | | | 3 | C455T | S152F | Ephrin Receptor | 55T | None |
| | | | | | | 5 | G1210A | G404S | Fibronectin Type 3 Domain | 50T | BRAF |
| | | | | | | 11 | G2036A | R679Q | Protein Tyrosine Kinase | 5T | BRAF |
| | | | | | | 11 | C2063G | A688G | Protein Tyrosine Kinase | 54T | BRAF |
| | | | | | | 11 | C2110T | R704W | Protein Tyrosine Kinase | 26T | BRAF |
| | | | | | | 13 | −5 Intronic C > T | Splice Site | N/A | 18T | None |
| ERBB4 | HER4 | CCDS2394.1 | NM_005235.2 | 24 | 18.8 | 2 | C113T | L39F | Receptor L Domain | 71T | BRAF |
| | MGC138404 | | | | | 3 | T331C | Y111H | Receptor L Domain | 13T | None |
| | p180erbB4 | | | | | 8 | G939A | M313I | Growth Factor Receptor | 63T | NRAS |
| | | | | | | 8 | G949A | E317K | Growth Factor Receptor | 17T | NRAS |
| | | | | | | 9 | C1022T | S341L | Receptor L Domain | 96T | None |
| | | | | | | 10 | C1177T | R393W | Receptor L Domain | 49T | BRAF |
| | | | | | | 11 | C1226T | P409L | Receptor L Domain | 76T | None |
| | | | | | | 12 | G1354A | E452K | Receptor L Domain | 7T | NRAS |
| | | | | | | 12 | G1354A | E452K/ LOH | Receptor L Domain | 55T | None |
| | | | | | | 12 | G1472A | R491K/ LOH | Growth Factor Receptor | 34T | BRAF |
| | | | | | | 14 | G1624A | E542K | Growth Factor Receptor | 63T | NRAS |
| | | | | | | 14 | C1630T | R544W | Growth Factor Receptor | 56T | BRAF |
| | | | | | | 14 | G1687A | E563K | Growth Factor Receptor | 12T | NRAS |

TABLE 4-continued

Somatic mutations identified in PTKs

| Gene | Other names | CCDS accession* | Ref Seq accession* | No. of mutations# | % of cases affected# | Exon | Nucleotide† | Amino Acid† | Functional Domain | Tumor | NRAS/BRAF mutation** |
|---|---|---|---|---|---|---|---|---|---|---|---|
| | | | | | | 15 | −10 Intronic C > T | Splice Site/LOH | N/A | 68T | BRAF |
| | | | | | | 15 | G1825A | D609N | Growth Factor Receptor | 76T | None |
| | | | | | | 18 | C2098T | P700S | None | 24T | NRAS |
| | | | | | | 21 | G2506A | E836K | Protein Tyrosine Kinase | 86T | BRAF |
| | | | | | | 21 | G2614A | E872K | Protein Tyrosine Kinase/Activation Loo | 63T | NRAS |
| | | | | | | 23 | G2806A | G936R | Protein Tyrosine Kinase | 24T | NRAS |
| | | | | | | 24 | −4 Intronic C > T | Splice Site | N/A | 13T | None |
| | | | | | | 25 | C3097T | P1033S | None | 76T | None |
| | | | | | | 26 | −1 Intronic G > A | Splice Site | N/A | 76T | None |
| | | | | | | 28 | G3521A | R1174Q | None | 63T | NRAS |
| | | | | | | 28 | G3737A | S1246N | His-Me Finger Endonucleases | 71T | BRAF |
| MATK | CTK | CCDS12113.1 | NM_002378.2 | 1 | 1.3 | 12 | G1248A | W416X | Protein Tyrosine Kinase | 13T | None |
| MET | HYLTK HGFR | CCDS43636.1 | NM_000245 | 3 | 3.8 | 5 | G1829A | C610Y/LOH | IPT | 1T | BRAF |
| | | | | | | 14 | A3176G | N1059S | None | 13T | None |
| | | | | | | 16 | G3509A | R1170Q | Protein Tyrosine Kinase | 29T | BRAF |
| NTRK1 | MTC TRK TRKA | CCDS1161.1 | NM_002529.2 | 2 | 2.6 | 8 | G1137A | M349I | None | 18T | None |
| | | | | | | 14 | C1747G | R547G | Protein Tyrosine Kinase | 13T | None |
| PDGFRA | CD140a PDGFR2 | CCDS3495.1 | NM_006206.2 | 5 | 5.1 | 3 | G571A | A191T | IG | 64T | BRAF |
| | | | | | | 9 | G1375A | E459K/LOH | None | 32T | BRAF |
| | | | | | | 18 | C2669T | S890F | Protein Tyrosine Kinase | 41T | BRAF |
| | | | | | | 20 | C2810T | P937L/LOH | Protein Tyrosine Kinase | 32T | BRAF |
| | | | | | | 21 | G3070A | D1024N | None | 63T | NRAS |
| PTK2 | FAK, FADK FAK1, pp125FAK | CCDS6381.1 | NM_153831.2 | 1 | 1.3 | 15 | C1481T | A494V | Protein Tyrosine Kinase | 13T | None |
| PTK2B | PYK2 | CCDS6057.1 | NM_173176.1 | 8 | 10.0 | 5 | −4 Intronic C > T | Splice Site | N/A | 79T | BRAF |
| | PKB | | | | | 8 | G818A | W273X | FERM | 76T | None |
| | PTK | | | | | 13 | G1241A | G414E | None | 95T | NRAS |
| | CAKB | | | | | 14 | C1285T | R429C | Protein Tyrosine Kinase | 17T | NRAS |
| | FAK2 | | | | | 16 | G1480A | E494K | Protein Tyrosine Kinase | 26T | BRAF |
| | FRNK CADTK FADK2 RAFTK | | | | | 24 | G2374A | E792K | None | 36T | BRAF |
| | | | | | | 29 | G2753A | R918Q | Focal AT | 85T | BRAF |
| | | | | | | 29 | G2812A | E938K | Focal AT | 83T | Both |
| PTK6 | BRK | CCDS13524.1 | NM_005975.2 | 2 | 2.6 | 4 | G629A | W210X | Protein Tyrosine Kinase | 12T | NRAS |

TABLE 4-continued

Somatic mutations identified in PTKs

| Gene | Other names | CCDS accession* | Ref Seq accession* | No. of mutations# | % of cases affected# | Exon | Nucleotide† | Amino Acid† | Functional Domain | Tumor | NRAS/BRAF mutation** |
|---|---|---|---|---|---|---|---|---|---|---|---|
| | | | | | | 5 | −7 Intronic C > T | Splice Site | N/A | 51T | BRAF |
| PTK7 | CCK4 | CCDS4884.1 | NM_002821.3 | 1 | 1.3 | 7 | C1054T | P352S | IGc2 | 84T | BRAF |
| ROR2 | BDB | CCDS6691.1 | NM_004560.2 | 4 | 5.1 | 5 | T574C | Y192H | Frizzled Cysteine-Rich Domain | 71T | BRAF |
| | BDB1 | | | | | 7 | T1172C | V391A | Kringle | 72T | None |
| | NTRKR2 | | | | | 9 | C1670T | S557L | Protein Tyrosine Kinase | 5T | BRAF |
| | | | | | | 9 | G2377T | A793S | None | 81T | BRAF |
| TIE1 | JTK14 | CCDS482.1 | NM_005424.2 | 6 | 7.7 | 2 | G139A | E47K | None | 13T | None |
| | TIE | | | | | 2 | C161T | S54L | None | 16T | BRAF |
| | | | | | | 2 | C266T | T89M | None | 52T | BRAF |
| | | | | | | 2 | G292A | D98N | None | 43T | BRAF |
| | | | | | | 11 | G1598A | G533E | Fibronectin Type 3 Domain | 39T | None |
| | | | | | | 22 | C3281T | P1094L/LOH | Protein Tyrosine Kinase | 12T | NRAS |

*Accession numbers for mutated PTKs in Santa Cruz and GenBank.
Number of non-synonymous and splice site mutations observed and percent of tumors affected for each of the 19 genes in the panel of 80 melanoma cancers.
†Nucleotide and amino acid change resulting from mutation.
"X" refers to stop codon.
"LOH" refers to cases wherein the wild-type allele was lost and only the mutant allele remained.
"Splice site" refers to a case wherein the alteration affected ten bases spanning the exon.
**Mutations previously observed in NRAS, or BRAF.
"None" refers to no mutation observed.
SH2 Motif, Src homology 2 domain;
IG, Immunoglobin;
IGc2, Immunoglobin C-2 Type;
IPT, IG-like, plexins, transcription factors;
Focal AT, Focal Adhesion Targeting Region;
FERM, Protein 4.1, Ezrin, Radixin, Moesin Domain.
Domains were found using Ensembl and InterPro.

The observed somatic mutations could either be "driver" mutations that play a functional role underlying the neoplastic process or nonfunctional "passenger" changes. In the 19 genes found to be mutated, 99 non-synonymous and 17 synonymous somatic mutations were identified, yielding a N:S (non-synonymous: synonymous) ratio of 99:17, significantly higher than the N:S ratio of 2.5:1 predicted for nonselected passenger mutations ($P<1\times10^{-5}$) (Sjoblom et al., *Science* 314:268-274, 2006), suggesting that these are likely to be "driver" mutations. The number of C>T mutations was significantly greater than other nucleotide substitutions resulting in a high prevalence of C:G>T:A transitions (p<0.0001) (FIG. 6A), confirming previously reported melanoma signatures. A summary of the most highly mutated genes is shown in FIG. 5.

Example 3

Somatic Mutations within ERBB4 are Frequent in MM

This example describes the biochemical analysis of several ERBB4 mutations identified in patients with melanoma. To evaluate the effect of some of these mutations on kinase function, the studies described herein focus on ERBB4, a member of the EGFR kinase subfamily, which was the most highly mutated gene (19%) in the screen. Five of the 15 samples with ERBB4 mutations contained more than one somatic mutation in ERBB4, which may act synergistically as previously seen for EGFR (Godin-Heymann et al., *Cancer Res.* 67:7319-7326, 2007). The large number of mutations observed in ERBB4 strongly suggests that these mutations are functionally important (FIG. 1A). This conclusion is supported by analysis of the ratio of non-synonymous to synonymous mutations in ERBB4, which was 24:3, significantly higher than the 2.5:1 ratio expected by chance ($P<1\times10^{-2}$) (Sjoblom et al., *Science* 314:268-274, 2006).

Interestingly, 7 out of the 24 non-synonymous somatic mutations discovered in ERBB4 occurred at Glu (E) residues (p<0.00005, binomial test), all of which resulted in changes to Lys (K), causing a charge reversal. The underlying reason for this might be due to the high frequency of C:G>T:A transitions (FIG. 6B). Clustering of somatic mutations is seen in various functional domains of ERBB4 (FIG. 1A and FIG. 5), with mutations in the kinase domain co-localizing with previously described mutations (found in various cancer types at frequencies ranging from 1.1-4.7%; Soung et al., *Int. J. Cancer* 118:1426-1429, 2006; Ding et al., *Nature* 455:1069-1075, 2008) and occurring at highly conserved residues. These genetic data suggest that mutant ERBB4 is likely to function as an oncogene in melanoma.

The positions of these mutations within ERBB4 and their predominantly heterozygous nature imply that they are likely to be gain of function mutations. No truncating mutations were observed and the alterations occurred in functionally important domains (FIG. 1A). The affected residues in ERBB4 are highly conserved evolutionarily, retaining identity in chimp, horse, rat, mouse and opossum. Clustering of somatic missense mutations is seen in various domains. Mutations S341L, R393W, P409L, E452K and R491K all occur in the extracellular sub region III, with the E452K mutation occurring in two different cases. Mutations E542K, R544W and E563K are all adjacent in the extracellular sub region IV. A similar clustering was observed in the kinase domain where our novel mutations co-localized with previously described mutations (found in various cancer types at frequencies ranging from 1.1%-4.7% (Ding et al., *Nature* 455:1069-1075, 2008; Soung et al., *Int. J. Cancer* 118:1426-1429, 2006). The clustering of somatic missense mutations in specific domains of ERBB4 is similar to that observed for activating mutations in other oncogenes, such as BRAF and PIK3CA (Davies et al., *Nature* 417(6892):949-954, 2002; Samuels et al., *Science* 304:554, 2004). These genetic data suggest that mutant ERBB4 is likely to function as an oncogene in MM.

Example 4

ERBB4 Mutations Increase its Kinase Activity

This example describes the assessment of kinase activity of ERBB4 mutations present in melanoma tumors. To directly test whether the mutations identified in ERBB4 activate its kinase activity, the positions of the various ERBB4 missense mutations in its crystal structure were assessed. The crystal structures of the extracellular and kinase domains of ERBB4 (Bouyain et al., *Proc. Natl. Acad. Sci. USA* 102:15024-15029, 2005; Qiu et al., *Structure* 16:460-467, 2008) demonstrated that most of the observed alterations had similar positioning to mutations reported in the ERBB4 family members EGFR and ERBB2 in lung cancer, glioblastoma and gastric cancer (Riese et al., *Bioessays* 29:558-565, 2007). The mutations that were further evaluated in the extracellular domain included the E317K mutation, which is near the EGFR R324L mutation, the E542K, R544W, and E563K mutations, as these co-localize, and finally the E452K mutation, as this substitution occurred in two patients. Additionally, two mutations that were found in the kinase domain were cloned: E836K, which is found near the ERBB2 N857S mutation, and the E872K alteration.

Figure 1B:
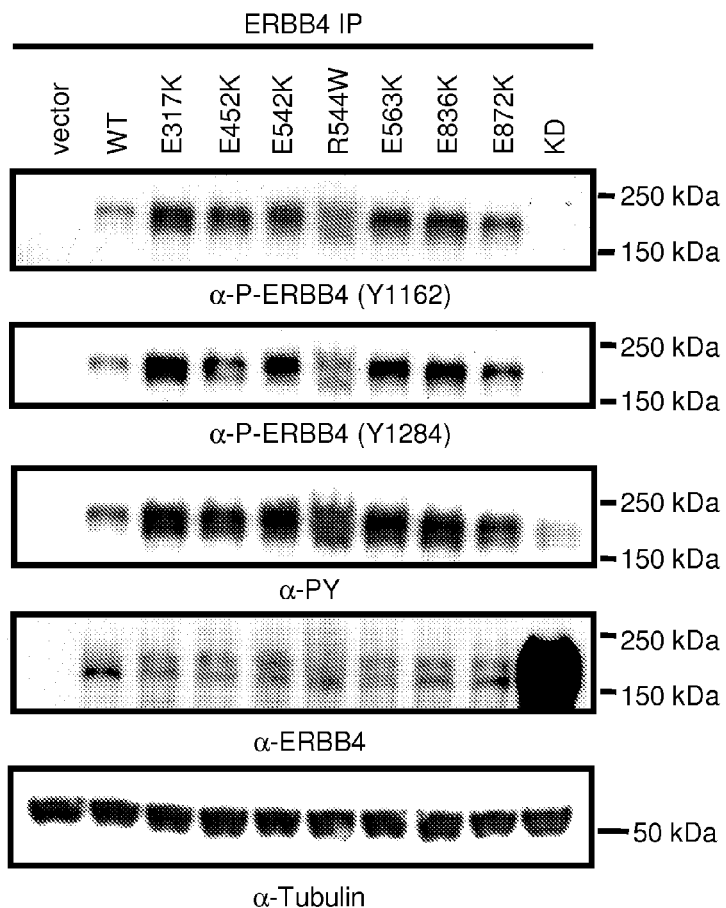

To investigate the biochemical effects of the identified ERBB4 mutations, wild type (WT) ERBB4 or the seven mutants (E317K, E452K, E542K, R544W, E563K, E836K, E872K), as well as a kinase dead (KD) version of ERBB4 (K751M), were transiently expressed in HEK 293T cells and the basal catalytic activity of ERBB4 was assessed using ERBB4 autophosphorylation as a readout for receptor activation. ERBB4 autophosphorylation was determined by measuring the total phosphotyrosine content of the immunoprecipitated receptor as well as by measuring two autophosphorylation sites (Tyr-1162 and Tyr-1284) in the C-terminus of ERBB4. Compared to WT ERBB4, all the missense mutants showed a marked increase in receptor autophosphorylation on total phosphotyrosine as well as on residues Tyr-1162 and Tyr-1284 (FIG. 1B). No site-specific phosphorylation was observed in cells exogenously expressing the KD version of ERBB4. Similar expression levels of total ERBB4 protein were observed, except KD ERBB4, which had a higher expression level (FIG. 1B).

Figure 1C:
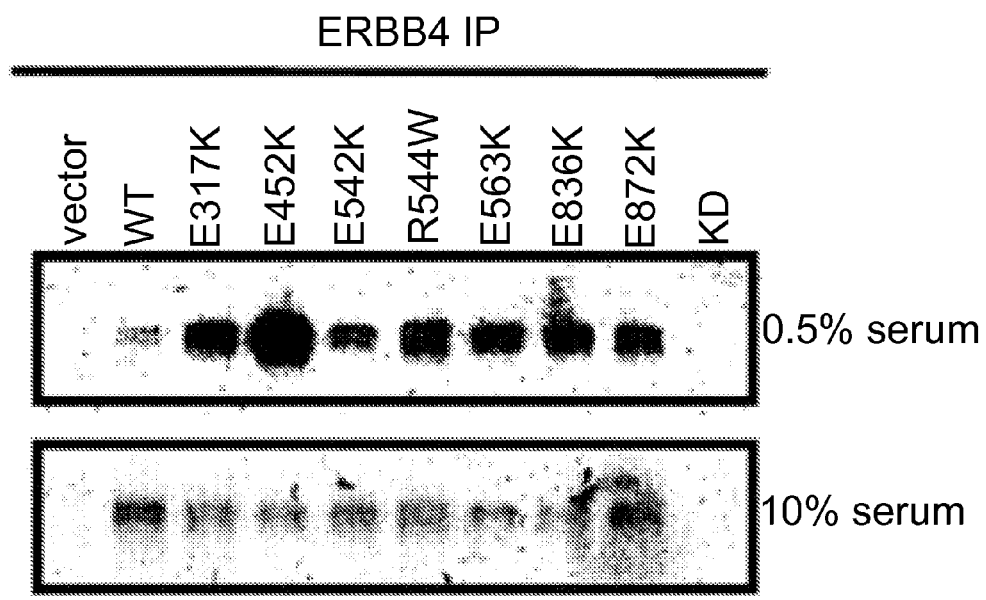
Figure 1D:
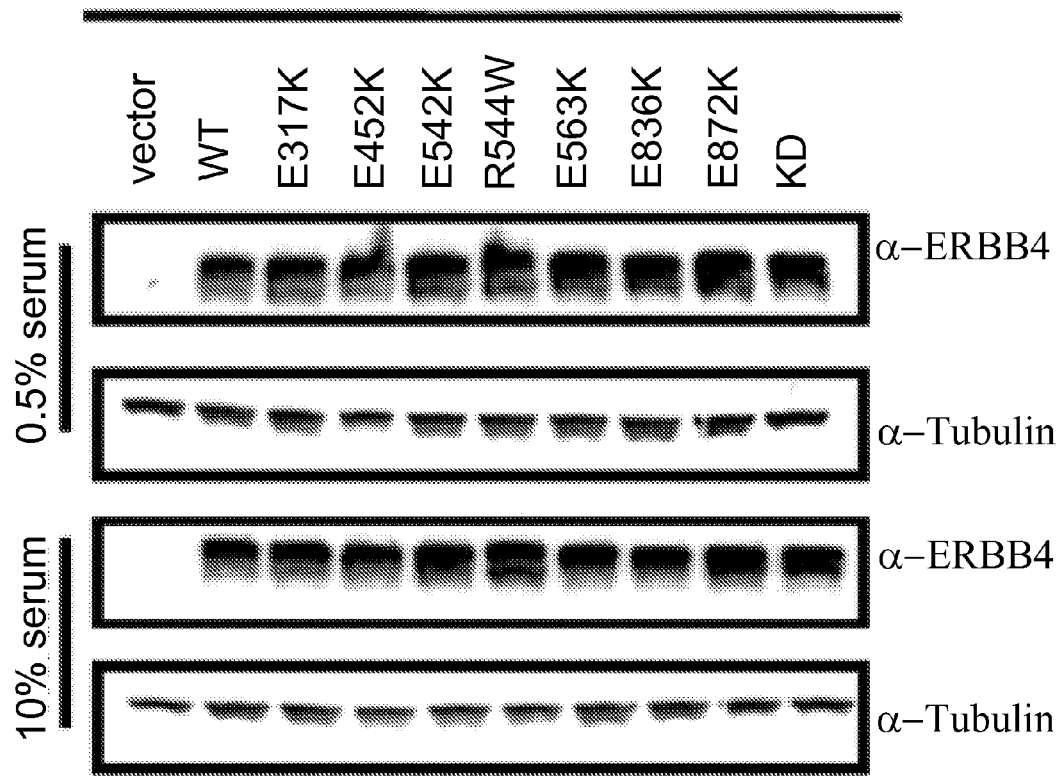

The specificity of the phosphosite-specific anti-ERBB4 antibodies was confirmed using competitive ERBB4-phosphosite-specific phospho-peptides (FIG. 7). To assess whether the increased tyrosine phosphorylation of the ERBB4 mutants correlates with increased kinase activity, a kinase assay using the same set of ERBB4 mutants was performed. FIGS. 1C-1D show that in low serum, the ERBB4 mutants exhibit a marked increase in kinase activity compared to WT ERBB4. In contrast, in the presence of serum, the ERBB4 mutants showed a similar kinase activity compared to WT ERBB4. Similar expression levels of total ERBB4 protein were observed (FIG. 1D). These results suggest that increased ERBB4 phosphorylation is due to its constitutive activation rather than alteration in its protein levels.

Figure 8:
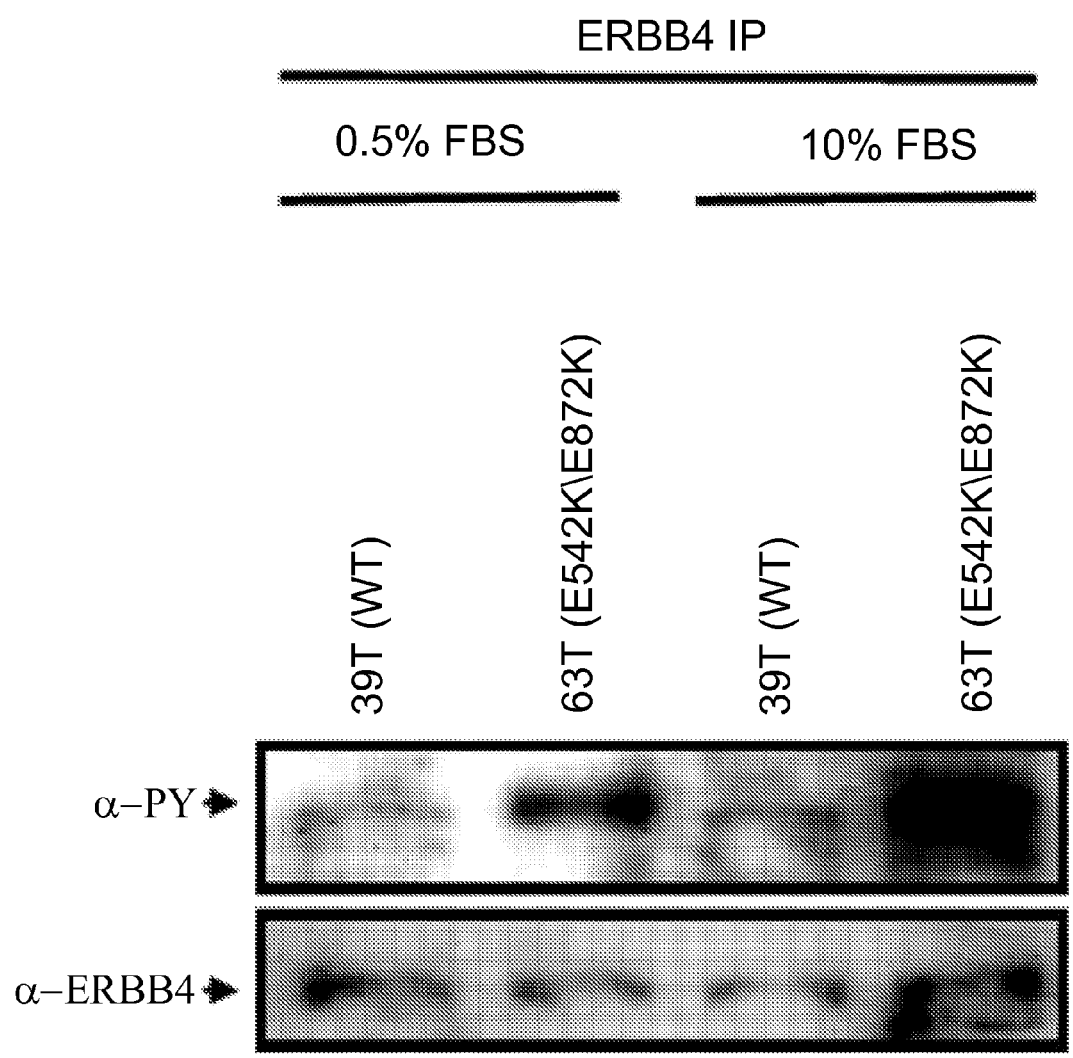
FIG. 8: Increased basal activation of endogenous mutant ERBB4. Shown is a set of two immunoblots demonstrating detection of phosphorylated ERBB4 in melanoma cell lines expressing WT or mutant ERBB4. MM lines that harbor either WT or mutant ERBB4 cells were either grown in 10% serum or serum starved and then lysed. Shown are immunoblots of immunoprecipitated ERBB4 probed with the indicated antibodies.

To extend these observations, a MM line containing endogenous mutant ERBB4 (63T, E542K/E872K) was studied and compared it to a MM line containing endogenous WT ERBB4 (39T). As in transfected cells, ERBB4 autophosphorylation was markedly elevated in the MM line with an endogenous ERBB4 mutation (FIG. 8).

Figure 1E:
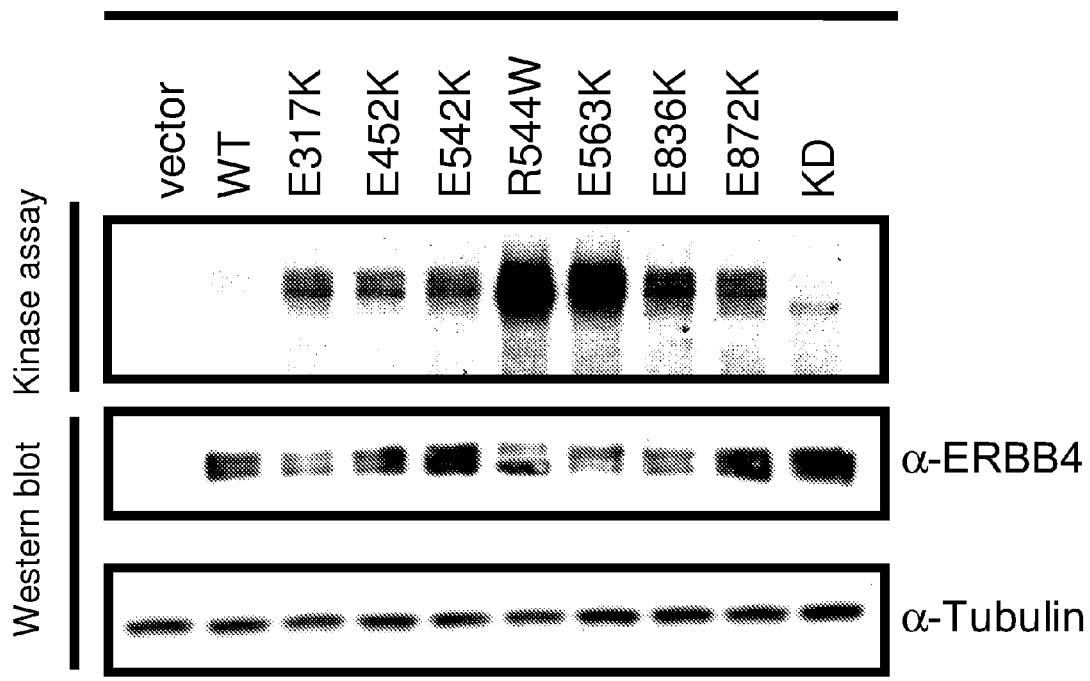
Figure 1F:
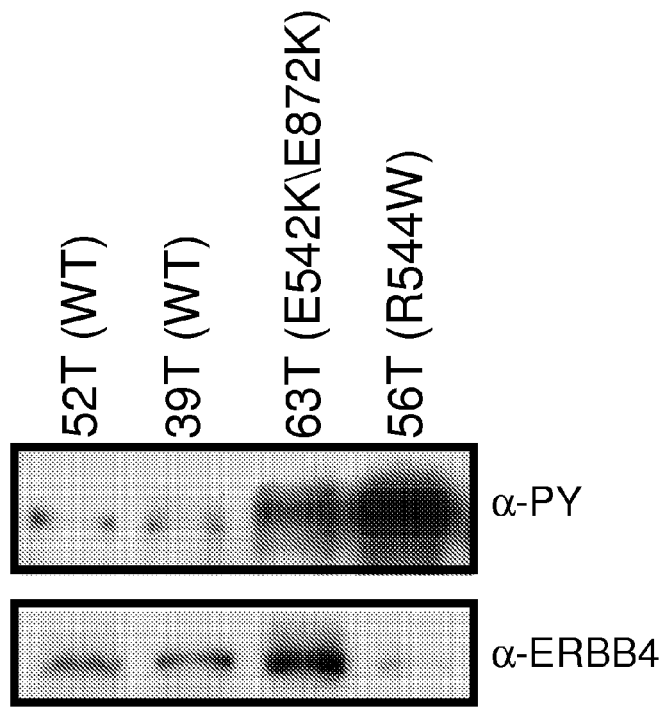
Figure 1G:
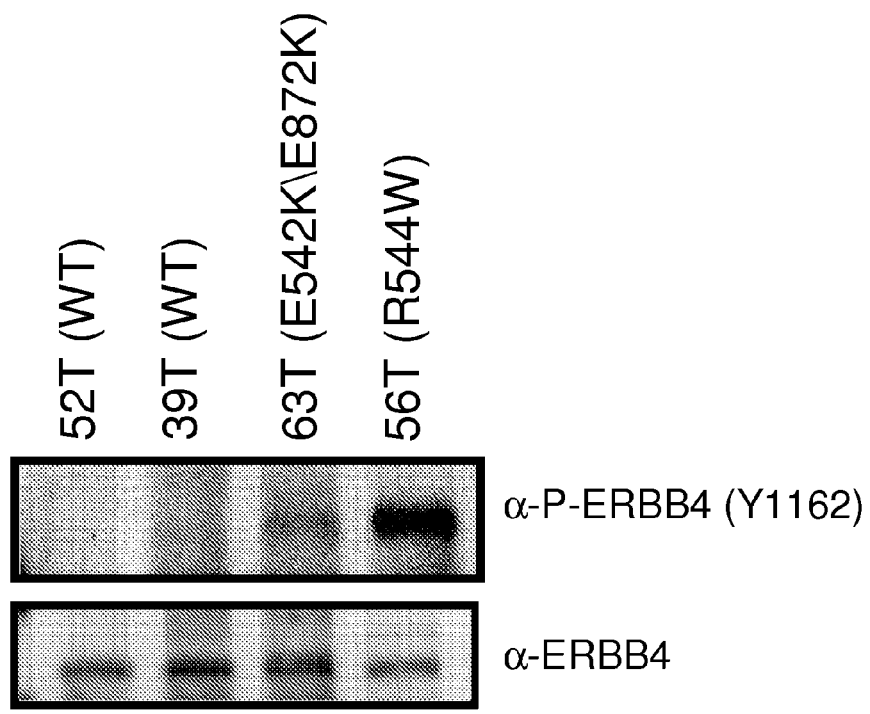

To determine if the increased tyrosine phosphorylation of the ERBB4 mutants correlates with increased kinase activity, a kinase assay using the same set of ERBB4 mutants was performed. The ERBB4 mutants showed a marked increase in kinase activity compared to WT ERBB4 and expression levels of total ERBB4 protein were comparable (FIG. 1E). As in transfected cells, ERBB4 autophosphorylation was markedly elevated in the melanoma lines harboring ERBB4 mutations compared to melanoma lines harboring endogenous WT ERBB4 (FIGS. 1F-1G).

Figure 11:
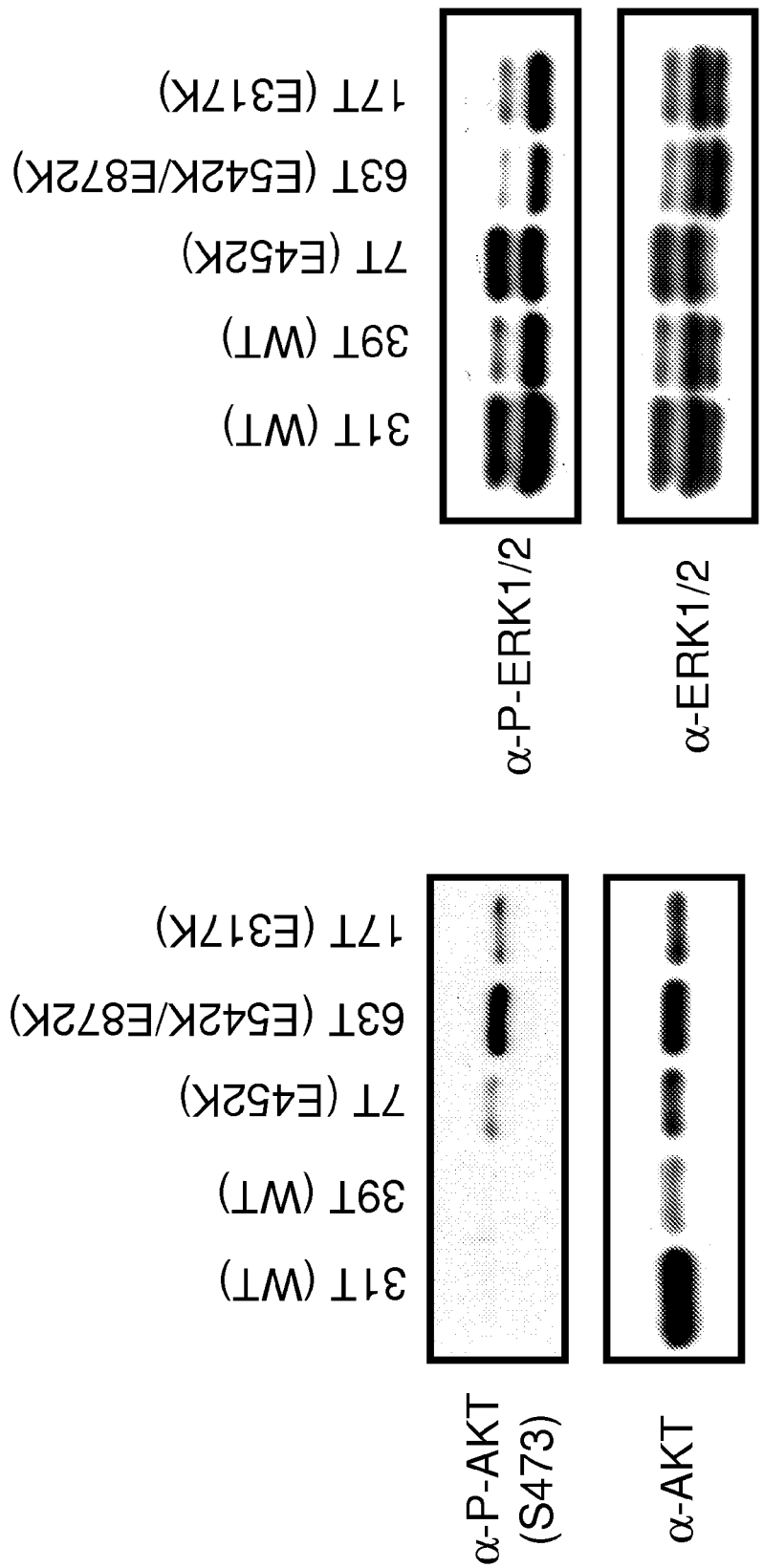
FIG. 11: Effects of ERBB4 mutation on AKT and ERK phosphorylation. Melanoma cell lines containing either WT or mutant ERBB4 were harvested and analyzed by immunoblot. Shown are immunoblots of lysates probed with the indicated antibodies (α-P-ERK1/2—recognizes phosphorylation of T202 and Y204 on ERK1, and T185 and Y187 on ERK2).

ERBB4 is known to activate several downstream signaling pathways including the ERK and AKT pathways (Frey et al., *Gastroenterology* 136:217-226, 2009). To evaluate which of these signaling pathways is activated by the ERBB4 mutations, immunoblot analysis of melanoma cell lines harboring endogenous ERBB4 mutations was performed. Phosphorylation of AKT was elevated in cells expressing any of the three evaluated mutant ERBB4s, whereas ERK showed similar activation in cells expressing WT or mutant ERBB4 (FIG. 11).

Example 5

Figure 2A:
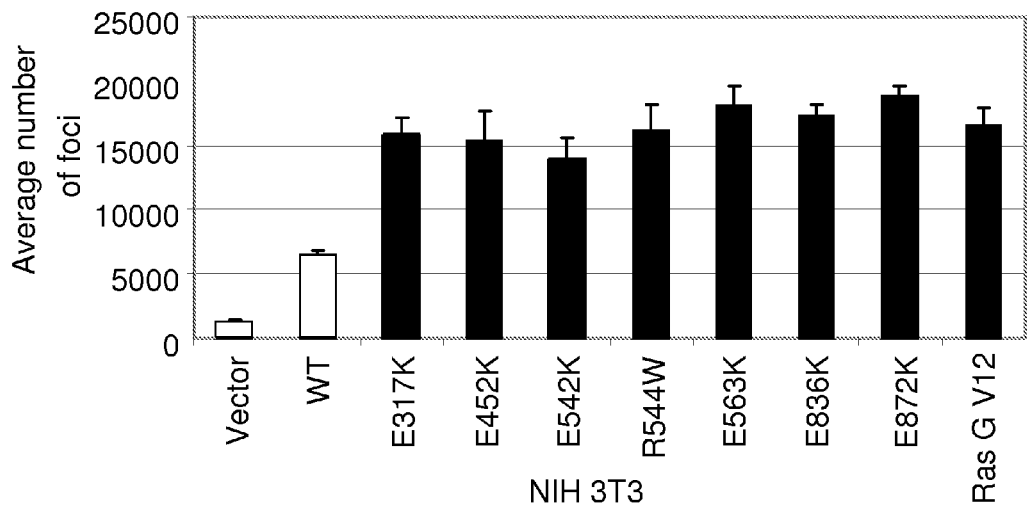
FIG. 2: Mutant ERBB4 induces transformation and anchorage independent growth in NIH 3T3 and SK-Mel-2 cells. (A) NIH 3T3 cells were transfected with the indicated ERBB4 mutant or control constructs. The graph indicates the average number of transformed foci after 10 days. (B) Growth in soft agar of melanoma SK-Mel-2 cells stably expressing either vector, WT ERBB4 or various ERBB4 missense mutants. The graph indicates the number of colonies after 14 days.
Figure 9A:
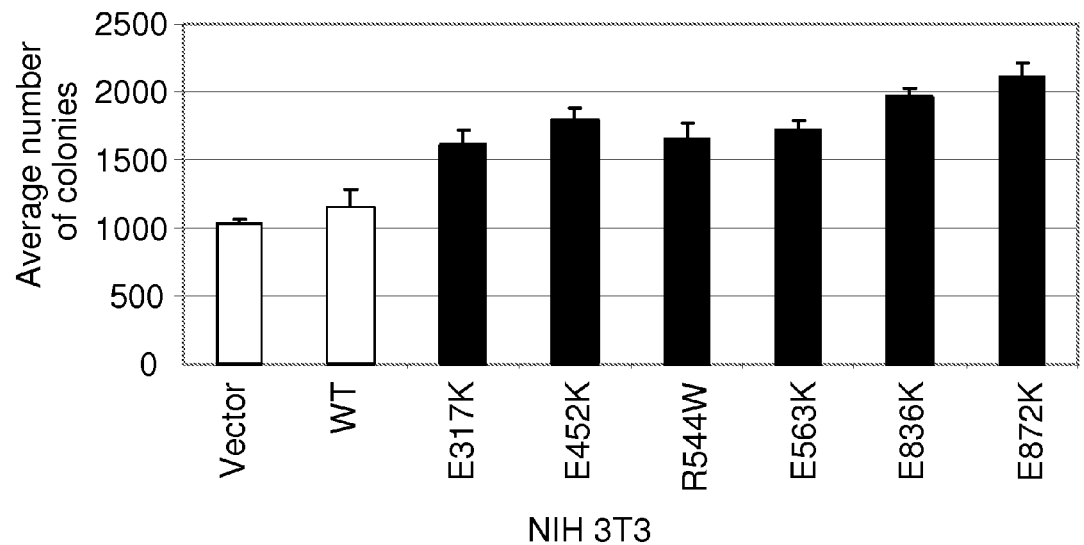
FIG. 9: Effect of ERBB4 mutations on cell growth in NIH 3T3 and SK–Mel-2 cells. (A) Growth in soft agar of NIH 3T3 cells expressing either vector, WT ERBB4 or various ERBB4 missense mutants. The graph indicates the number of colonies after 14 days. (B and C) Detection of ERBB4 protein expression in stable transfectants of SK-Mel-2 melanoma cells by western blot analysis. Lysates from the different clones stably transfected with an empty vector, human ERBB4 or the indicated ERBB4 mutants were immunoprecipitated and immunoblotted with ERBB4 antibody (B). Anchorage independent proliferation of SK-Mel-2 cell clones expressing the indicated constructs was assessed by measuring colony growth in soft agar (C). The graph indicates the number of colonies observed after 14 days of growth.

ERBB4 Mutations Promote Colony Formation Abilities and Anchorage-Independent Growth The example describes the phenotypic analysis of ERBB4 mutants identified in melanoma tumors. The combination of biochemical and genetic data disclosed herein suggested that the mutant ERBB4 proteins might be oncogenic. However, previous studies have described the generation of ERBB4 mutants that are constitutively active but non-transforming (Penington et al., *Cell Growth Differ.* 13:247-256, 2002; Williams et al., *Cancer Lett.* 192:67-74, 2003). Thus, the following studies were performed to determine whether the melanoma ERBB4 variants described in this study are transforming To test this, NIH 3T3 cells were transiently transfected with vector, WT, one of the seven constitutively active ERBB4 mutants (E317K, E452K, E542K, R544W, E563K, E836K and E872K) or oncogenic K-Ras$^{G12V}$. Ten days after transfection, all ERBB4 mutations transformed NIH 3T3 cells more efficiently than WT ERBB4. Strikingly, the transformation ability of the ERBB4 mutants was similar to oncogenic K-Ras$^{G12V}$ (FIG. 2A). Similarly, the same set of ERBB4 mutants were able to promote anchorage-independent growth as depicted in FIG. 9A. All the presented results were significant ($P<0.05$, t test).

Figure 2B:
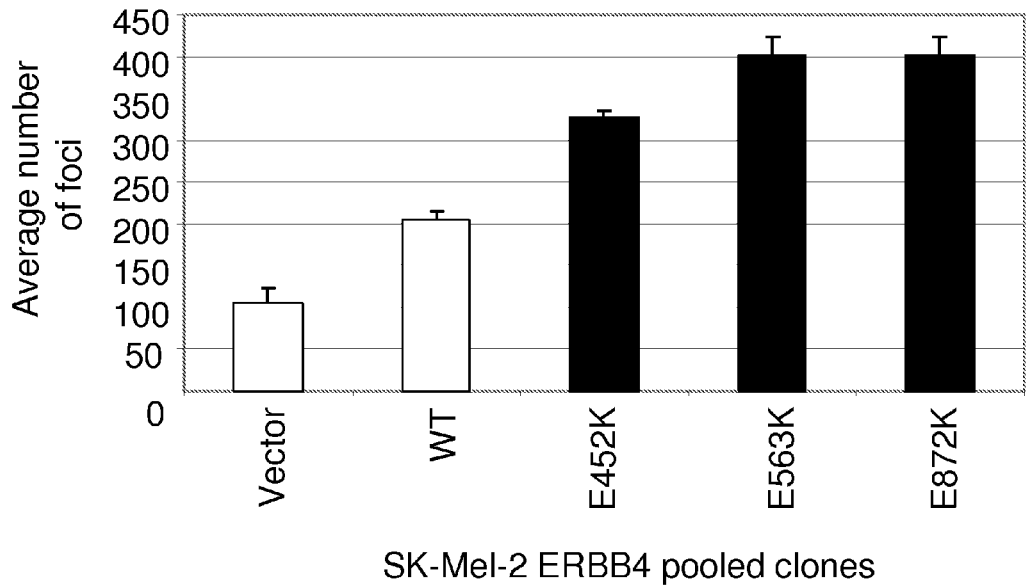
Figure 9B:
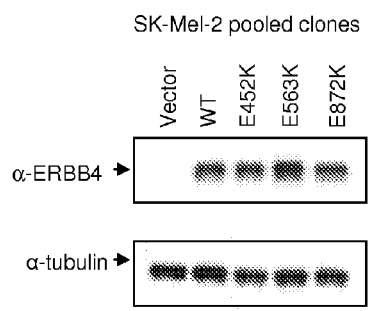
Figure 9C:
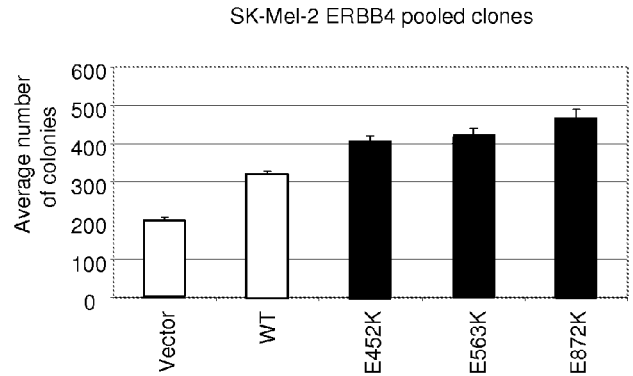

To test the transformation abilities of the ERBB4 mutations in human melanoma cells, stable cell pools expressing vector, WT, and three ERBB4 mutations (E452K, E563K and E872K) were derived in SK-Mel-2 cells, a melanoma cell line that expresses WT ERBB4. Western blot analysis showed a similar expression level of ERBB4 in all clones (FIG. 9B). As seen in FIG. 2B, expression of all the ERBB4 mutants elicited a significantly higher cell transformation ability compared to clones expressing vector or WT ERBB4 (p<0.05, t-test). When the same set of clones was suspended in soft agar, cells expressing mutant ERBB4 formed a significantly higher number of anchorage-independent colonies (p<0.05, t-test, FIG. 9C). Thus, all the tested ERBB4 mutants potently increased both colony formation ability as well as growth on soft agar in all the cell lines compared to vector or WT ERBB4 stable clones.

Example 6

Dependency of MM Lines Harboring ERBB4 Mutations on ERBB4 Signaling

Figure 3A:
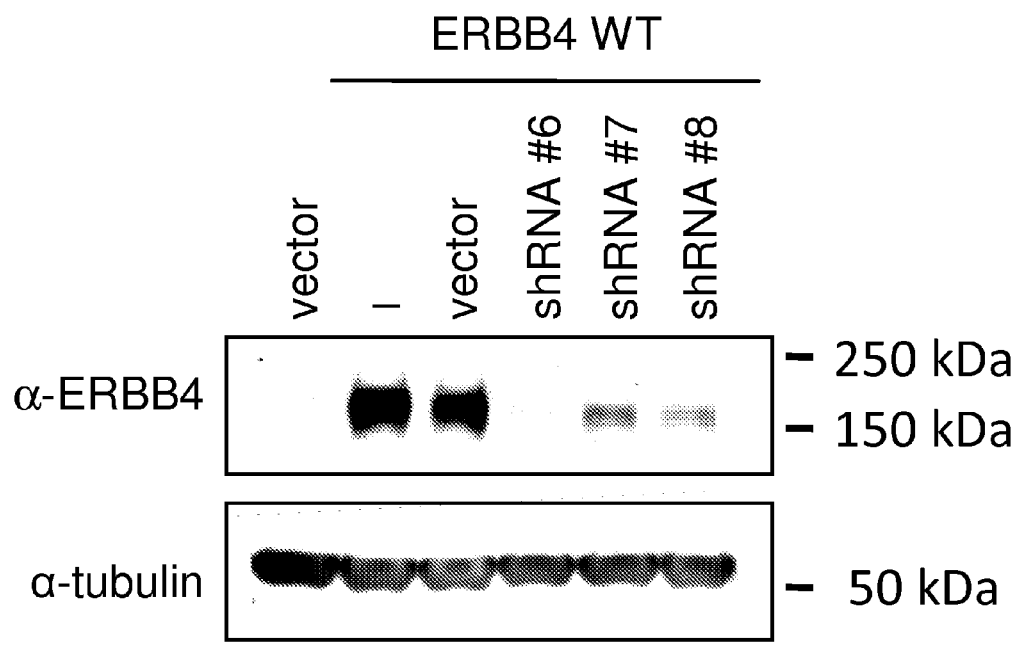
FIG. 3: Expression of mutant ERBB4 provides an essential cell survival signal in melanoma. (A) HEK 293 cells were transiently co-transfected with either vector or WT ERBB4 together with either control vector or shRNAs that target ERBB4. Cell lysates were analyzed by immunoblotting using α-ERBB4. For normalization, lysates were analyzed in parallel by α-tubulin immunoblotting. (B) Cells transduced with shRNA targeting ERBB4 were lysed and immunoprecipitated using α-ERBB4 beads Immunoprecipitates were blotted with specific antibodies, as indicated. (C-G) shRNA-mediated ERBB4 knockdown in melanoma lines containing ERBB4 mutations results in reduced cell growth. Cells were seeded in 96-well plates and incubated for 13-17 days. Plates were analyzed every other day for cell proliferation, where the average cell number at each time point was measured by determining DNA content using SYBR Green I. Melanoma cells harboring ERBB4 mutations stably transduced with shRNA constructs targeting ERBB4, but not those stably transduced with the control vector only, showed decreased growth relative to control. This did not occur in melanoma cells harboring WT ERBB4.
Figure 3B:
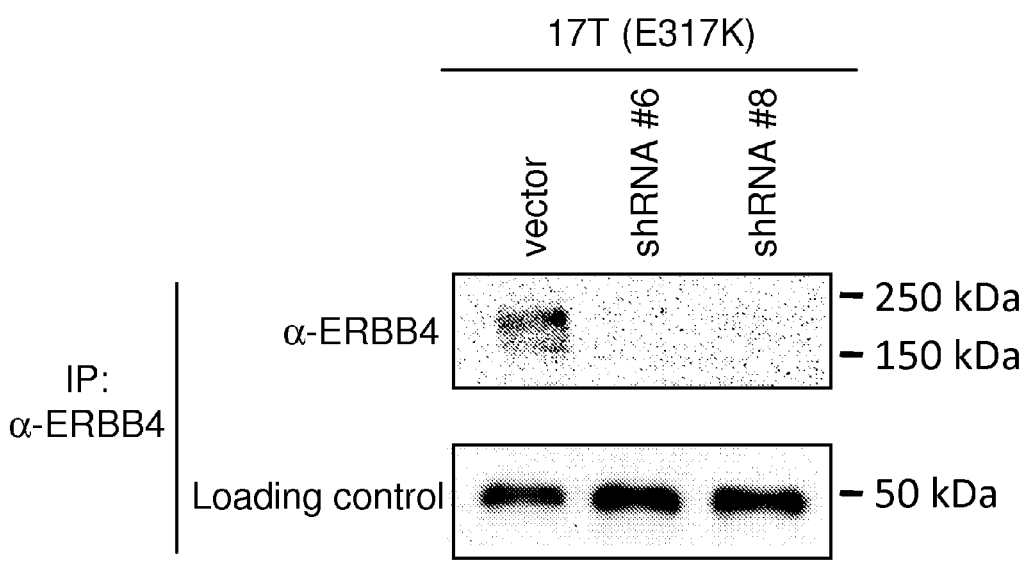
Figure 3C:
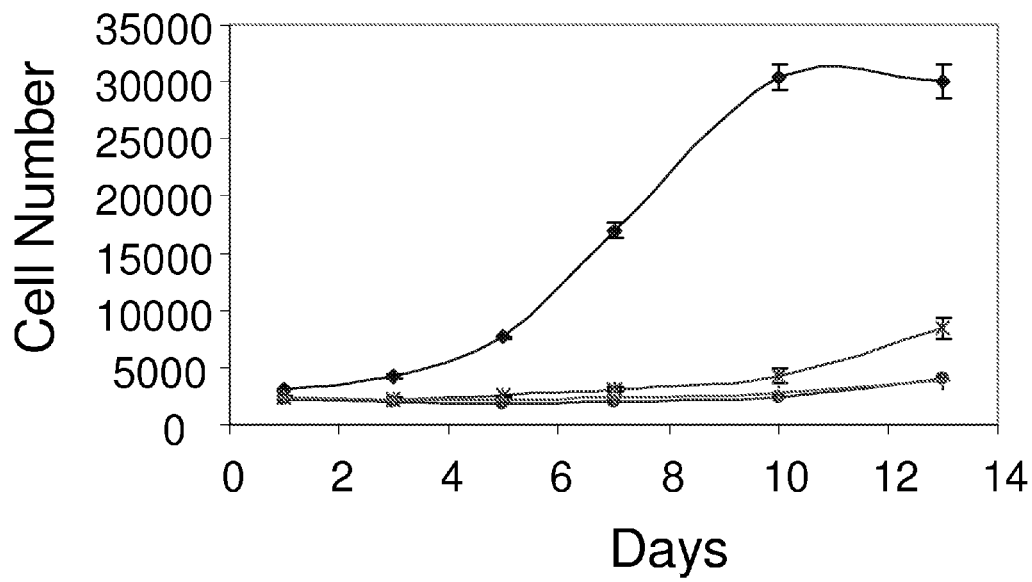
Figure 3D:
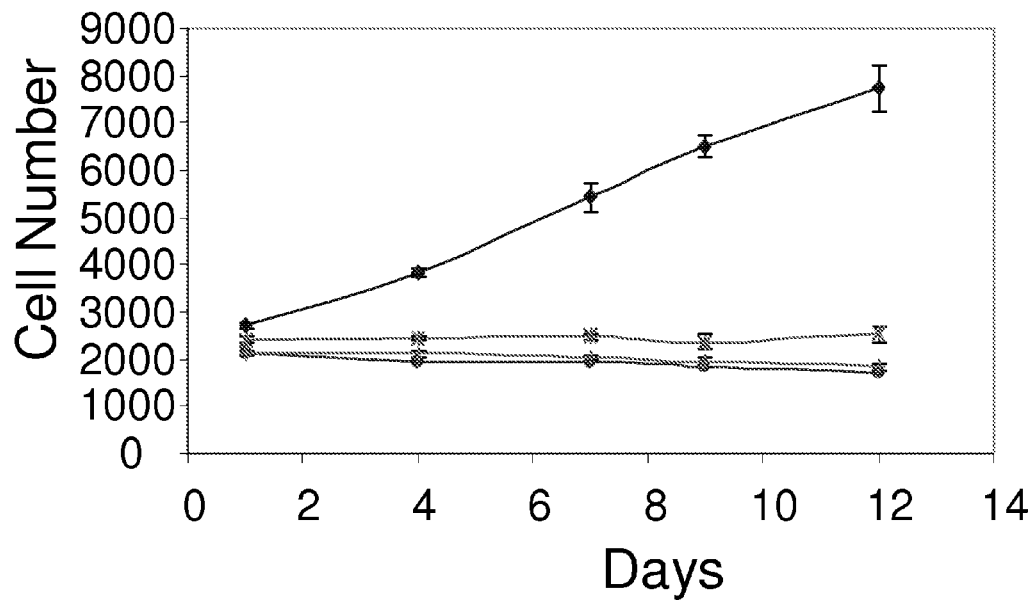
Figure 3F:
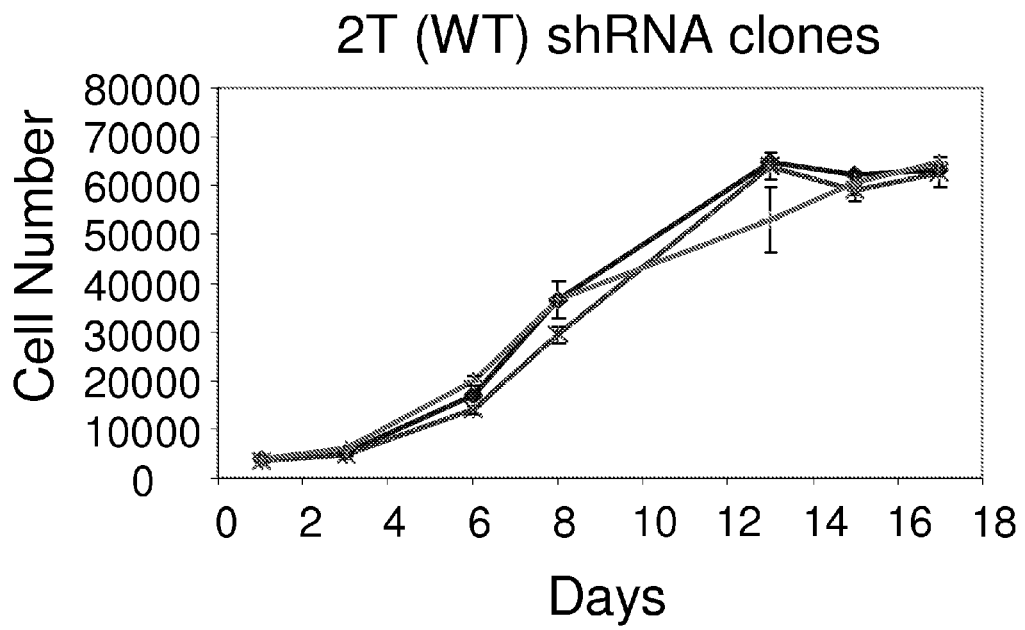
Figure 3G:
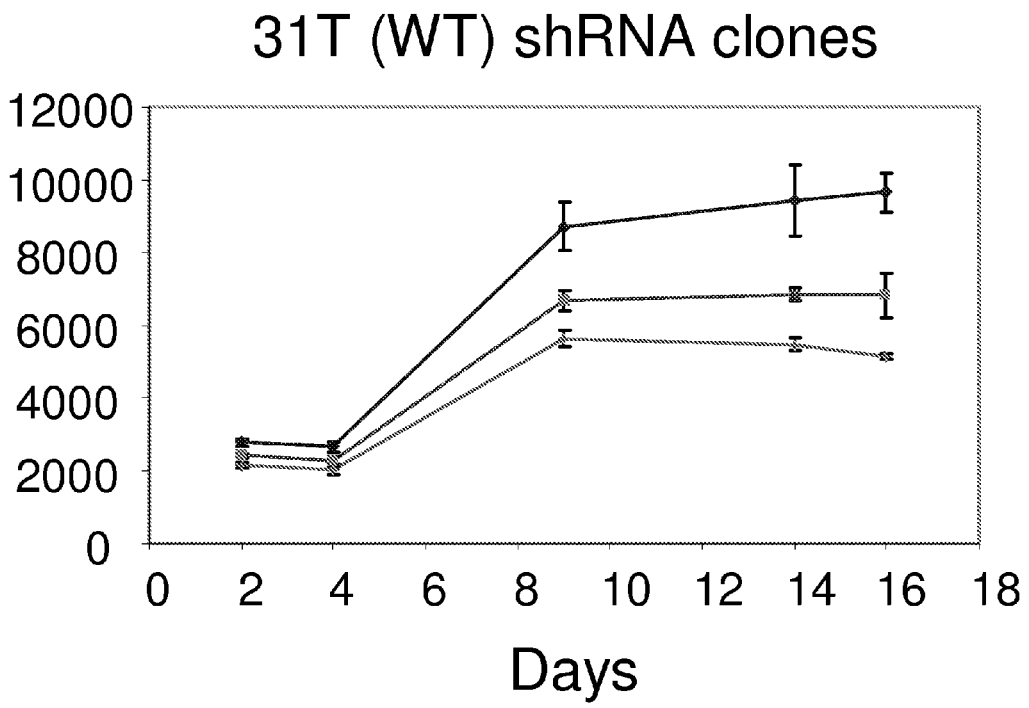
Figure 12:
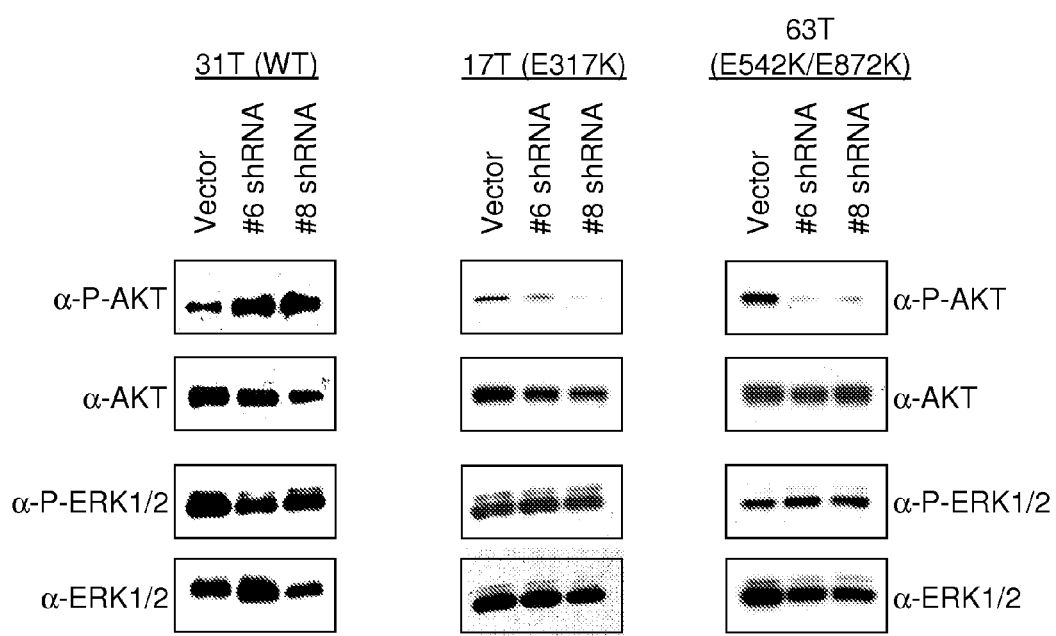
FIG. 12: Knockdown of ERBB4 protein causes reduced activation of the AKT pathway but not of the ERK pathway. Melanoma cells lines containing either WT or mutant ERBB4 were harvested and analyzed by western blot. Shown are immunoblots of lysates probed with the indicated antibodies.

This example describes the effect of inhibiting expression of WT and mutant ERBB4 using shRNA. In order to assess if melanoma cells harboring endogenous ERBB4 mutations are dependent on ERBB4 signaling for proliferation, short hairpin RNA (shRNA) was used to stably knockdown ERBB4 protein levels in melanoma lines harboring either WT (2T and 31T) or mutant ERBB4 (17T, E317K; 63T, E542K/E872K; or 7T, E452K). Specific targeting of ERBB4 by shRNAs was confirmed both in transfected HEK 293 cells and in one of the melanoma cell lines by immunoblotting (FIGS. 3A-3B). Three unique shRNA constructs targeting ERBB4 had minimal effect on the proliferation of cells expressing WT receptor, but significantly reduced the growth of melanoma lines containing mutant ERBB4 (FIGS. 3C-3G). Thus, mutant ERBB4 is essential for growth of melanomas harboring these mutations. Evaluation of the effects of ERBB4 knockdown on downstream signaling pathways revealed that down-regulation of ERBB4 in cells harboring mutant versions of the gene reduces levels of endogenous, phosphorylated AKT, but not of phosphorylated ERK. In contrast, inhibition of ERBB4 expression in cells harboring WT versions of the gene showed similar levels of AKT and ERK activation (FIG. 12).

Because shRNA-mediated cell death could result from specific or nonspecific effects, an exogenous, non-targetable WT ERBB4 construct (NT ERBB4), engineered to be resistant to knockdown by the introduction of three silent mutations in the region of ERBB4 targeted by shRNA #6, was examined for the ability to rescue the effects of knockdown of endogenous ERBB4. Melanoma cells harboring the E317K mutation stably expressing either control or ERBB4 shRNA #6 construct were transduced with the lentiviral NT ERBB4 construct or empty vector as control. Similar phosphotyrosine content is observed in both WT and NT ERBB4 constructs, demonstrating that the silent mutations in the NT construct do not affect the ability of the receptor to be phosphorylated to wild-type levels (FIG. 13A). Importantly, pooled clones of NT reconstituted cells were markedly more resistant to growth inhibition induced by ERBB4 knockdown (#6/NT) than shRNA control-infected cells (Vect/Vect).

Figures 10A, 10B:
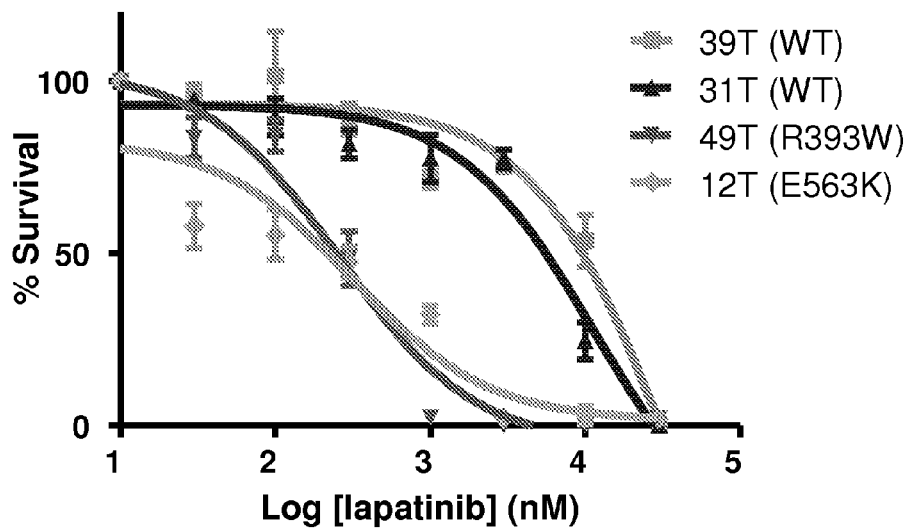
FIG. 10: Melanoma lines expressing ERBB4 mutants exhibit increased sensitivity to ERBB inhibition by lapatinib. (A) Representative dose response curves showing lapatinib efficacy against ERBB4 mutant cell lines compared to WT ERBB4 cell lines. Cells were treated for 72 hours in the presence of increasing concentrations (0.01-30 µM) of lapatinib, and relative cell number was estimated by methylene blue protein staining and plotted as percent survival when compared to vehicle-treated control versus Log (lapatinib) nM (where 1 is 10 nM lapatinib). Fitted lines were generated using 4-parameter nonlinear regression via GraphPad Prism. (B) ERBB4 mutant cells lines have increased sensitivity to lapatinib compared to WT ERBB4 cell lines. The $IC_{50}$ values for inhibition of cell growth by 72 hour treatment with lapatinib of a larger panel of lines harboring WT and mutant ERBB4 were analyzed using GraphPad Prism v.5 (n=3). (C) Immunoprecipitation and western blot analysis of ERBB4 autophosphorylation in cells treated with lapatinib. Cells were treated for 1 hour with lapatinib or vehicle alone as control. Lysates were immunoprecipitated with α-ERBB4 followed by western blot analysis with α-ERBB4 and α-P-ERBB4 (Y1162). (D) Melanoma lines expressing mutant ERBB4 exhibit increased lapatinib sensitivity with respect to ERBB4 and AKT phosphorylation. The activity of ERBB4, AKT and ERBB2 was determined by immunoblotting with phospho-specific antibodies. Cells were treated for 1 hour with 5 µM lapatinib or vehicle alone. Lysates were immunoprecipitated using α-ERBB2 or α-ERBB4. Lysates and immunoprecipitates were analyzed by western blotting using the indicated antibodies. Shown are representative blots. (E) Quantitative assessment of data from 2 cell lines harboring WT ERBB4 and 3 cell lines harboring mutant ERBB4 that were performed similarly to (D). The ratio of band intensities of (P-Y1162)-ERBB4/ERBB4, (P)-S473-AKT/AKT and (P-Y1248)-ERBB2/ERBB2 for each cell line are shown. (F) Mutant ERBB4 cells have increased sub-G1 population in the presence of lapatinib compared to WT ERBB4 cells. Shown are representative plots of FACS analysis of 31T (WT) and 12T (E563K) showing cell cycle distribution (PI staining, x-axis) versus cell counts (y-axis). (G) Quantitation of FACS-sorted lapatinib-treated cells. The percent apoptotic cells were determined based on the sub-G1 population for vehicle-treated cells or lapatinib-treated cells.
Figure 10C:
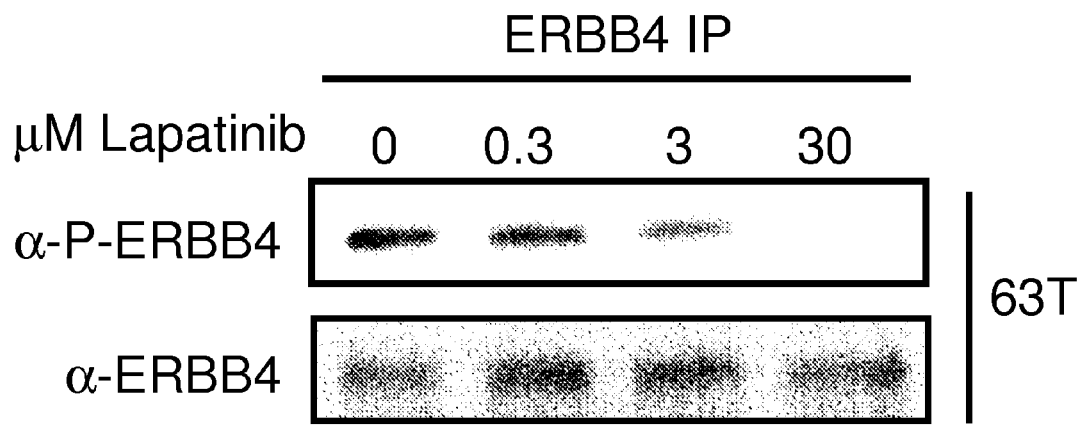
Figure 10D:
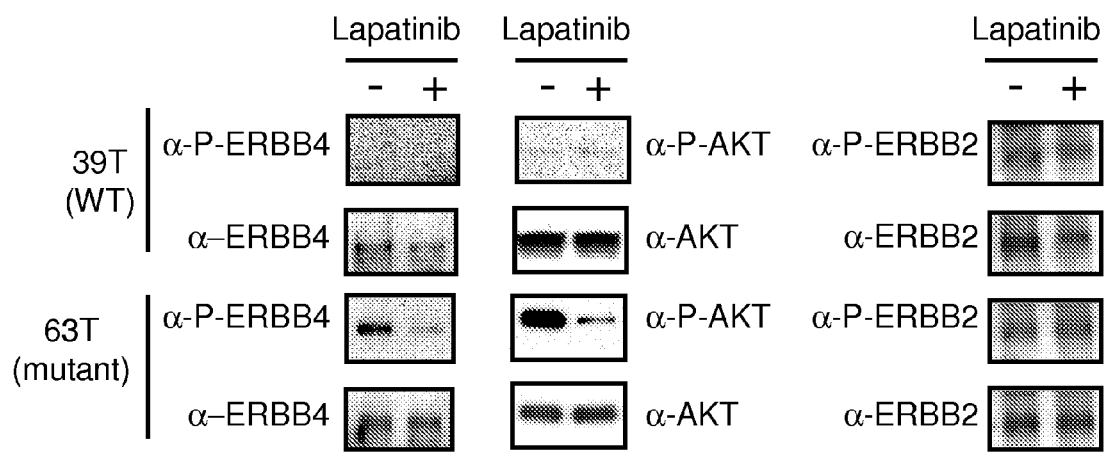
Figure 10E:
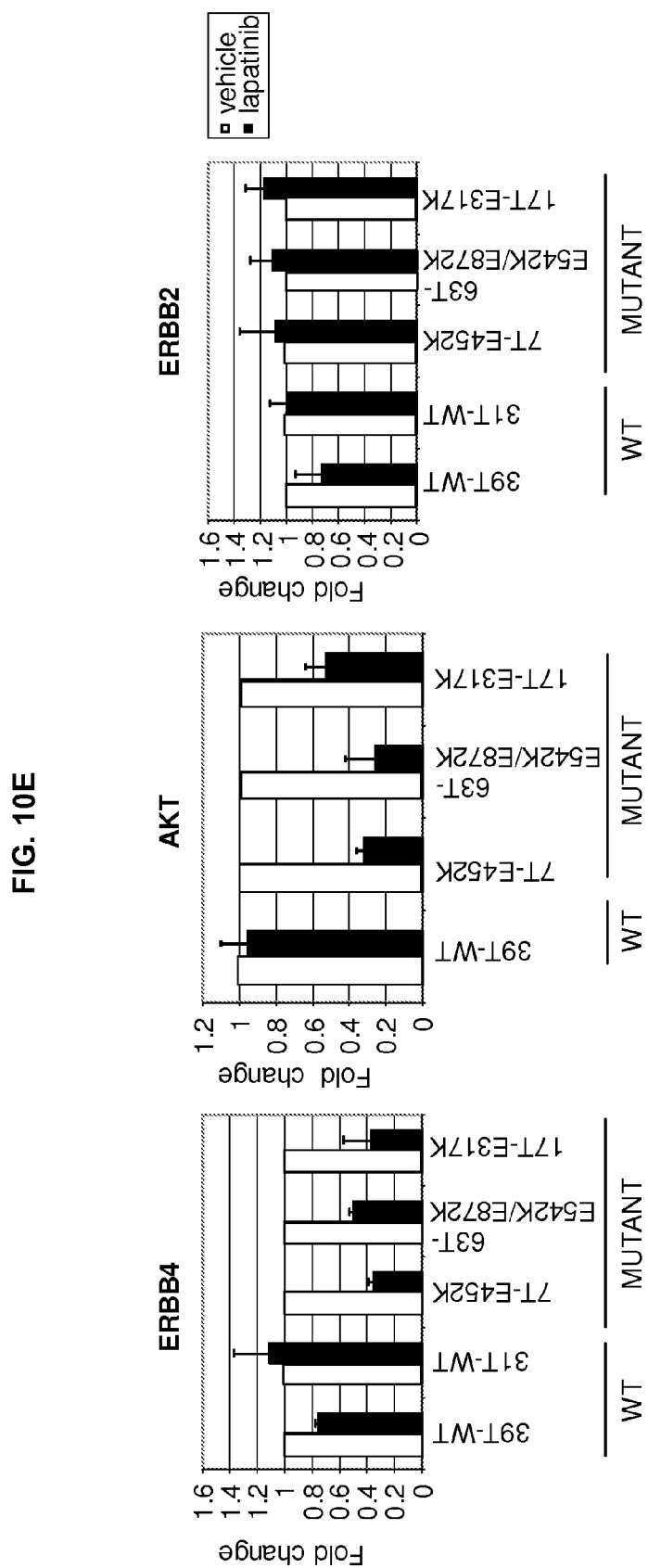
Figure 14A:
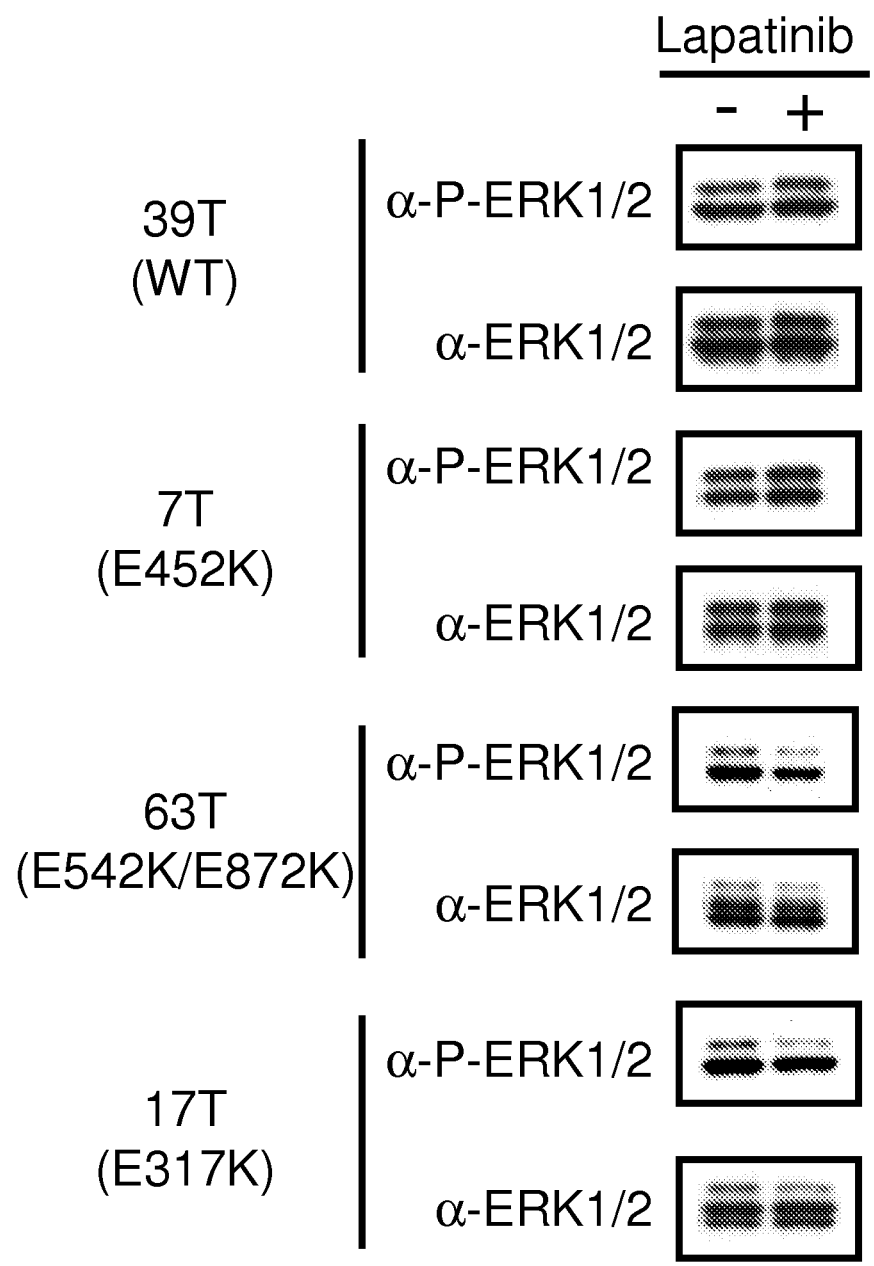
FIG. 14: Effect of lapatinib in ERK1/2 signaling pathways. (A) Melanoma lines expressing mutant ERBB4 exhibit increased lapatinib sensitivity with respect to ERK1 and ERK2 phosphorylation. Cells were treated for 72 hours with 5 μM lapatinib or vehicle as control. The activity of ERK1 and ERK2 was determined by immunoblotting with phospho-specific antibodies. Total ERK protein was also determined by immunoblotting. Shown are representative blots. (B) Quantitative assessment of data from one melanoma cell line harboring mutant ERBB4. The ratio of band intensities of P-ERK1/ERK1 or P-ERK2/ERK2 was analyzed for each melanoma cell line.
Figure 14B:
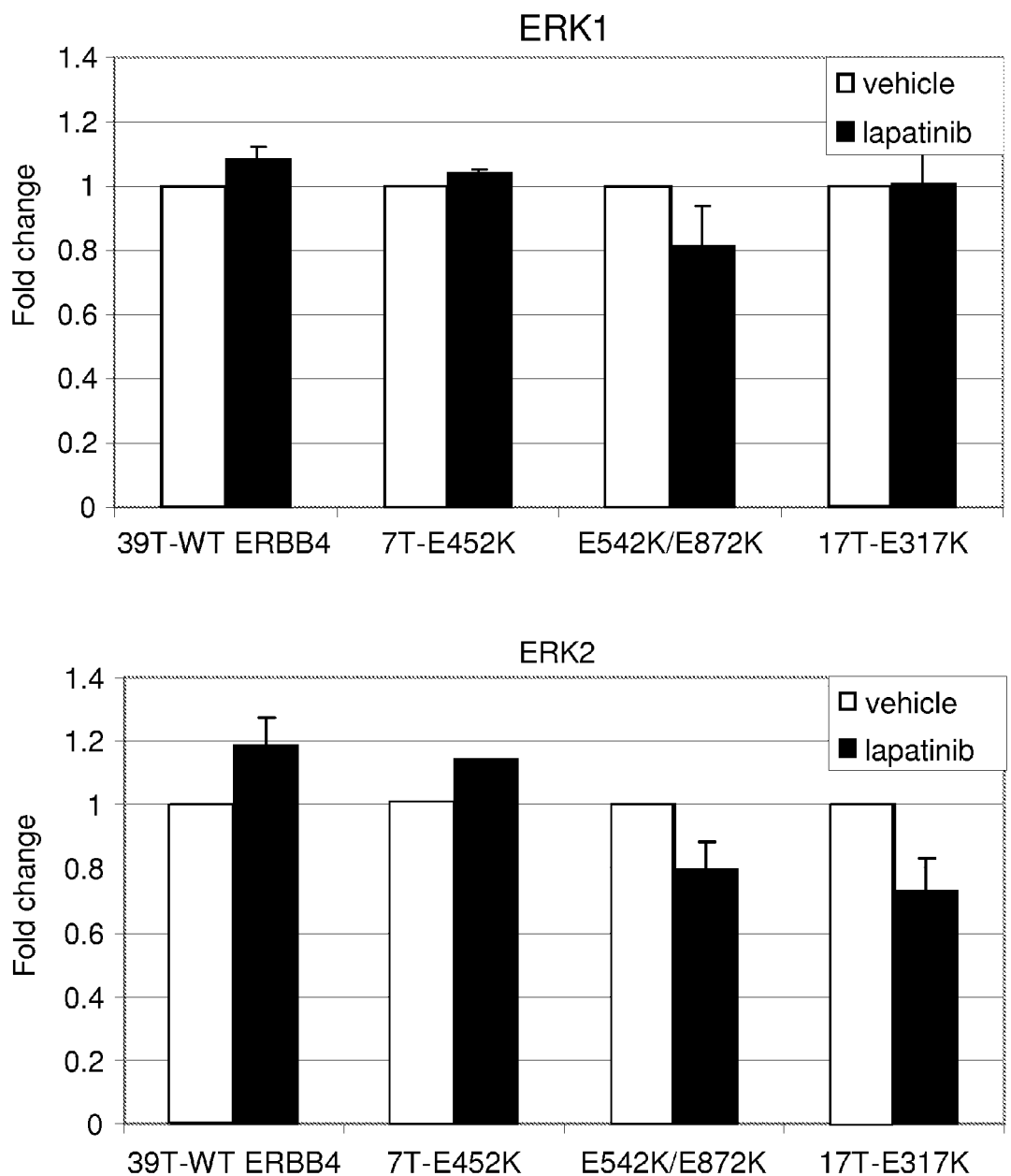

To evaluate mutant ERBB4 as a potential target for specific inhibition of melanoma cell survival, the ERBB4 pathway was targeted with the FDA-approved pan-ERBB pharmacologic inhibitor, lapatinib (GW2016) (Heymach et al., *Clin. Cancer Res.* 12:4441s-4445s, 2006). Exposure of melanoma cells to lapatinib resulted in reduced cell proliferation to a greater extent in cells containing endogenous ERBB4 mutations than in cells containing endogenous WT ERBB4 (FIG. 10A). An $IC_{50}$ calculation revealed that melanoma cells harboring ERBB4 mutations were 10- to 250-fold more sensitive to lapatinib than cells with WT receptor (FIG. 10B) and treatment with lapatinib inhibited receptor autophosphorylation in a dose-dependent manner (FIG. 10C). This increased sensitivity to lapatinib was accompanied by specific inhibition of ERBB4 and AKT activation in cells harboring mutant ERBB4 (FIGS. 10D-10E). Activation of other downstream elements, such as ERK, was also slightly inhibited by lapatinib (FIGS. 14A-14B). Thus, although signaling by mutant ERBB4 demonstrates selective activation of AKT, lapatinib treatment of cells harboring mutant ERRB4 results in uniform inhibition of downstream signaling pathways. Only mutant ERBB4 was inhibited by lapatinib in the melanoma cell lines. No inhibition of its family member ERBB2 was observed (FIGS. 10D-10E) and no phosphorylation of EGFR was observed in any of these cells. The observed reduced proliferation occurred in cells harboring BRAF, NRAS, ARAF or CRAF mutations in addition to the ERBB4 mutations.

TABLE 5

Mutations identified in RAF and RAS isoforms

| Sample | ERBB4 | BRAF | NRAS | ARAF | CRAF | HRAS | KRAS |
|---|---|---|---|---|---|---|---|
| 7T | E452K | wt | Q61R | wt | wt | wt | wt |
| 12T | E563K | wt | Q61Q/R | wt | wt | wt | wt |
| 17T | E317K | wt | Q61Q/K | wt | wt | wt | wt |
| 31T | wt | wt | wt | wt | wt | wt | wt |
| 34T | R491K | V600V/E | wt | wt | T362T/A | wt | wt |
| 39T | wt | | wt | wt | wt | wt | wt |
| 49T | R393R/W | V600V/E | wt | wt | wt | wt | wt |
| 55T | E452K | V600V/E | wt | P216S P254L | wt | wt | wt |
| 56T | R544R/W | V600V/E | wt | wt | wt | wt | wt |
| 63T | E542K E872K | wt | Q61Q/K | wt | wt | wt | wt |
| 68T | Splice site LOH | V600V/E | wt | wt | wt | wt | wt |
| 71T | L39L/F S1246S/N | V600V/M V600V/E | wt | wt | wt | wt | wt |
| 86T | E836E/K | V600V/E | wt | wt | wt | wt | wt |
| 93T | wt | wt | wt | A345A/G | wt | wt | wt |

Figure 10F:
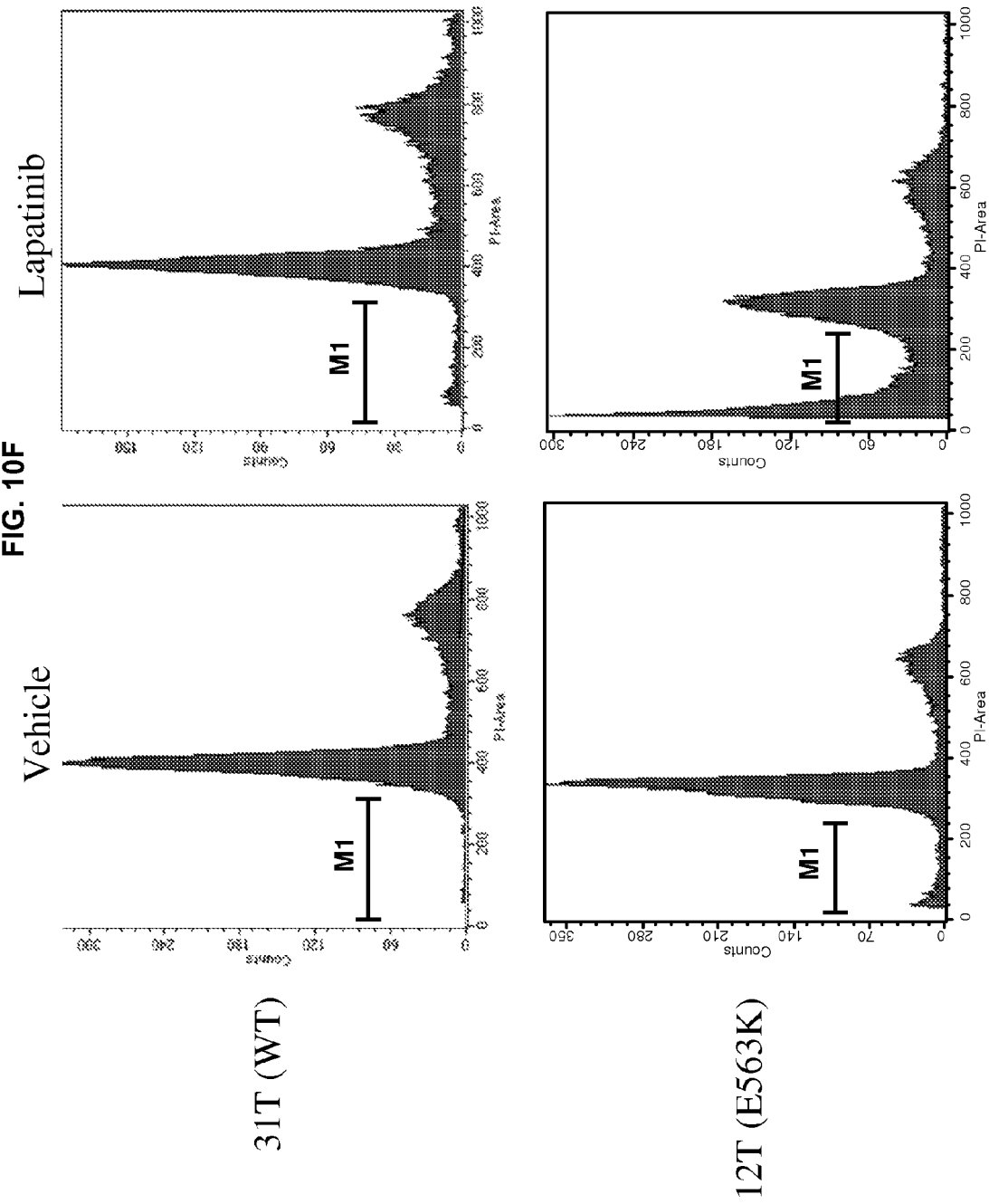
Figure 10G:
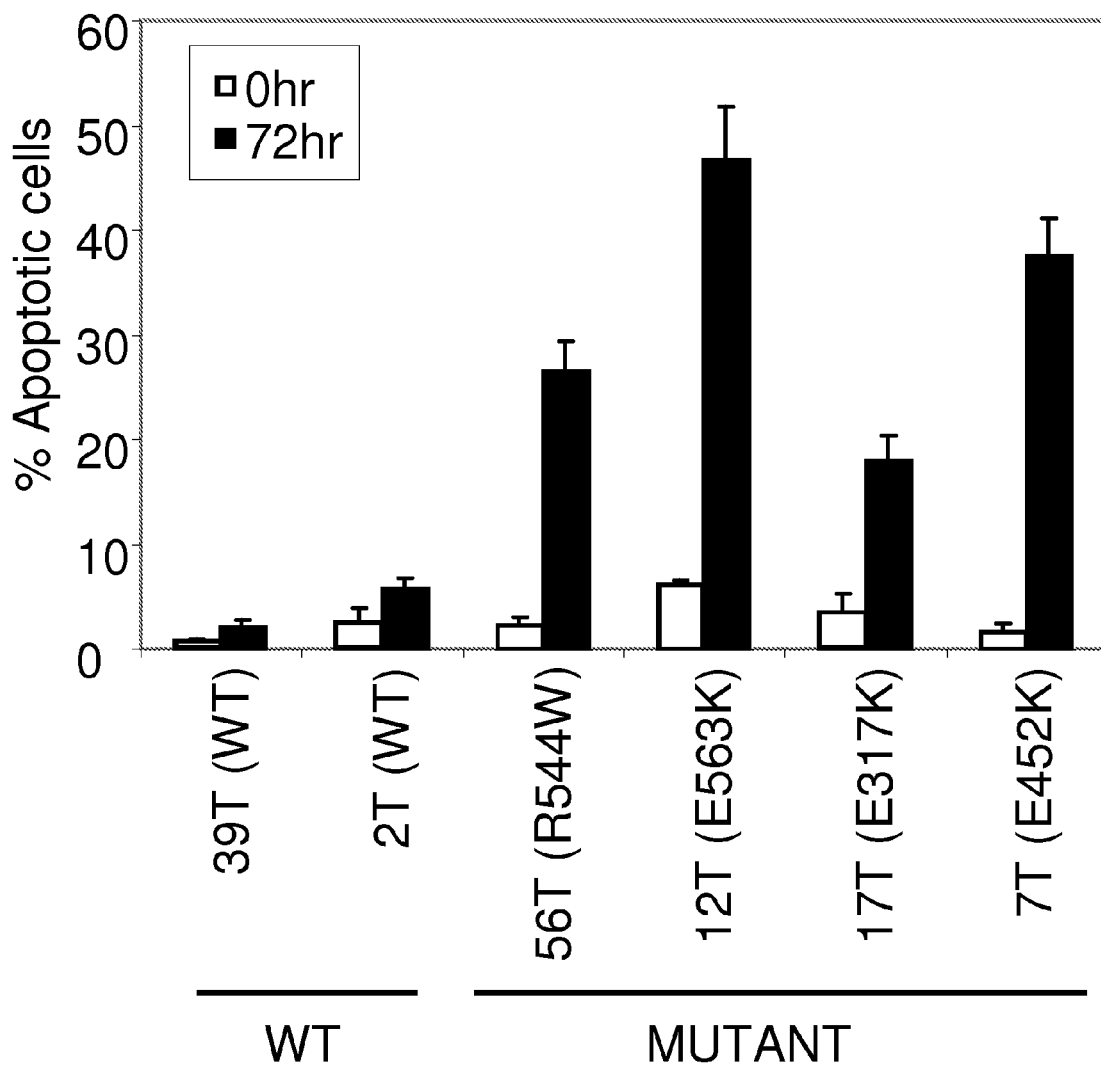

To elucidate the mechanism of decreased growth of cells expressing mutant ERBB4 following lapatinib treatment, cells were examined for cell cycle perturbations or apoptosis by flow cytometry. Lapatinib markedly increased apoptosis of melanoma cells harboring mutant ERBB4 compared to lines harboring WT ERBB4 (FIGS. 10E-10G). Thus, expression of mutant ERBB4 appears essential for suppression of pro-apoptotic signals in melanoma cells harboring these mutations, which is consistent with the selective activation of AKT in ERBB4 mutant cells (FIGS. 11A-11B) and previous results demonstrating an anti-apoptotic role for AKT (Grant et al., *Front. Biosci.* 7:d76-89, 2002). These results suggest that lapatinib preferentially inhibits mutant ERBB4 signaling and that cells with ERBB4 mutations are subject to "oncogene addiction" (Weinstein, *Science* 297:63-64, 2002). Moreover, the enhanced AKT signaling in cells with mutant ERBB4 may provide an additional therapeutic target in these tumors.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of selecting a subject diagnosed with melanoma as a candidate for treatment with an ERBB4 inhibitor, a PI3K/AKT pathway inhibitor, or both, comprising:
   (a) detecting the presence or absence of a mutation in the ERBB4 gene in a melanoma sample from the subject, wherein the mutation is selected from G949A, G1354A, G1624A, C1630T, G1687A, G2506A and G2614A (numbered with reference to SEQ ID NO: 1), and wherein the presence of the mutation in the ERBB4 gene indicates that the subject is a candidate for treatment with an ERBB4 inhibitor, a PI3K/AKT pathway inhibitor, or both; and
   (b) administering to the subject an ERBB4 inhibitor, a PI3K/AKT pathway inhibitor, or both when the mutation in the ERBB4 gene is present in the sample from the subject.

2. The method of claim 1, wherein the subject is administered an ERBB4 inhibitor and a PI3K/AKT pathway inhibitor.

3. The method of claim 1, wherein the ERBB4 inhibitor is lapatinib.

4. The method of claim 1, wherein detecting the presence or absence of a mutation in the ERBB4 gene in a melanoma sample from the subject comprises polymerase chain reaction amplification of genomic DNA from the melanoma sample using ERBB4-specific primers.

5. The method of claim 4, further comprising DNA sequencing of the amplified genomic DNA.

* * * * *

```
                              SEQUENCE LISTING

<160> NUMBER OF SEQ ID NOS: 79

<210> SEQ ID NO 1
<211> LENGTH: 3927
<212> TYPE: DNA
<213> ORGANISM: Homo sapiens
<220> FEATURE:
<221> NAME/KEY: CDS
<222> LOCATION: (1)..(3927)
<220> FEATURE:
<221> NAME/KEY: misc_feature
<222> LOCATION: (949)..(949)
<223> OTHER INFORMATION: n = g or a
<220> FEATURE:
<221> NAME/KEY: misc_feature
<222> LOCATION: (1354)..(1354)
<223> OTHER INFORMATION: n = g or a
<220> FEATURE:
<221> NAME/KEY: misc_feature
<222> LOCATION: (1624)..(1624)
<223> OTHER INFORMATION: n = g or a
<220> FEATURE:
<221> NAME/KEY: misc_feature
<222> LOCATION: (1630)..(1630)
<223> OTHER INFORMATION: n = c or t
<220> FEATURE:
<221> NAME/KEY: misc_feature
<222> LOCATION: (1687)..(1687)
<223> OTHER INFORMATION: n = g or a
<220> FEATURE:
<221> NAME/KEY: misc_feature
<222> LOCATION: (2506)..(2506)
<223> OTHER INFORMATION: n = g or a
<220> FEATURE:
<221> NAME/KEY: misc_feature
<222> LOCATION: (2614)..(2614)
<223> OTHER INFORMATION: n = g or a

<400> SEQUENCE: 1 atg aag ccg gcg aca gga ctt tgg gtc tgg gtg agc ctt ctc gtg gcg     48
Met Lys Pro Ala Thr Gly Leu Trp Val Trp Val Ser Leu Leu Val Ala
1               5                   10                  15 gcg ggg acc gtc cag ccc agc gat tct cag tca gtg tgt gca gga acg     96
Ala Gly Thr Val Gln Pro Ser Asp Ser Gln Ser Val Cys Ala Gly Thr
                20                  25                  30 gag aat aaa ctg agc tct ctc tct gac ctg gaa cag cag tac cga gcc    144
Glu Asn Lys Leu Ser Ser Leu Ser Asp Leu Glu Gln Gln Tyr Arg Ala
            35                  40                  45 ttg cgc aag tac tat gaa aac tgt gag gtt gtc atg ggc aac ctg gag    192
Leu Arg Lys Tyr Tyr Glu Asn Cys Glu Val Val Met Gly Asn Leu Glu
        50                  55                  60 ata acc agc att gag cac aac cgg gac ctc tcc ttc ctg cgg tct gtt    240
Ile Thr Ser Ile Glu His Asn Arg Asp Leu Ser Phe Leu Arg Ser Val
65                  70                  75                  80
```

```
cga gaa gtc aca ggc tac gtg tta gtg gct ctt aat cag ttt cgt tac      288
Arg Glu Val Thr Gly Tyr Val Leu Val Ala Leu Asn Gln Phe Arg Tyr
             85                  90                  95 ctg cct ctg gag aat tta cgc att att cgt ggg aca aaa ctt tat gag      336
Leu Pro Leu Glu Asn Leu Arg Ile Ile Arg Gly Thr Lys Leu Tyr Glu
            100                 105                 110 gat cga tat gcc ttg gca ata ttt tta aac tac aga aaa gat gga aac      384
Asp Arg Tyr Ala Leu Ala Ile Phe Leu Asn Tyr Arg Lys Asp Gly Asn
        115                 120                 125 ttt gga ctt caa gaa ctt gga tta aag aac ttg aca gaa atc cta aat      432
Phe Gly Leu Gln Glu Leu Gly Leu Lys Asn Leu Thr Glu Ile Leu Asn
    130                 135                 140 ggt gga gtc tat gta gac cag aac aaa ttc ctt tgt tat gca gac acc      480
Gly Gly Val Tyr Val Asp Gln Asn Lys Phe Leu Cys Tyr Ala Asp Thr
145                 150                 155                 160 att cat tgg caa gat att gtt cgg aac cca tgg cct tcc aac ttg act      528
Ile His Trp Gln Asp Ile Val Arg Asn Pro Trp Pro Ser Asn Leu Thr
                165                 170                 175 ctt gtg tca aca aat ggt agt tca gga tgt gga cgt tgc cat aag tcc      576
Leu Val Ser Thr Asn Gly Ser Ser Gly Cys Gly Arg Cys His Lys Ser
            180                 185                 190 tgt act ggc cgt tgc tgg gga ccc aca gaa aat cat tgc cag act ttg      624
Cys Thr Gly Arg Cys Trp Gly Pro Thr Glu Asn His Cys Gln Thr Leu
        195                 200                 205 aca agg acg gtg tgt gca gaa caa tgt gac ggc aga tgc tac gga cct      672
Thr Arg Thr Val Cys Ala Glu Gln Cys Asp Gly Arg Cys Tyr Gly Pro
    210                 215                 220 tac gtc agt gac tgc tgc cat cga gaa tgt gct gga ggc tgc tca gga      720
Tyr Val Ser Asp Cys Cys His Arg Glu Cys Ala Gly Gly Cys Ser Gly
225                 230                 235                 240 cct aag gac aca gac tgc ttt gcc tgc atg aat ttc aat gac agt gga      768
Pro Lys Asp Thr Asp Cys Phe Ala Cys Met Asn Phe Asn Asp Ser Gly
                245                 250                 255 gca tgt gtt act cag tgt ccc caa acc ttt gtc tac aat cca acc acc      816
Ala Cys Val Thr Gln Cys Pro Gln Thr Phe Val Tyr Asn Pro Thr Thr
            260                 265                 270 ttt caa ctg gag cac aat ttc aat gca aag tac aca tat gga gca ttc      864
Phe Gln Leu Glu His Asn Phe Asn Ala Lys Tyr Thr Tyr Gly Ala Phe
        275                 280                 285 tgt gtc aag aaa tgt cca cat aac ttt gtg gta gat tcc agt tct tgt      912
Cys Val Lys Lys Cys Pro His Asn Phe Val Val Asp Ser Ser Ser Cys
    290                 295                 300 gtg cgt gcc tgc cct agt tcc aag atg gaa gta gaa naa aat ggg att      960
Val Arg Ala Cys Pro Ser Ser Lys Met Glu Val Glu Xaa Asn Gly Ile
305                 310                 315                 320 aaa atg tgt aaa cct tgc act gac att tgc cca aaa gct tgt gat ggc     1008
Lys Met Cys Lys Pro Cys Thr Asp Ile Cys Pro Lys Ala Cys Asp Gly
                325                 330                 335 att ggc aca gga tca ttg atg tca gct cag act gtg gat tcc agt aac     1056
Ile Gly Thr Gly Ser Leu Met Ser Ala Gln Thr Val Asp Ser Ser Asn
            340                 345                 350 att gac aaa ttc ata aac tgt acc aag atc aat ggg aat ttg atc ttt     1104
Ile Asp Lys Phe Ile Asn Cys Thr Lys Ile Asn Gly Asn Leu Ile Phe
        355                 360                 365 cta gtc act ggt att cat ggg gac cct tac aat gca att gaa gcc ata     1152
Leu Val Thr Gly Ile His Gly Asp Pro Tyr Asn Ala Ile Glu Ala Ile
    370                 375                 380 gac cca gag aaa ctg aac gtc ttt cgg aca gtc aga gag ata aca ggt     1200
Asp Pro Glu Lys Leu Asn Val Phe Arg Thr Val Arg Glu Ile Thr Gly
385                 390                 395                 400
```

```
ttc ctg aac ata cag tca tgg cca cca aac atg act gac ttc agt gtt   1248
Phe Leu Asn Ile Gln Ser Trp Pro Pro Asn Met Thr Asp Phe Ser Val
            405                 410                 415 ttt tct aac ctg gtg acc att gga aga gta ctc tat agt ggc ctg        1296
Phe Ser Asn Leu Val Thr Ile Gly Gly Arg Val Leu Tyr Ser Gly Leu
        420                 425                 430 tcc ttg ctt atc ctc aag caa cag ggc atc acc tct cta cag ttc cag    1344
Ser Leu Leu Ile Leu Lys Gln Gln Gly Ile Thr Ser Leu Gln Phe Gln
            435                 440                 445 tcc ctg aag naa atc agc gca gga aac atc tat att act gac aac agc    1392
Ser Leu Lys Xaa Ile Ser Ala Gly Asn Ile Tyr Ile Thr Asp Asn Ser
        450                 455                 460 aac ctg tgt tat tat cat acc att aac tgg aca aca ctc ttc agc aca    1440
Asn Leu Cys Tyr Tyr His Thr Ile Asn Trp Thr Thr Leu Phe Ser Thr
465                 470                 475                 480 atc aac cag aga ata gta atc cgg gac aac aga aaa gct gaa aat tgt    1488
Ile Asn Gln Arg Ile Val Ile Arg Asp Asn Arg Lys Ala Glu Asn Cys
            485                 490                 495 act gct gaa gga atg gtg tgc aac cat ctg tgt tcc agt gat ggc tgt    1536
Thr Ala Glu Gly Met Val Cys Asn His Leu Cys Ser Ser Asp Gly Cys
        500                 505                 510 tgg gga cct ggg cca gac caa tgt ctg tcg tgt cgc cgc ttc agt aga    1584
Trp Gly Pro Gly Pro Asp Gln Cys Leu Ser Cys Arg Arg Phe Ser Arg
            515                 520                 525 gga agg atc tgc ata gag tct tgt aac ctc tat gat ggt naa ttt ngg    1632
Gly Arg Ile Cys Ile Glu Ser Cys Asn Leu Tyr Asp Gly Xaa Phe Xaa
        530                 535                 540 gag ttt gag aat ggc tcc atc tgt gtg gag tgt gac ccc cag tgt gag    1680
Glu Phe Glu Asn Gly Ser Ile Cys Val Glu Cys Asp Pro Gln Cys Glu
545                 550                 555                 560 aag atg naa gat ggc ctc ctc aca tgc cat gga ccg ggt cct gac aac    1728
Lys Met Xaa Asp Gly Leu Leu Thr Cys His Gly Pro Gly Pro Asp Asn
            565                 570                 575 tgt aca aag tgc tct cat ttt aaa gat ggc cca aac tgt gtg gaa aaa    1776
Cys Thr Lys Cys Ser His Phe Lys Asp Gly Pro Asn Cys Val Glu Lys
        580                 585                 590 tgt cca gat ggc tta cag ggg gca aac agt ttc att ttc aag tat gct    1824
Cys Pro Asp Gly Leu Gln Gly Ala Asn Ser Phe Ile Phe Lys Tyr Ala
            595                 600                 605 gat cca gat cgg gag tgc cac cca tgc cat cca aac tgc acc caa ggg    1872
Asp Pro Asp Arg Glu Cys His Pro Cys His Pro Asn Cys Thr Gln Gly
        610                 615                 620 tgt aac ggt ccc act agt cat gac tgc att tac tac cca tgg acg ggc    1920
Cys Asn Gly Pro Thr Ser His Asp Cys Ile Tyr Tyr Pro Trp Thr Gly
625                 630                 635                 640 cat tcc act tta cca caa cat gct aga act ccc ctg att gca gct gga    1968
His Ser Thr Leu Pro Gln His Ala Arg Thr Pro Leu Ile Ala Ala Gly
            645                 650                 655 gta att ggt ggg ctc ttc att ctg gtc att gtg ggt ctg aca ttt gct    2016
Val Ile Gly Gly Leu Phe Ile Leu Val Ile Val Gly Leu Thr Phe Ala
        660                 665                 670 gtt tat gtt aga agg aag agc atc aaa aag aaa aga gcc ttg aga aga    2064
Val Tyr Val Arg Arg Lys Ser Ile Lys Lys Lys Arg Ala Leu Arg Arg
            675                 680                 685 ttc ttg gaa aca gag ttg gtg gaa cca tta act ccc agt ggc aca gca    2112
Phe Leu Glu Thr Glu Leu Val Glu Pro Leu Thr Pro Ser Gly Thr Ala
        690                 695                 700 ccc aat caa gct caa ctt cgt att ttg aaa gaa act gag ctg aag agg    2160
Pro Asn Gln Ala Gln Leu Arg Ile Leu Lys Glu Thr Glu Leu Lys Arg
705                 710                 715                 720
```

|  |  |
|---|---|
| gta aaa gtc ctt ggc tca ggt gct ttt gga acg gtt tat aaa ggt att<br>Val Lys Val Leu Gly Ser Gly Ala Phe Gly Thr Val Tyr Lys Gly Ile<br>                    725                    730                    735 | 2208 |
| tgg gta cct gaa gga gaa act gtg aag att cct gtg gct att aag att<br>Trp Val Pro Glu Gly Glu Thr Val Lys Ile Pro Val Ala Ile Lys Ile<br>                    740                    745                    750 | 2256 |
| ctt aat gag aca act ggt ccc aag gca aat gtg gag ttc atg gat gaa<br>Leu Asn Glu Thr Thr Gly Pro Lys Ala Asn Val Glu Phe Met Asp Glu<br>                    755                    760                    765 | 2304 |
| gct ctg atc atg gca agt atg gat cat cca cac cta gtc cgg ttg ctg<br>Ala Leu Ile Met Ala Ser Met Asp His Pro His Leu Val Arg Leu Leu<br>                    770                    775                    780 | 2352 |
| ggt gtg tgt ctg agc cca acc atc cag ctg gtt act caa ctt atg ccc<br>Gly Val Cys Leu Ser Pro Thr Ile Gln Leu Val Thr Gln Leu Met Pro<br>785                    790                    795                    800 | 2400 |
| cat ggc tgc ctg ttg gag tat gtc cac gag cac aag gat aac att gga<br>His Gly Cys Leu Leu Glu Tyr Val His Glu His Lys Asp Asn Ile Gly<br>                    805                    810                    815 | 2448 |
| tca caa ctg ctg ctt aac tgg tgt gtc cag ata gct aag gga atg atg<br>Ser Gln Leu Leu Leu Asn Trp Cys Val Gln Ile Ala Lys Gly Met Met<br>                    820                    825                    830 | 2496 |
| tac ctg gaa naa aga cga ctc gtt cat cgg gat ttg gca gcc cgt aat<br>Tyr Leu Glu Xaa Arg Arg Leu Val His Arg Asp Leu Ala Ala Arg Asn<br>                    835                    840                    845 | 2544 |
| gtc tta gtg aaa tct cca aac cat gtg aaa atc aca gat ttt ggg cta<br>Val Leu Val Lys Ser Pro Asn His Val Lys Ile Thr Asp Phe Gly Leu<br>                    850                    855                    860 | 2592 |
| gcc aga ctc ttg gaa gga gat naa aaa gag tac aat gct gat gga gga<br>Ala Arg Leu Leu Glu Gly Asp Xaa Lys Glu Tyr Asn Ala Asp Gly Gly<br>865                      870                    875                    880 | 2640 |
| aag atg cca att aaa tgg atg gct ctg gag tgt ata cat tac agg aaa<br>Lys Met Pro Ile Lys Trp Met Ala Leu Glu Cys Ile His Tyr Arg Lys<br>                    885                    890                    895 | 2688 |
| ttc acc cat cag agt gac gtt tgg agc tat gga gtt act ata tgg gaa<br>Phe Thr His Gln Ser Asp Val Trp Ser Tyr Gly Val Thr Ile Trp Glu<br>                    900                    905                    910 | 2736 |
| ctg atg acc ttt gga gga aaa ccc tat gat gga att cca acg cga gaa<br>Leu Met Thr Phe Gly Gly Lys Pro Tyr Asp Gly Ile Pro Thr Arg Glu<br>                    915                    920                    925 | 2784 |
| atc cct gat tta tta gag aaa gga gaa cgt ttg cct cag cct ccc atc<br>Ile Pro Asp Leu Leu Glu Lys Gly Glu Arg Leu Pro Gln Pro Pro Ile<br>                    930                    935                    940 | 2832 |
| tgc act att gac gtt tac atg gtc atg gtc aaa tgt tgg atg att gat<br>Cys Thr Ile Asp Val Tyr Met Val Met Val Lys Cys Trp Met Ile Asp<br>945                    950                    955                    960 | 2880 |
| gct gac agt aga cct aaa ttt aag gaa ctg gct gct gag ttt tca agg<br>Ala Asp Ser Arg Pro Lys Phe Lys Glu Leu Ala Ala Glu Phe Ser Arg<br>                    965                    970                    975 | 2928 |
| atg gct cga gac cct caa aga tac cta gtt att cag ggt gat gat cgt<br>Met Ala Arg Asp Pro Gln Arg Tyr Leu Val Ile Gln Gly Asp Asp Arg<br>                    980                    985                    990 | 2976 |
| atg aag ctt ccc agt cca aat gac agc aag ttc ttt cag aat ctc ttg<br>Met Lys Leu Pro Ser Pro Asn Asp Ser Lys Phe Phe Gln Asn Leu Leu<br>                    995                    1000                  1005 | 3024 |
| gat gaa gag gat ttg gaa gat atg atg gat gct gag gag tac ttg<br>Asp Glu Glu Asp Leu Glu Asp Met Met Asp Ala Glu Glu Tyr Leu<br>                  1010                  1015                1020 | 3069 |
| gtc cct cag gct ttc aac atc cca cct ccc atc tat act tcc aga<br>Val Pro Gln Ala Phe Asn Ile Pro Pro Pro Ile Tyr Thr Ser Arg<br>                  1025                  1030                1035 | 3114 |

| | | | | | | | | | | | |
|---|---|---|---|---|---|---|---|---|---|---|---|
| gca | aga | att | gac | tcg | aat | agg | agt | gaa | att | gga | cac agc cct cct | 3159 |
| Ala | Arg | Ile | Asp | Ser | Asn | Arg | Ser | Glu | Ile | Gly | His Ser Pro Pro |
| | 1040 | | | | 1045 | | | | | 1050 | |

```
gca aga att gac tcg aat agg agt gaa att gga cac agc cct cct      3159
Ala Arg Ile Asp Ser Asn Arg Ser Glu Ile Gly His Ser Pro Pro
    1040                1045                1050 cct gcc tac acc ccc atg tca gga aac cag ttt gta tac cga gat      3204
Pro Ala Tyr Thr Pro Met Ser Gly Asn Gln Phe Val Tyr Arg Asp
    1055                1060                1065 gga ggt ttt gct gct gaa caa gga gtg tct gtg ccc tac aga gcc      3249
Gly Gly Phe Ala Ala Glu Gln Gly Val Ser Val Pro Tyr Arg Ala
    1070                1075                1080 cca act agc aca att cca gaa gct cct gtg gca cag ggt gct act      3294
Pro Thr Ser Thr Ile Pro Glu Ala Pro Val Ala Gln Gly Ala Thr
    1085                1090                1095 gct gag att ttt gat gac tcc tgc tgt aat ggc acc cta cgc aag      3339
Ala Glu Ile Phe Asp Asp Ser Cys Cys Asn Gly Thr Leu Arg Lys
    1100                1105                1110 cca gtg gca ccc cat gtc caa gag gac agt agc acc cag agg tac      3384
Pro Val Ala Pro His Val Gln Glu Asp Ser Ser Thr Gln Arg Tyr
    1115                1120                1125 agt gct gac ccc acc gtg ttt gcc cca gaa cgg agc cca cga gga      3429
Ser Ala Asp Pro Thr Val Phe Ala Pro Glu Arg Ser Pro Arg Gly
    1130                1135                1140 gag ctg gat gag gaa ggt tac atg act cct atg cga gac aaa ccc      3474
Glu Leu Asp Glu Glu Gly Tyr Met Thr Pro Met Arg Asp Lys Pro
    1145                1150                1155 aaa caa gaa tac ctg aat cca gtg gag gag aac cct ttt gtt tct      3519
Lys Gln Glu Tyr Leu Asn Pro Val Glu Glu Asn Pro Phe Val Ser
    1160                1165                1170 cgg aga aaa aat gga gac ctt caa gca ttg gat aat ccc gaa tat      3564
Arg Arg Lys Asn Gly Asp Leu Gln Ala Leu Asp Asn Pro Glu Tyr
    1175                1180                1185 cac aat gca tcc aat ggt ccc ccc aag gcc gag gat gag tat gtg      3609
His Asn Ala Ser Asn Gly Pro Pro Lys Ala Glu Asp Glu Tyr Val
    1190                1195                1200 aat gag cca ctg tac ctc aac acc ttt gcc aac acc ttg gga aaa      3654
Asn Glu Pro Leu Tyr Leu Asn Thr Phe Ala Asn Thr Leu Gly Lys
    1205                1210                1215 gct gag tac ctg aag aac aac ata ctg tca atg cca gag aag gcc      3699
Ala Glu Tyr Leu Lys Asn Asn Ile Leu Ser Met Pro Glu Lys Ala
    1220                1225                1230 aag aaa gcg ttt gac aac cct gac tac tgg aac cac agc ctg cca      3744
Lys Lys Ala Phe Asp Asn Pro Asp Tyr Trp Asn His Ser Leu Pro
    1235                1240                1245 cct cgg agc acc ctt cag cac cca gac tac ctg cag gag tac agc      3789
Pro Arg Ser Thr Leu Gln His Pro Asp Tyr Leu Gln Glu Tyr Ser
    1250                1255                1260 aca aaa tat ttt tat aaa cag aat ggg cgg atc cgg cct att gtg      3834
Thr Lys Tyr Phe Tyr Lys Gln Asn Gly Arg Ile Arg Pro Ile Val
    1265                1270                1275 gca gag aat cct gaa tac ctc tct gag ttc tcc ctg aag cca ggc      3879
Ala Glu Asn Pro Glu Tyr Leu Ser Glu Phe Ser Leu Lys Pro Gly
    1280                1285                1290 act gtg ctg ccg cct cca cct tac aga cac cgg aat act gtg gtg      3924
Thr Val Leu Pro Pro Pro Pro Tyr Arg His Arg Asn Thr Val Val
    1295                1300                1305 taa                                                              3927

<210> SEQ ID NO 2
<211> LENGTH: 1308
<212> TYPE: PRT
<213> ORGANISM: Homo sapiens
<220> FEATURE:
```

```
<221> NAME/KEY: misc_feature
<222> LOCATION: (317)..(317)
<223> OTHER INFORMATION: The 'Xaa' at location 317 stands for Lys, Glu,
      or Gln.
<220> FEATURE:
<221> NAME/KEY: misc_feature
<222> LOCATION: (452)..(452)
<223> OTHER INFORMATION: The 'Xaa' at location 452 stands for Lys, Glu,
      or Gln.
<220> FEATURE:
<221> NAME/KEY: misc_feature
<222> LOCATION: (542)..(542)
<223> OTHER INFORMATION: The 'Xaa' at location 542 stands for Lys, Glu,
      or Gln.
<220> FEATURE:
<221> NAME/KEY: misc_feature
<222> LOCATION: (544)..(544)
<223> OTHER INFORMATION: The 'Xaa' at location 544 stands for Arg, Gly,
      or Trp.
<220> FEATURE:
<221> NAME/KEY: misc_feature
<222> LOCATION: (563)..(563)
<223> OTHER INFORMATION: The 'Xaa' at location 563 stands for Lys, Glu,
      or Gln.
<220> FEATURE:
<221> NAME/KEY: misc_feature
<222> LOCATION: (836)..(836)
<223> OTHER INFORMATION: The 'Xaa' at location 836 stands for Lys, Glu,
      or Gln.
<220> FEATURE:
<221> NAME/KEY: misc_feature
<222> LOCATION: (872)..(872)
<223> OTHER INFORMATION: The 'Xaa' at location 872 stands for Lys, Glu,
      or Gln.

<400> SEQUENCE: 2

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
            20                  25                  30

Glu Asn Lys Leu Ser Ser Leu Ser Asp Leu Glu Gln Gln Tyr Arg Ala
        35                  40                  45

Leu Arg Lys Tyr Tyr Glu Asn Cys Glu Val Val Met Gly Asn Leu Glu
    50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
```

```
                    225                 230                 235                 240
Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
                260                 265                 270

Phe Gln Leu Glu His Asn Phe Asn Ala Lys Tyr Thr Tyr Gly Ala Phe
                275                 280                 285

Cys Val Lys Lys Cys Pro His Asn Phe Val Val Asp Ser Ser Ser Cys
                290                 295                 300

Val Arg Ala Cys Pro Ser Ser Lys Met Glu Val Glu Xaa Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
                340                 345                 350

Ile Asp Lys Phe Ile Asn Cys Thr Lys Ile Asn Gly Asn Leu Ile Phe
                355                 360                 365

Leu Val Thr Gly Ile His Gly Asp Pro Tyr Asn Ala Ile Glu Ala Ile
                370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
                420                 425                 430

Ser Leu Leu Ile Leu Lys Gln Gln Gly Ile Thr Ser Leu Gln Phe Gln
                435                 440                 445

Ser Leu Lys Xaa Ile Ser Ala Gly Asn Ile Tyr Ile Thr Asp Asn Ser
                450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
                500                 505                 510

Trp Gly Pro Gly Pro Asp Gln Cys Leu Ser Cys Arg Arg Phe Ser Arg
                515                 520                 525

Gly Arg Ile Cys Ile Glu Ser Cys Asn Leu Tyr Asp Gly Xaa Phe Xaa
530                 535                 540

Glu Phe Glu Asn Gly Ser Ile Cys Val Glu Cys Asp Pro Gln Cys Glu
545                 550                 555                 560

Lys Met Xaa Asp Gly Leu Leu Thr Cys His Gly Pro Gly Pro Asp Asn
                565                 570                 575

Cys Thr Lys Cys Ser His Phe Lys Asp Gly Pro Asn Cys Val Glu Lys
                580                 585                 590

Cys Pro Asp Gly Leu Gln Gly Ala Asn Ser Phe Ile Phe Lys Tyr Ala
                595                 600                 605

Asp Pro Asp Arg Glu Cys His Pro Cys His Pro Asn Cys Thr Gln Gly
                610                 615                 620

Cys Asn Gly Pro Thr Ser His Asp Cys Ile Tyr Tyr Pro Trp Thr Gly
625                 630                 635                 640

His Ser Thr Leu Pro Gln His Ala Arg Thr Pro Leu Ile Ala Ala Gly
                645                 650                 655
```

```
Val Ile Gly Gly Leu Phe Ile Leu Val Ile Gly Leu Thr Phe Ala
            660                 665                 670

Val Tyr Val Arg Arg Lys Ser Ile Lys Lys Arg Ala Leu Arg Arg
            675                 680                 685

Phe Leu Glu Thr Glu Leu Val Glu Pro Leu Pro Ser Gly Thr Ala
            690                 695                 700

Pro Asn Gln Ala Gln Leu Arg Ile Leu Lys Glu Thr Glu Leu Lys Arg
705                 710                 715                 720

Val Lys Val Leu Gly Ser Gly Ala Phe Gly Thr Val Tyr Lys Gly Ile
            725                 730                 735

Trp Val Pro Glu Gly Glu Thr Val Lys Ile Pro Val Ala Ile Lys Ile
            740                 745                 750

Leu Asn Glu Thr Thr Gly Pro Lys Ala Asn Val Glu Phe Met Asp Glu
            755                 760                 765

Ala Leu Ile Met Ala Ser Met Asp His Pro His Leu Val Arg Leu Leu
            770                 775                 780

Gly Val Cys Leu Ser Pro Thr Ile Gln Leu Val Thr Gln Leu Met Pro
785                 790                 795                 800

His Gly Cys Leu Leu Glu Tyr Val His Glu Lys Asp Asn Ile Gly
            805                 810                 815

Ser Gln Leu Leu Leu Asn Trp Cys Val Gln Ile Ala Lys Gly Met Met
            820                 825                 830

Tyr Leu Glu Xaa Arg Arg Leu Val His Arg Asp Leu Ala Ala Arg Asn
            835                 840                 845

Val Leu Val Lys Ser Pro Asn His Val Lys Ile Thr Asp Phe Gly Leu
            850                 855                 860

Ala Arg Leu Leu Glu Gly Asp Xaa Lys Glu Tyr Asn Ala Asp Gly Gly
865                 870                 875                 880

Lys Met Pro Ile Lys Trp Met Ala Leu Glu Cys Ile His Tyr Arg Lys
            885                 890                 895

Phe Thr His Gln Ser Asp Val Trp Ser Tyr Gly Val Thr Ile Trp Glu
            900                 905                 910

Leu Met Thr Phe Gly Gly Lys Pro Tyr Asp Gly Ile Pro Thr Arg Glu
            915                 920                 925

Ile Pro Asp Leu Leu Glu Lys Gly Glu Arg Leu Pro Gln Pro Pro Ile
            930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
            965                 970                 975

Met Ala Arg Asp Pro Gln Arg Tyr Leu Val Ile Gln Gly Asp Asp Arg
            980                 985                 990

Met Lys Leu Pro Ser Pro Asn Asp  Ser Lys Phe Phe Gln  Asn Leu Leu
            995                 1000                1005

Asp Glu  Glu Asp Leu Glu Asp  Met Met Asp Ala Glu  Glu Tyr Leu
            1010                1015                1020

Val Pro  Gln Ala Phe Asn Ile  Pro Pro Pro Ile Tyr  Thr Ser Arg
            1025                1030                1035

Ala Arg  Ile Asp Ser Asn Arg  Ser Glu Ile Gly His  Ser Pro Pro
            1040                1045                1050

Pro Ala  Tyr Thr Pro Met Ser  Gly Asn Gln Phe Val  Tyr Arg Asp
            1055                1060                1065

Gly Gly  Phe Ala Ala Glu Gln  Gly Val Ser Val Pro  Tyr Arg Ala
            1070                1075                1080
```

```
Pro Thr Ser Thr Ile Pro Glu Ala Pro Val Ala Gln Gly Ala Thr
    1085                1090                1095

Ala Glu Ile Phe Asp Asp Ser Cys Cys Asn Gly Thr Leu Arg Lys
    1100                1105                1110

Pro Val Ala Pro His Val Gln Glu Asp Ser Ser Thr Gln Arg Tyr
    1115                1120                1125

Ser Ala Asp Pro Thr Val Phe Ala Pro Glu Arg Ser Pro Arg Gly
    1130                1135                1140

Glu Leu Asp Glu Glu Gly Tyr Met Thr Pro Met Arg Asp Lys Pro
    1145                1150                1155

Lys Gln Glu Tyr Leu Asn Pro Val Glu Asn Pro Phe Val Ser
    1160                1165                1170

Arg Arg Lys Asn Gly Asp Leu Gln Ala Leu Asp Asn Pro Glu Tyr
    1175                1180                1185

His Asn Ala Ser Asn Gly Pro Pro Lys Ala Glu Asp Glu Tyr Val
    1190                1195                1200

Asn Glu Pro Leu Tyr Leu Asn Thr Phe Ala Asn Thr Leu Gly Lys
    1205                1210                1215

Ala Glu Tyr Leu Lys Asn Asn Ile Leu Ser Met Pro Glu Lys Ala
    1220                1225                1230

Lys Lys Ala Phe Asp Asn Pro Asp Tyr Trp Asn His Ser Leu Pro
    1235                1240                1245

Pro Arg Ser Thr Leu Gln His Pro Asp Tyr Leu Gln Glu Tyr Ser
    1250                1255                1260

Thr Lys Tyr Phe Tyr Lys Gln Asn Gly Arg Ile Arg Pro Ile Val
    1265                1270                1275

Ala Glu Asn Pro Glu Tyr Leu Ser Glu Phe Ser Leu Lys Pro Gly
    1280                1285                1290

Thr Val Leu Pro Pro Pro Tyr Arg His Arg Asn Thr Val Val
    1295                1300                1305

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
ggaaatagct gcacagtccg                                          20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
agaactggga taggcttgtg g                                        21

<210> SEQ ID NO 5
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 5
```

```
gtaaaacgac ggccagtaag ccaattcttt agaatatgat atgg        44
```

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6

```
tcttggctat tagcaacatg actc                              24
```

<210> SEQ ID NO 7
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 7

```
gtaaaacgac ggccagtaaa tcctcataaa ggagcaggag             40
```

<210> SEQ ID NO 8
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 8

```
gtaaaacgac ggccagttga attgagtcaa agacagggtg             40
```

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 9

```
tttggaaaca cacatgactc ttaaa                             25
```

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10

```
gtggagcagt aaccaagcaa g                                 21
```

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11

```
aaagcagaac cagtagtgaa tgttg                             25
```

<210> SEQ ID NO 12
<211> LENGTH: 38
<212> TYPE: DNA
<213> ORGANISM: Artificial Sequence
<220> FEATURE:

<223> OTHER INFORMATION: Synthetic oligonucleotide

<400> SEQUENCE: 12
gtaaaacgac ggccagtcct cctccacatc tagcacag                    38

<210> SEQ ID NO 13
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 13
gtaaaacgac ggccagtcct ttctcacttc ccaactttc                   39

<210> SEQ ID NO 14
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 14
gtaaaacgac ggccagtttg attcagtttc catttataca cca              43

<210> SEQ ID NO 15
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 15
gtaaaacgac ggccagttag gccaccaaag tcatttgc                    38

<210> SEQ ID NO 16
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 16
gtaaaacgac ggccagttga tgctcctggc acatagag                    38

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
tcttagagga agatttgcca cc                                     22

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
gcttcccatg ttcttcctcc                                        20

<210> SEQ ID NO 19

```
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 19
tgtggataat gtcttgtaca actgc                                          25

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
ggttgtcaag gcaaaccaag                                                20

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
aagcagacaa caaagttgca gag                                            23

<210> SEQ ID NO 22
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 22
gtaaaacgac ggccagttca gcaccattag tacaatccaa                          40

<210> SEQ ID NO 23
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 23
gtaaaacgac ggccagtgca cttccaactg aaggctaag                           39

<210> SEQ ID NO 24
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 24
gtaaaacgac ggccagtagg ccagcccaaa gactc                               35

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 25
```
tgattggtgt ttggattgac c                                              21

<210> SEQ ID NO 26
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 26
gtaaaacgac ggccagtgag tcgtttcttt cactagcttg c                        41

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
taggtttctt aatggccggt g                                              21

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 28
tgcttaggaa gcttcactgt tg                                             22

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29 tggcttttgat atccttgtgg c                                             21

<210> SEQ ID NO 30
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 30
ccatatgcag aagagacaaa tgc                                            23

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 31
tgaatccagt ggaggagaac c                                              21

<210> SEQ ID NO 32
<211> LENGTH: 35
<212> TYPE: DNA
<213> ORGANISM: Artificial Sequence
<220> FEATURE:

-continued

<223> OTHER INFORMATION: Synthetic oligonucleotide

<400> SEQUENCE: 32
gtaaaacgac ggccagtatg ggtgaagagg gcagg        35

<210> SEQ ID NO 33
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 33
gtaaaacgac ggccagtttc caggtatcag cacacagg        38

<210> SEQ ID NO 34
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 34
tgccttagag tgttcctcaa tg        22

<210> SEQ ID NO 35
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 35
gtaaaacgac ggccagtcaa tgaatgcaat caaagttcaa        40

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
ccaaagcaaa tcaaccacaa g        21

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
ggaatgactt tgaggagggc        20

<210> SEQ ID NO 38
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 38
gtaaaacgac ggccagtttt gctatgaaac tttacacaaa tca        43

<210> SEQ ID NO 39

```
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 39
gtaaaacgac ggccagtgtg tgggtaggtt tggttgtg                              38

<210> SEQ ID NO 40
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 40
gtaaaacgac ggccagtggt gaaactcttc agcttccag                             39

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 41
tctcctgacc tcatgatcca c                                                21

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 42
tacctcacac catcatcgga g                                                21

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
gagcaacaat tctgaccgga t                                                21

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 44
gaatggcgtg aacccagg                                                    18

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 45
```
cccatggcat cctgtaagta g                                               21

<210> SEQ ID NO 46
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 46
gtaaaacgac ggccagtcat ttcagagatg gtaccaggg                             39

<210> SEQ ID NO 47
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 47
gtaaaacgac ggccagtaag taagaaagtt ggcttgagaa gg                         42

<210> SEQ ID NO 48
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 48
gtaaaacgac ggccagtttc acaagctttg tttaacggac                            40

<210> SEQ ID NO 49
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 49
gtaaaacgac ggccagtaga ctgtatccgt cccagctc                              38

<210> SEQ ID NO 50
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 50
gtaaaacgac ggccagttct aggcagacag ttgtgaagc                             39

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 51
tttggcacct agtcaattca a                                               21

<210> SEQ ID NO 52
<211> LENGTH: 21
<212> TYPE: DNA
<213> ORGANISM: Artificial Sequence
<220> FEATURE:

-continued

<223> OTHER INFORMATION: Synthetic oligonucleotide

<400> SEQUENCE: 52
aggcaaatgg tagaaccaag g                                              21

<210> SEQ ID NO 53
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 53
taactgcttt aggaaattag gcttatc                                        27

<210> SEQ ID NO 54
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 54
gtaaaacgac ggccagtcaa agaggcgttc atatgttcc                           39

<210> SEQ ID NO 55
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 55
tgtttgtggt cctttccaca g                                              21

<210> SEQ ID NO 56
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 56
gtaaaacgac ggccagtggc atcacattga tttgagcta                           39

<210> SEQ ID NO 57
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 57
gtaaaacgac ggccagttaa ctcactgttg gcaaaggc                            38

<210> SEQ ID NO 58
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 58
gtaaaacgac ggccagtcag ctatctggca atttctattc tg                       42

<210> SEQ ID NO 59

```
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 59
gtaaaacgac ggccagtagg tagtctgggt gctgaagg                             38

<210> SEQ ID NO 60
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 60
gtaaaacgac ggccagtgac caccagagaa agagaggg                             38

<210> SEQ ID NO 61
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 61
gtaaaacgac ggccagt                                                    17

<210> SEQ ID NO 62
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 62
cggctctaga gccaccatga agccggcgac                                      30

<210> SEQ ID NO 63
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 63
atcggcggcc gcttacacca cagtattccg g                                    31

<210> SEQ ID NO 64
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 64
tcatttgtgc agcaacttct c                                               21

<210> SEQ ID NO 65
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 65
```

```
gcagacagtt gtgaagcaaa ag                                              22

<210> SEQ ID NO 66
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 66
caagctttaa ttcgcaaaga aga                                             23

<210> SEQ ID NO 67
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 67
tgctttagga aattaggctt atc                                             23

<210> SEQ ID NO 68
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 68
tttttccttc atgtttagat cattt                                           25

<210> SEQ ID NO 69
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 69
accttgtcct gctaatttgc tc                                              22

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
cagtagcaga gccacttgaa                                                 20

<210> SEQ ID NO 71
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 71
ctgtcctagg gttttggcat t                                               21

<210> SEQ ID NO 72
<211> LENGTH: 22
<212> TYPE: DNA
<213> ORGANISM: Artificial Sequence
<220> FEATURE:
```

<223> OTHER INFORMATION: Synthetic oligonucleotide

<400> SEQUENCE: 72
tgctatccta tttccatgct gt                                    22

<210> SEQ ID NO 73
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 73
tccccactta attattttta cctttt                                25

<210> SEQ ID NO 74
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 74
ggctactcag aggctaaggt g                                     21

<210> SEQ ID NO 75
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 75
tttttaattg attggtgttt gg                                    22

<210> SEQ ID NO 76
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 76
tgacctgtaa ggagtattct tttactac                              28

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
tgtccaccag gacaaatgta                                       20

<210> SEQ ID NO 78
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 78
tgtaaaacga cggccagt                                         18

<210> SEQ ID NO 79

```
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 79
caggaaacag ctatgacc                                              18
```